(12) United States Patent
Knezevic et al.

(10) Patent No.: US 6,969,615 B2
(45) Date of Patent: Nov. 29, 2005

(54) METHODS, DEVICES, ARRAYS AND KITS FOR DETECTING AND ANALYZING BIOMOLECULES

(75) Inventors: Vladimir Knezevic, Gaithersburg, MD (US); Michael R. Emmert-Buck, Silver Spring, MD (US); Galina Baibakova, Bethesda, MD (US); Dan-Paul Hartmann, Bethesda, MD (US); Stephen M. Hewitt, Potomac, MD (US); Capre Denise Mitchell, Winston Salem, NC (US); Kevin Gardner, Montgomery Village, MD (US)

(73) Assignees: 20/20 GeneSystems, Inc., Rockville, MD (US); The United States of America as represented by the Department of Health and Human Services, Washington, MD (US)

( * ) Notice: Subject to any disclaimer, the term of this patent is extended or adjusted under 35 U.S.C. 154(b) by 0 days.

(21) Appl. No.: 10/432,423

(22) PCT Filed: Nov. 20, 2001

(86) PCT No.: PCT/US01/44009

§ 371 (c)(1), (2), (4) Date: Dec. 1, 2003

(87) PCT Pub. No.: WO02/48674

PCT Pub. Date: Jun. 20, 2002

(65) Prior Publication Data

US 2004/0081979 A1 Apr. 29, 2004

Related U.S. Application Data

(63) Continuation-in-part of application No. 09/753,574, filed on Jan. 4, 2001, now abandoned, which is a continuation-in-part of application No. 09/718,990, filed on Nov. 20, 2000, now Pat. No. 6,602,661, which is a continuation-in-part of application No. PCT/US00/20354, filed on Jul. 26, 2000.

(60) Provisional application No. 60/296,475, filed on Jun. 8, 2001, provisional application No. 60/286,258, filed on Apr. 25, 2001, provisional application No. 60/304,031, filed on Jul. 9, 2001, and provisional application No. 60/145,613, filed on Jul. 26, 1999.

(51) Int. Cl.[7] ............................................. G01N 33/543
(52) U.S. Cl. .................... 436/518; 422/68.1; 435/6; 435/7.1; 435/7.9; 435/174; 435/287.1; 436/524; 436/528; 436/530; 436/531; 436/503
(58) Field of Search ........................... 422/68.1, 82.01, 422/56; 435/4, 6, 7.1, 7.9, 7.92, 174, 287.1; 436/518, 524, 503, 528, 530, 531

(56) References Cited

U.S. PATENT DOCUMENTS

| | | |
|---|---|---|
| 3,620,947 A | 11/1971 | Allen et al. |
| 4,176,069 A | 11/1979 | Metz et al. |
| 4,337,131 A | 6/1982 | Vesterberg |
| 4,613,567 A | 9/1986 | Yasoshima et al. |
| 4,716,101 A | 12/1987 | Thompson et al. |
| 4,795,562 A | 1/1989 | Walsh |
| 4,840,714 A | 6/1989 | Littlehales |
| 4,874,691 A | 10/1989 | Chandler |
| 5,047,135 A | 9/1991 | Nieman |
| 5,057,438 A | 10/1991 | Imai et al. |
| 5,078,853 A | 1/1992 | Manning et al. |
| 5,155,049 A | 10/1992 | Kauvar et al. |
| 5,173,159 A | 12/1992 | Dutertre |
| 5,238,651 A | 8/1993 | Chuba |
| 5,332,484 A | 7/1994 | Hilt |
| 5,387,325 A | 2/1995 | Opplt |
| 5,427,664 A | 6/1995 | Stoev et al. |
| 5,438,128 A | 8/1995 | Nieuwkerk et al. |
| 5,486,452 A | 1/1996 | Gordon et al. |
| 5,650,055 A | 7/1997 | Margolis |
| 5,679,310 A | 10/1997 | Manns |
| 5,716,508 A | 2/1998 | Starr |
| 5,741,639 A | 4/1998 | Ensing et al. |
| 5,843,657 A | 12/1998 | Liotta et al. |
| 5,993,627 A | 11/1999 | Anderson et al. |
| 6,013,165 A | 1/2000 | Wiktorowicz et al. |
| 6,064,754 A | 5/2000 | Parekh et al. |
| 6,087,134 A | 7/2000 | Saunders |
| 6,135,942 A | 10/2000 | Leptin |
| 6,232,067 B1 | 5/2001 | Hunkapiller et al. |
| 2002/0012920 A1 | 1/2002 | Gardner et al. |

| 2004/0081987 | A1 | * | 4/2004 | Knezevic et al. | 435/6 |

FOREIGN PATENT DOCUMENTS

| EP | 139373 | 5/1985 |
| EP | 0525723 | 2/1993 |
| WO | WO 98/20353 | 5/1998 |
| WO | WO 98/41863 | 9/1998 |
| WO | WO 00/45168 | 8/2000 |

OTHER PUBLICATIONS

Braun and Abraham, "Modified diffusion blotting for rapid and efficient protein transfer with PhastSystem," *Electrophoresis* 10:249–253, 1989.

Cleeve and Tua, "Isoelectric focusing of human tissue alkaline phosphatase isoenzymes in agarose gel," *Clinica Chimica Acta* 137:333–340, 1984.

Demczuk et al., "Identification and analysis of all components of a gel retardation assay by combination with immunoblotting," *Proc. Natl. Acad. Sci. USA* 90:2574–2578, Apr. 1993.

Englert et al., "Molecular profiling of human cancer: New opportunities," *Curr. Opin. Mol. Therap.* 1(6):712–719, 1999.

Englert et al., "Layered Expression Scanning: Rapid Molecular Profiling of Tumor Samples," *Cancer Res.* 60:1526–1530, Mar. 15, 2000.

Heukeshoven and Dernick, "Effective blotting of ultrathin polyacrylamide gels anchored to a solid matrix," *Electrophoresis* 16:748–756, 1995.

Inczedy–Marcsek et al., "Extraction of proteins within ultrathin–layer polyacrylamide electrophoresis (SDS–PAGE) and isoelectric focusing (PAGIF) of cryostat sections and tissue culture specimens," *Acta histochemica, Suppl.–Band XXXVI* S:377–394, 1988.

Legocki and Verma, "Multiple Immunoreplica ,Technique: Screening for Specific Proteins with a Series of Different Antibodies Using One Polyacrylamide Gel," *Anal. Biochem.* 111:385–392, 1981.

Manabe et al., "An Electroblotting Apparatus for Multiple Replica Technique and Identification of Human Serum Proteins on Micro Two–Dimensional Gels," *Anal. Biochem.* 143:39–45, 1984.

Neumann and Müllner, "Two replica blotting methods for fast immunological analysis of common proteins in two–dimensional electrophoresis," *Electrophoresis* 19:752–757, 1998.

Olsen and Wiker, "Diffusion blotting for rapid production of multiple identical imprints from sodium dodecyl sulfate polyacrylamide gel electrophoresis on a solid support," *J. Immunol. Methods* 220:77–84, 1998.

Sanchez et al., "Simultaneous analysis of cyclin and oncogene expression using multiple monoclonal antibody immunoblots," *Electrophoresis* 18:638–641, 1997.

Schumacher et al., "Direct tissue isoelectric focusing on ultrathin polyacrylamide gels. Applications in enzyme, lectin and immunohistochemistry," *Histochemical Journal* 22:433–438, 1990.

Schumacher and Trudrung, "Direct Tissue Isoelectric Focusing on Mini Ultrathin Polyacrylamide Gels followed by Subsequent Western Blotting, Enzyme Detection, and Lectin Labeling as a Tool for Enzyme Characterization in Histochemistry," *Anal. Biochem.* 194:256–258, 1991.

van der Sluis et al., "Immunochemical detection of peptides and proteins on press–blots after direct tissue gel isoelectric focusing," *Electrophoresis* 9:654–661, 1988.

* cited by examiner

*Primary Examiner*—Christopher L. Chin
(74) *Attorney, Agent, or Firm*—Klarquist Sparkman LLP

(57) ABSTRACT

The present disclosure is directed to devices, arrays, kits and methods for detecting biomolecules in a tissue section (such as a fresh or archival sample, tissue microarray, or cells harvested by an LCM procedure) or other substantially two-dimensional sample (such as an electrophoretic gel or cDNA microarray) by creating "carbon copies" of the biomolecules eluted from the sample and visualizing the biomolecules on the copies using one or more detector molecules (e.g., antibodies or DNA probes) having specific affinity for the biomolecules of interest. Specific methods are provided for identifying the pattern of biomolecules (e.g., proteins and nucleic acids) in the samples. Other specific methods are provided for the identification and analysis of proteins and other biological molecules produced by cells and/or tissue, especially human cells and/or tissue. The disclosure also provides a plurality of differentially prepared and/or processed membranes that can be used in described methods, and which permit the identification and analysis of biomolecules.

26 Claims, 26 Drawing Sheets

Layer #1
Anti-Rel Ab

Layer #2
Anti-CREB Ab

Layer #5
DNA$^{P32}$ trap

METHODS, DEVICES, ARRAYS AND KITS FOR DETECTING AND ANALYZING BIOMOLECULES

REFERENCE TO RELATED APPLICATIONS

This is the National Stage of International Application No. PCT/US01/44009, filed Nov. 20, 2001 (and published in English under PCT Article 21(2)), which is a Continuation-in-Part (CIP) of U.S. patent application Ser. No. 09/753,574 (filed Jan. 4, 2001), now Abandon, which is a CIP of U.S. patent application Ser. No. 09/718,990 (filed Nov. 20, 2000) now U.S. Pat. No. 6,602,661, which is a CIP of International Patent Application No. PCT US00/20354, filed Jul. 26, 2000 (and published in English under PCT Article 21(2)), and claims the benefit of U.S. Provisional Patent Application No. 60/145,613 (filed Jul. 26, 1999). Benefit is further claimed of U.S. Provisional Patent Application Nos. 60/286,258 (filed Apr. 25, 2001), 60/304,031 (filed Jul. 9, 2001), and 60/296,475 (filed Jun. 8, 2001). Each of these related applications is incorporated herein in their entirety.

STATEMENT OF GOVERNMENT RIGHTS

At least one of the inventors is an employee of an agency of the Government of the United States, and the Government may have certain rights in this invention.

FIELD OF THE DISCLOSURE

The present disclosure is directed to methods, devices, arrays, and kits for identifying and analyzing large numbers of biomolecules in a sample, such as a biological sample. The disclosure further relates to using these methods, devices, arrays, and kits to help determine the function and role of biomolecules in disease, and to correlating the presence, absence, or quantity of a combination of biomolecules with particular diseases, prognoses, or responses to therapies.

BACKGROUND OF THE DISCLOSURE

Now that the 50,000 or so genes that make up the human genome have been sequenced, tools are needed to determine when and in what type of tissue those genes are active so as to ascertain their function and role, particularly in disease. This effort, often referred to as "functional genomics" and "proteomics," is especially important in efforts to discover new drugs since new pharmaceutical agents are being designed to target specific enzymes, receptors, and other proteins. Eventually, proteomic information will be used in clinical diagnostics to help guide treatment selection in the emerging era of "personalized medicine."

Some believe that the 100,000 human genes may turn out to produce up to a million different protein variants due to post-translational and other modifications. Within the next decade the pharmaceutical industry is expected to identify up to 10,000 proteins against which human therapeutics can be directed. Additional therapeutics, gene modifiers, expression modifiers, and valuable biomolecules also are expected to be developed or identified through the extension of proteomics to the analysis of non-human animals and plants.

Although there may be up to a million different protein variants in humans, only about 10,000–15,000 proteins are expressed in any particular cell type. Thus, for example, liver cells have essentially the same genome as skin cells taken from the same individual, but the two cell populations express substantially different sets of proteins. It is often desirable, therefore, to profile and compare the patterns of proteins (i.e., the "proteome" of a cell) in different cell populations (e.g., diseased and normal tissue; fetal and mature tissue; human and non-human tissue, etc.) to identify targets for drugs.

One common approach to establishing or confirming the association of gene activity with disease is through expression analysis. DNA microarrays are used to survey differential expression patterns of thousands of genes from extracts taken from samples of tissues representing various diseases. If particular genes are expressed in diseased tissue but not in normal tissue they may be relevant as diagnostic markers and targets of pharmaceutical intervention. One disadvantage with this approach is that the sample being tested is disassociated from the tissue from which it was isolated, thereby losing the ability to observe gene expression patterns in the context of the tissue in which the genes are active. Since the morphological relationship is not preserved in microarray analysis, it is hard to know what component of the sample is responsible for the changes observed in gene expression. Also, microarray analysis is usually performed on a homogenized sample of tissue, making it virtually impossible to ascribe expression to a specific cell type, let alone a specific cell.

In situ detection and visualization of proteins traditionally has been accomplished through immuno-histochemistry (IHC). This technique involves the mounting a thin tissue section on the glass slide and visualizing a protein of interest with a detectable antibody that has specific binding affinity for the target protein. Because of certain technical limitations of IHC, only one or two proteins from a single tissue section can be achieved. Also, proteins are still embedded in the tissue and are not presented to the antibodies in the most appropriate way (proteins are not highly denatured) lowering the success rate of the antibody reactivity.

The most widely used method for identifying and measuring proteins and nucleic acids that have been removed from tissue samples is gel electrophoresis. Electrophoresis generally refers to techniques for separating or resolving molecules in a mixture under the influence of an applied electric field. Separation is based on difference in (usually) the size and/or charge of the molecules. Molecules separated by electrophoresis are often visualized by staining with a non-specific dye, such as Coomassie blue (for proteins) or ethidium bromide (for nucleic acids). Such dye staining does not specifically identify individual molecules. Furthermore, ubiquitous dye staining is generally not very sensitive.

More sensitive detection methods exist, such as antibody-based detection for proteins. In particular, immunoblotting, also known as "Western blotting," is often used to detect gel-separated proteins. This technique uses detectable antibodies specific to the proteins of interest in lieu of a ubiquitous stain. A key imitation of the technique is its low throughput; at most only a handful of proteins can be identified from a single lane of an immunoblot on a single blot, due to overlapping banding patterns and cross reactivity of antibodies with different proteins in the sample. Thus, immunoblotting is typically performed using only one antibody per membrane to ensure specificity.

Though it is possible to strip and re-probe an immunoblot, stripping will also remove protein of the sample that had been bound to the membrane, thus encumbering quantitative analysis of the sample. Moreover, the proportion of each individual protein removed from the membrane by such treatment will vary depending upon the nature of the protein, which further clouds efforts to quantitate the relative amounts of protein initially present in the sample. There remains a clear need to develop blotting techniques that permit larger numbers of antigens to be detected simultaneously from a single test sample.

It would be desirable to have high-throughput approaches for detecting, identifying and comparing large numbers of biomarkers that is relatively inexpensive, can be used by ordinary laboratory personnel, and readily permits the capture, organization, and analysis of the data generated thereby.

SUMMARY OF THE DISCLOSURE

The present disclosure is directed to devices and methods for detecting biomolecules in a substantially two-dimensional sample (e.g. tissue section, tissue array, electrophoretic gel, and so forth) by creating substantial copies of the biomolecules eluted from the sample. The biomolecules then can be visualized on the copies using detectors, for example antibodies or DNA probes, having specific affinity for the biomolecules of interest.

The present disclosure is further directed to methods and devices for identifying the pattern of biomolecules (e.g., proteins and nucleic acids) expressed in tissue samples, and for correlating the expression pattern with, for instance, various diseases, prognoses, or responses to therapies.

Provided herein are methods of detecting biomolecules in a sample, which methods involve providing a stack of at least two layered membranes; applying the sample to the stack under conditions that permit movement of the biomolecules through multiple layered membranes of the stack, and allow capture of at least a portion of the biomolecules on the membranes, and detecting the biomolecules on one or more of the multiple membranes. In specific examples of such methods, the biomolecules are captured directly by the membranes. Certain membranes for use in such methods have a high affinity but low capacity for biomolecules, for instances proteins, nucleic acids, lipids, carbohydrates, or combinations thereof.

Another embodiment of the disclosure is a method of making multiple substantial copies (which need not be identical) of a biological sample. These methods involve providing a stack of layered membranes, wherein the membranes permit biomolecules applied to the stack to move through a plurality of the membranes, while capturing (for instance, directly) at least a portion of the biomolecules on multiple membranes and applying the biological sample to the stack, under conditions that allow the multiple membranes to capture at least a portion of the biomolecules from the sample. This forms the multiple substantial copies of the biological sample.

Samples for use in examples of provided methods are (or can be made) substantially two-dimensional; representative non-limiting types of samples include tissue sections, tissue microarrays, tissue macroarrays, laser capture microdissected tissue samples, and electrophoretic gels (e.g., 1-D or 2-D electrophoretic gels).

Yet a further embodiment is a method of creating a set of microarray copies, which method involves providing a stack of layered membranes, and applying a plurality of molecules (e.g. DNA probes, antibodies, or a combination thereof), to the stack of layered membranes. In examples of such methods, the stack of layered membranes includes a plurality of substrates through which the molecules move, and in which a portion of the molecules are directly captured by one or more of the substrates.

Another specific embodiment is a method of analyzing biomolecules in a tissue sample, which method involves providing at least one membrane (in some embodiments, a plurality of membranes), positioning the at least one (or more) membrane in contact with the tissue sample, and applying heat and/or pressure to the tissue sample, whereupon biomolecules are transferred from the tissue sample onto the at least one membrane (referred to generally as contact transfer). One or more of the biomolecules can then be analyzed on the at least one membrane.

Another example of a provided method is a method of replicating biomolecular content of a tissue array (such as a micro- or macroarray), which method involves providing the tissue array and transferring biomolecules from the tissue array onto a plurality of membranes so as to produce at least one replicate of the biomolecular content of the tissue array.

The disclosure also provides a method of analyzing cellular material embedded on an LCM transfer film, which method involves providing one or more membranes, positioning the one or more membranes adjacent to the LCM transfer film, transferring biomolecules from the cellular material to the one or more membranes, and detecting the biomolecules on the membranes.

Further encompassed methods include methods for analyzing the proteome of a biological sample. Examples of such methods involve separating at least one protein from another protein present in the biological sample, transferring a portion of the separated protein to a plurality of membranes in a stacked configuration, incubating each of the membranes in the presence of one or more different species of predetermined ligand molecules (or detector molecules) under conditions sufficient to permit binding between the separated protein and a ligand/detector capable of binding to such protein; and analyzing the proteome by determining the occurrence of binding between the protein and any of the species of predetermined ligand molecules.

A further embodiment is a method for identifying biomolecules that have been separated on a solid support (e.g., a 1-D or 2-D gel). Such methods involve providing a solid support containing the separated biomolecules, wherein the support has an upper side and a lower side, applying a first stack of membranes to the upper side and a second stack of membranes to the lower side, permitting the biomolecules to be transferred from the support to the first and second membrane stacks, and separating the membranes. The transferred biomolecules can then be detected, identified, or otherwise analyzed on at least one of the membranes.

The disclosure also provides kits. Examples of kits include a membrane array for detecting biomolecules in a sample, and one or more containers of detector molecules for detecting molecules captured on membranes of the array. Arrays included in such kits contain a plurality of membranes, each of which has substantially a same affinity for biomolecules that may be analyzed using the kit.

Another kit embodiment is a kit for comparing the molecular profiles of tissue samples. Such kits contain at least one tissue microarray, and at least one replicate of the tissue microarray. Replicates contained in such kits may be made, for instance, using methods described herein.

Also provided are kits for replicating a pattern of biomolecules from a tissue sample, which kits include a plurality of membranes, each having a coating on its upper and/or lower surfaces to increase specific binding of a target biomolecule, a quantity of transfer buffer, and a fluid impervious enclosure (for instance, a heat-sealable bag).

Another example of a described kit is a kit for analyzing a proteome, which kit contains a plurality of membranes, each having a affinity for at least one protein, and a plurality of reagent species (such as detector molecules, particularly labeled detectors), each species is adapted to detect one or more specific proteins bound to the membranes.

Further embodiments are membranes unit for use in blotting, which unit includes a stack of at least two porous membranes (examples of which have a thickness no greater than about 30 microns), and a frame, mounted to the membranes, which has a thickness no greater than about 300 microns.

Also provided are porous membranes having a high affinity but low capacity for biomolecules. Examples of such membranes include a core substrate and a coating, and generally are no more than about 30 microns thick. Specific examples of such membranes contain polycarbonate in the core substrate and nitrocellulose in the coating.

The foregoing and other advantages and features will become hereinafter apparent, and may be more clearly understood by reference to the following detailed description, the appended claims, and the several views illustrated in the drawings.

BRIEF DESCRIPTION OF THE DRAWINGS

FIG. 26 is a schematic illustration comparing the binding capacity of membranes constructed of nitrocellulose and polycarbonate, both coated and uncoated.

BRIEF DESCRIPTION OF THE SEQUENCE LISTING

Figure 1:
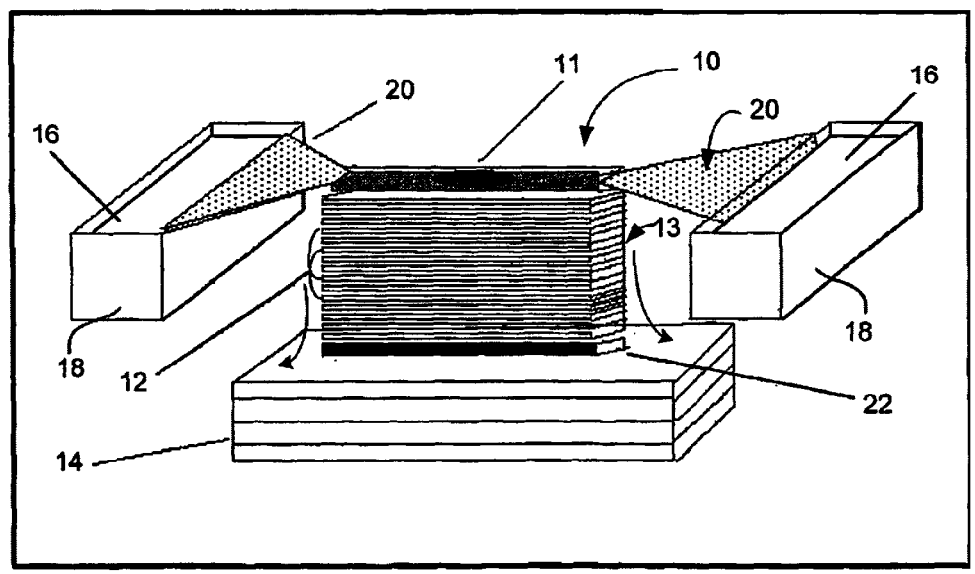
FIG. 1 is a perspective view of a membrane array, shown transferring molecules from a tissue section using wicking transfer.

SEQ ID NO: 1 shows the nucleic acid sequence of a 43-residue synthetic hybridization oligonucleotide.

DETAILED DESCRIPTION OF THE DISCLOSURE

I. Explanation of Certain Terms

"Addressable" refers to that which is capable of being reliably and consistently located and identified, as in an addressable location on an array or a gel.

"Affinity" means the chemical attraction or force between molecules.

"Antibody cocktails" means mixtures of between two to about 100 different detector antibodies.

"Array" means two or more.

"Biological sample" means any solid or fluid sample obtained from, excreted by or secreted by a living organism (including microorganisms, plants, animals, and humans).

"Biomolecules" are molecules typically produced by living organisms including peptides, proteins, glycoproteins, nucleic acids, fatty acids, and carbohydrates.

"Capacity" means the ability to receive, hold, or absorb biomolecules from the sample.

"Captor" means a molecule, such as an antibody or DNA probe, that is anchored to a membrane and has an affinity (such as a specific affinity) for one of the biomolecules. biomolecule is not directly conjugated to the membrane.

"cDNA" refers to a DNA molecule lacking internal, non-coding segments (introns) and regulatory sequences which determine transcription. cDNA may be synthesized in the laboratory by reverse transcription from messenger RNA extracted from cells.

"Counter-ligand staning" is intended to refer to any detection technique that detects the presence of ligand that is not bound to a protein of the biological sample, and thus reveals (as, for example, by an absence of staining, etc.) the presence of ligand that is bound to a protein of the biological sample "Detector" means a molecule, such as an antibody or DNA probe, that is free in solution (i.e. not anchored to a membrane) and has an affinity for one of the sample components.

"Direct capture" means the conjugation or binding of a biomolecule directly onto the surface of the membrane without the aid of a captor antibody or the like.

"DNA" is a long chain polymer that contains the genetic material of most living organisms (the genes of some viruses are made of ribonucleic acid (RNA)). The repeating units in DNA polymers are four different nucleotides, each of which includes one of the four bases (adenine, guanine, cytosine and thymine) bound to a deoxyribose sugar to which a phosphate group is attached. Triplets of nucleotides (referred to as codons) code for each amino acid in a polypeptide, or for a stop signal. The term "codon" is also used for the corresponding (and complementary) sequences of three nucleotides in the mRNA into which the DNA sequence is transcribed.

"EST" (Expressed Sequence Tag) is a partial DNA or cDNA sequence, typically of between 500 and 2000 sequential nucleotides, obtained from a genomic or cDNA library, prepared from a selected cell, cell type, tissue or tissue type, organ or organism, which corresponds to an mRNA of a gene found in that library. An EST is generally a DNA molecule sequenced from and shorter than the cDNA from which it is obtained.

"Fluorophore" refers to a chemical compound, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515–540 λ.Red fluorophores, for example Texas Red, Cy5 and tetramethylrhodamine, are characterized by their emission at wavelengths generally in the range of 590–690 λ.

Examples of fluorophores that may be used are provided in U.S. Pat. No. 5,866,366 to Nazarenko et al., and include for instance: 4-acetamido-4'-isothiocyanatostilbene-2, 2'disulfonic acid, acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-trifluoromethylcouluarin (Coumaron 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)4-methylcoumarin; diethylenetriamine pentaacetate; 4,4'-diisothiocyanatodihydro-stilbene-2,2'-disulfonic acid; 4, 4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron .RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

"High throughput genomics" refers to application of genomic or genetic data or analysis techniques that use microarrays or other genomic technologies to rapidly identify large numbers of genes or proteins, or distinguish their structure, expression, or function from normal or abnormal cells or tissues.

"Hybridization" refers to an interaction between nucleic acid molecules that are complementary to each other. Hybridization is based on hydrogen bonding, which includes Watson-Crick, Hoogsteen or reversed Hoogsteen hydrogen bonding between complementary nucleotide units. For example, adenine and thymine are complementary nucleobases that pair through formation of hydrogen bonds. "Complementary" refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotides are complementary to each other at that position. The oligonucleotide and the DNA or RNA are complementary to each other when a sufficient number of corresponding positions in each molecule are occupied by nucleotide units which can hydrogen bond with each other.

"Specifically hybridizable" and "complementary" are terms that indicate a sufficient degree of complementarity such that stable and specific binding occurs between the oligonucleotide and the DNA or RNA target An oligonucleotide need not be 100% complementary to its target DNA sequence to be specifically hybridizable.

Hybridization conditions resulting in particular degrees of stringency will vary depending upon the nature of the hybridization method of choice and the composition and length of the hybridizing DNA used. Generally, the temperature of hybridization and the ionic strength (especially the Na+ concentration) of the hybridization buffer will determine the stringency of hybridization. Calculations regarding hybridization conditions required for attaining particular degrees of stringency are discussed by Sambrook et al. *Molecular Cloning: A Laboratory Manual*, Cold Spring Harbor Laboratory Press (1989), chapters 9 and 11, herein incorporated by reference "Indirect capture" means the conjugation or binding of a biomolecule onto a captor antibody or the like which in turn is bound to the surface of the membrane. Thus, with indirect capture the biomolecule is not directly conjugated to the membrane.

"Identical" means having substantially the same affinity for biomolecules.

"Label" refers to detectable markers or reporter molecules, which can be attached for instance to a specific biomolecule (e.g., a protein or nucleic acid). Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

"Nucleic acid" refers to a deoxyribonucleotide or ribonucleotide polymer in either single or double stranded form, and unless otherwise limited, and encompasses known analogues of natural nucleotides that hybridize to nucleic acids in a manner similar to naturally occurring nucleotides.

"Membrane" means a thin sheet of natural or synthetic material that is porous or otherwise at least partially permeable to biomolecules.

"Microarray" is an array that is miniaturized so as to require microscopic examination for visual evaluation.

"Polypeptide" means any chain of amino acids, regardless of length or post-translational modification (e.g., glycosylation or phosphorylation).

"Proteomics" means the identification or analysis of a proteome. A proteome is the group of proteins expressed and/or present in a biological sample.

"Sample" means a material that contains biomolecules including tissue, gels, bodily fluids, and individual cells in suspensions or in pellet, as well as materials in containers of biomolecules such as microtiter plates.

"Stack" refers to adjacent substrates, whether oriented horizontally, vertically, at an angle, or in some other direction. The substrates (e.g., membranes) may be spaced or touching, for example contiguous.

"Subject" refers to living, multicellular vertebrate organisms, a category that includes both human and veterinary subjects for example, mammals, birds, and more particularly primates.

II. General Description of Several Embodiments

Particular embodiments are especially useful in connection with archival tissue samples that have been fixed and embedded, for instance in paraffin. Whole tissue sections, tissue macroarrays, and arrays of minute tissue sections, e.g., in the format of a tissue microarray, all may be analyzed according to the disclosed methods, as can other samples from which biomolecules are to be detected (e.g., gels produced from 1- or 2-D separation of proteins or nucleic acids). The biomolecules on the copies can be visualized using detector molecules ("probes"), for example antibodies, lectins, or DNA hybridization probes, having specific affinity for the biomolecule(s) of interest.

Specific embodiments provided herein include direct layered expression scanning techniques, which utilize a stack of "blank" membranes that are not specific for any particular target molecule. Instead, all (or a subset, e.g., proteins or nucleic acid) biomolecules in a sample ubiquitously bind to such membranes so as to give the user the flexibility of detecting a wide variety of biomolecules in an open format.

Thin membranes in a stacked or layered configuration are applied to the sample, such as a tissue section, or protein or nucleic acid gel, and reagents and reaction conditions are provided so that at least a portion of the biomolecules are eluted from the sample and transferred onto a plurality of the stacked membranes. This produces multiple substantial replicas of the biomolecular content of the sample. The resultant loaded (treated) membranes (or layers) are then separated. Each membrane may be incubated with one or more different detectors (for example antibodies) specific for a particular biomolecule (such as a protein) of interest. The detectors employed are labeled or otherwise detectable using any of a variety of techniques, for instance chemiluminescence.

In an example in which proteins are detected, each membrane has essentially the same pattern of proteins bound to it, but different combinations of proteins are made visible (detectable) on each membrane due to the particular detectors (e.g., antibodies) selected to be applied. For example, one membrane layer may display proteins involved in programmed cell death (apoptosis) while an adjacent layer may display enzymes involved in cell division such as tyrosine kinases.

In addition to proteins, nucleic acids may be targeted by using labeled DNA probes as detectors in lieu of antibodies. Moreover, different types of target biomolecules may be detected in different layers. For example, both protein and nucleic acid targets can be detected in parallel by applying protein-specific detectors (e.g., antibodies) and nucleic acid detectors (e.g. hybridization probes) to different layers of the array.

According to certain methods of the present disclosure, a sample from which biological molecules are to be transferred (e.g., a tissue section or gel) is positioned in contact with a face of a stack of membranes and both the sample and stack (an assembled "contact transfer stack") are placed inside a fluid impervious enclosure such as a plastic bag or the like. In certain embodiments, the sample is supported by a substantially fluid impervious support, such as a glass slide; in these embodiments, the stack of membranes is placed on the other side of the sample. In other embodiments, the sample from which biomolecules are to be transferred is not supported by an impervious support, and the sample is placed between members of the membrane stack, such that one or more membranes is placed adjacent to each of two faces of the sample.

Also within the enclosure is a liquid transfer reagent. Heat and/or pressure are applied to the contents of the enclosure (from one or both sides) so as to permit proteins and other molecules to be transferred from the sample to the membrane stack. This produces multiple copies or replicas of the biomolecular content of the tissue sample. The processed membranes (or layers) then may be separated and incubated with one or more different probes (e.g. nucleic acid hybridization probes or antibodies) specific for particular targets of interest. The probes employed are labeled or otherwise detectable using any of a variety of techniques such as chemiluminescence.

While each membrane has essentially the same pattern of biomolecules (including proteins and/or nucleic acids) bound to it, different combinations of such biomolecules are made visible on each membrane due to the particular probes or antibodies selected to be applied. For example, one membrane layer may be used to detect proteins involved in programmed cell death (apoptosis), while an adjacent layer may be used in detecting enzymes involved in cell division, such as tyrosine kinases. In addition to proteins, nucleic acids may be targeted by using labeled DNA probes in lieu of antibodies. Moreover, both protein and nucleic acid targets can be detected in parallel by applying both antibodies and probes to different layers of the array of membranes to which the biomolecules have been transferred.

In one embodiment, the disclosed methods may be used for a side-by-side comparison of the protein expression patterns in different archival tissue samples, for instance from patients with different diseases, disease outcomes, or responses to therapies. Thus, for example, where patient response to a particular drug can be correlated to a specific protein expression pattern from the diseased organ this provides a useful tool for predicting whether future patients likely will benefit or be harmed by that drug.

Advantageously, provided methods may be used to screen archival tissue, which is usually formalin fixed and paraffin embedded. Provided methods may also be used for examination of proteins that cannot be detected with antibodies in situ but can be detected after the protein has been transferred onto a membrane. Furthermore, provided methods enable the quantitative analysis of targets in tissue, for example, the quantification of cell surface receptor density on malignant cells.

Beneficially, the methods, device, arrays, and kits provided herein can be used with laser capture microdissected samples, permitting molecular analysis of tissue without protein or nucleic acid purification as a prerequisite. These embodiments retain the two-dimensional relationship of distinct cell populations within the same tissue section so as to preserve the spatial relationships between the dissected cells and permit different cell types to be processed and analyzed in parallel.

Thus, methods are provided for detecting biomolecules in a sample collected by LCM, by eluting the biomolecules away from the microdissected sample and binding them to one or more membranes in a layered or stacked configuration, then visualizing the biomolecules on the membranes.

In examples of such methods, cellular samples embedded in/on an LCM transfer film (or the like) are positioned adjacent to a stack of one or more membranes, and reagents and reaction conditions are provided so that the biomolecules are eluted from the cellular sample and transferred onto the membrane(s). Biomolecules on the membrane then can be detected and visualized using detector molecules (e.g., antibodies or DNA probes) having specific affinity for the biomolecule(s) of interest.

Also provided are methods for identifying and analyzing biomolecules that have been resolved via electrophoretic, chromatographic, or fractionating means. Examples of such methods are sensitive enough to detect proteins in low abundance, yet able to detect large numbers of proteins in a high-throughput manner preferably without requiring expensive and sophisticated laboratory equipment.

Thus, according to one aspect of a method of the present disclosure, biomolecules (e.g., proteins or nucleic acids) that have been electrophoretically separated on a gel are transferred from the gel onto a stack of membranes. In certain examples, these membranes are constructed and/or chemically treated to have a high affinity but low capacity for the biomolecules. This allows the creation multiple replicates of the molecular content of the gel. After transfer, the membranes are separated and each is incubated with a one or a unique mixture (also referred to as a "cocktail") of detectors (e.g., antibodies specific for a particular subset of proteins, nucleic acid probes, etc). Thus, while each membrane has essentially the same pattern of biomolecules bound to it, different combinations are made visible on each membrane due to the particular detector (or set of detectors) selected to corresponds to the particular layer. In specific examples, the detector cocktail is an antibody cocktail that has been carefully formulated so that no two antibodies in a cocktail bind overlapping or adjacent protein spots. Thus, protein spots that are too close together to be discriminated on a single membrane are detected on separate membranes according to the inventive method herein.

According to certain disclosed methods, proteins that have been separated (either by in situ synthesis, electrophoretically, chromatographically, etc.) on a gel, tissue or other support are transferred from the gel/support onto the membrane stack to allow the creation of multiple replicates or imprints of the protein content of the gel/support. With regard to gels, the amount of protein loaded into the wells is greater than the amount conventionally loaded so as to permit a more even and uniform distribution of the proteins throughout the stack.

Since antibodies can be used to detect many post-translational protein modification (e.g. phosphorylation), certain examples of disclosed methods can be employed to identify or analyze protein function as well as structure. In addition to 2-D gels, described methods can be used for one-dimensional gels such as the identification of transcription factors separated by a gel-shift assay.

In detail, one specific embodiment is a method of analyzing the proteome of a biological sample. Such a method involves separating the protein from another protein present in the sample; transferring a portion of the separated protein to a plurality of membranes (for instance, 2, 10, 20 or more) in a stacked configuration; incubating each of the membranes in the presence of one or more species of predetermined ligand molecules (e.g., 2, 10, 20 or more) under conditions sufficient to permit binding between the separated protein and a ligand capable of binding to such protein; and analyzing the proteome by determining the occurrence of binding between the protein and any of the species of predetermined ligand molecules.

Another embodiment is a method for analyzing the extent of similarity between the proteomes of two or more samples. Such a method involves, for each such sample, separating a protein of such sample from another protein present in the sample; transferring a portion of the separated protein to a plurality of membranes (e.g., 2, 10, 20 or more) in a stacked configuration; incubating two or more of the membranes in the presence of one or more species of predetermined ligand molecules (e.g., 2, 10, 20 or more) under conditions sufficient to permit binding between the separated protein and a ligand capable of binding to such protein; and analyzing the extent of similarity between the proteomes by comparing the separated proteins of each such sample with the separated proteins of another such sample for the occurrence of binding between the separated protein and any of the species of predetermined ligand molecules.

Another embodiment is a method for uniquely visualizing a desired predetermined protein if present in a biological sample. This method involves separating the proteins present in the sample from one another; transferring a portion of the separated proteins of the sample to a plurality of membranes (for instance, 2, 10, 20 or more) in a stacked configuration; incubating two or more of the membranes in the presence of one or more species of predetermined detector/ligand molecules (e.g., 2, 10, 20 or more) under conditions sufficient to permit binding between desired predetermined protein and a ligand capable of binding to such protein; and visualizing any binding between the protein and any of the species of predetermined ligand molecules.

Also provided are embodiments of all such methods wherein the separation of the protein from another protein present in the sample is accomplished by electrophoresis (for instance, 2-dimensional (2-D) gel electrophoresis).

Further embodiments include all such methods wherein the sample is obtained from mammalian cells or tissue, and particularly from human cells or tissue, and the embodiments wherein the mammalian cells or tissue are human cells or tissue and the separated protein is a product of a human gene.

It is contemplated that the detector/ligand species can be any of a variety of molecule types. Thus, also provided are embodiments of all such methods wherein at least one of the species of detector/ligand is an antibody, an antibody fragment, a single chain antibody, a receptor protein, a solubilized receptor derivative, a receptor ligands, a metal ion, a virus, a viral protein, an enzyme substrate, a toxin, a toxin candidate, a pharmacological agent, a pharmacological agent candidate, a hybridization probe, a oligonucleotide, and others as discussed herein.

Other embodiments include all such methods wherein the binding of at least one of the species of detector/ligand is dependent upon the structure of the separated biomolecule (e.g., protein or nucleic acid). It still further provides the embodiments of all such methods wherein the binding of at least one of the species of detector/ligand is dependent or upon the function of the separated biomolecule (e.g., protein or nucleic acid).

The disclosure also provides all such methods wherein at least one of the membranes is incubated with more than one species of ligand or detector molecule. Also provided are embodiments of all such methods wherein at least two membranes are employed, at least 10 membranes are employed, or at least 20 membranes are employed.

Further provided are the embodiments of all such methods wherein at least at least two ligand species or detector molecules are employed, wherein at least 10 are employed, or at least 20 or more are employed.

Additional embodiments are membranes that have a high affinity but a low capacity for proteins and/or other biomolecules so as to allow the creation of multiple replicates or imprints of the proteins eluted from a gel. Examples of these membranes are substantially thinner than those conventionally used for blotting. The membranes are optionally provided with (or within) a frame, so that they may be easily handled and manipulated when separated from that stack. The frame optionally defines a channel to permit release of air and fluid trapped between adjacent membranes. Removable tabs or the like also may be provided on each frame to permit the stack to be held together, for instance when it is applied to the gel.

Loaded membranes may be scanned or otherwise digitally imaged using one of several commercially available scientific imaging instruments. Imaging instrumentation and software, such as those described herein, may be employed to permit viewing, analysis, and/or interpretation of the expression patterns from the sample (e.g., a tissue sample or other two-dimensional source, such as a gel). Software may be provided with template images corresponding to each of the membrane images. This allows the identity of the biomolecule in each defined locus (e.g., a spot on a 2-D gel, a band on a 1-D gel, or a localized molecular deposit in a tissue sample) to be confirmed based on its vertical and horizontal position. The software also can allow the density of each locus to be calculated so as to provide a quantitative read-out The software may also have links to a database of images generated from other gels to allow comparisons to be made between different diseased and normal samples. In addition to computerized analysis of membranes, the source sample (e.g., actual tissue sections or other substantially two-dimensional source) or a substantially similar sample (e.g., an adjacent tissue slice) may be analyzed with conventional techniques (e g., histochemical techniques) to confirm or compare the digital analysis.

Also provided herein are kits that include a plurality of membranes (e.g. 3 or more, for instance 5, 10, 15, 25, 50, or 100 or more membranes) in a stack or other configuration that permits them to be stacked. Optionally, the provided kits may further include one or more different detectors, such as cocktails of antibodies or hybridization probes, to be applied to the treated membranes for biomolecule detection/analysis. The kits may also provide one or more additional components, such as a volume of a transfer reagent, a fluid impervious enclosure (for instance, a sealable bag), one or more pieces of filter paper, and/or a tissue array contained on a slide or other comparison sample or control sample. Optionally such kits may also include instructions for how to use the kit to detect, analyze, and/or identify one or more biomolecules. Detection chemistries may be included, which are tailored to coincide with the detector molecules provided with the kit or anticipated for use with the other kit components. The aforementioned software may also be included in the kit, or may be accessible via modem or the Internet.

In certain embodiments, the methods and kits according to the present disclosure allow up to several thousand discrete biomolecule (e.g., protein) loci to be identified, annotated, and, at the user's option, compared to the pattern of loci generated from other samples stored in a database.

One specific example of a provided kit for analyzing a proteome includes a plurality of membranes, each having a specific affinity for at least one protein, and a plurality of detector/ligand species (e.g., species such as an antibody, an antibody fragment, a single chain antibody, a receptor protein, a solubilized receptor derivative, a receptor ligands, a metal ion, a virus, a viral protein, an enzyme substrate, a pharmacological agent, and a pharmacological agent candidate), each adapted to detect one or more specific proteins bound to the membranes.

Also provided in another embodiment is a kit for uniquely visualizing a desired predetermined protein if present in a biological sample. Such a kit includes a plurality of membranes, each having a specific affinity for at least one protein, and a plurality of detector/ligand species (e.g., species such as an antibody, an antibody fragment, a single chain antibody, a receptor protein, a solubilized receptor derivative, a receptor ligands, a metal ion, a virus, a viral protein, an enzyme substrate, a pharmacological agent, and a pharmacological agent candidate), each adapted to detect the desired predetermined protein if bound to the membranes.

In particular embodiments, the membranes provided in kits described herein include a porous substrate having a thickness of less than about 30 microns. Particular examples of such a kit include membranes that are polycarbonate membranes, especially polycarbonate membranes coated with a material for increasing the affinity of the membrane to biomolecules, for instance nitrocellulose, poly-L-lysine, or mixtures thereof.

III. Transfer Modes

Provided herein are multiple methods for transferring biomolecules from a sample that is generally substantially two-dimensional into one or more thin membranes, usually arranged in a stack. Several different specific transfer modes are provided. Some of these modes overlap, in that wicking or contact transfer can be used to transfer biomolecules from both tissue- and gel-based samples, and so forth. Even though perhaps not explicitly enumerated, all variations and combinations of the described methods are encompassed herein.

Wicking Transfer

In particular embodiments, a transfer liquid (such as a buffer) is passed through the membranes to encourage movement of the biomolecules from the sample to the membranes and through them. A distal or downstream wick may also be provided to help move liquid (such as the buffer) through the membranes in a desired direction of movement There is illustrated in FIG. 1 a perspective view of a representative disclosed membrane array transfer apparatus designated generally by reference numeral 10. Apparatus 10 includes a plurality of membranes 12 shown in a layered or stacked configuration such as array 13. While only about a dozen membranes are shown in array 13 of FIG. 1, it will be appreciated that many more membranes (e.g., 10, 50, 100 or more) may be employed depending on the number of targets sought to be identified, the quantity of biomolecules present in the sample, and the thickness of the material employed to construct membranes 12. Optionally, membranes 12 may be packaged in a suitable sealed enclosure or frame (not shown), for instance to maintain their integrity and/or prevent contamination.

Membrane array 13 is placed atop a stack of one or more sheets of blotting paper 14 that acts as a lower wick pulling buffer out of buffer chambers 18 though upper wicks 20 and membrane array 12 in the direction of the arrows shown in FIG. 1. A biomolecule trap 22 may be positioned intermediate membrane array 12 and blotting paper 14 to help the user ascertain whether and/or to what extent transfer has occurred.

In use and operation, apparatus 10 may be employed to create "carbon copies" or substantial replicas of the biomolecular contents of the sample applied to the stack. Membranes 12 are arrayed in a layered or stacked configuration as shown in FIG. 1 as reference numeral 13. In a particular embodiment, a substantially two-dimensional sample 11 (such as a conventional frozen tissue section as illustrated) is placed on a support substrate (e.g., a layer of polycarbonate) and then sandwiched between two slices of 2% agarose (not shown). The entire preparation is positioned adjacent to the membrane array 13. Buffer 16 is applied using buffer chambers 18 and upper wicks 20 to elute and transfer proteins from the frozen section. About 50–100 milliliters of buffer per square centimeter are used in each transfer with average length of the transfer being about 1–2 hours.

After transfer the membranes are separated and incubated with the detector antibody. Antibodies are selected based on the types of targets sought. Membranes are washed in a buffer and the protein/detector complex can be visualized using a number of techniques such as ECL, direct fluorescence, or colorimetric reactions. Commercially available flatbed scanners and digital imaging software can be employed to display the images according to the preference of the user.

The specific example illustrated in FIG. 1 shows a device and a method for detecting biomolecules in a tissue section 11 or other two-dimensional sample (e.g. an electrophoretic gel) by creating "carbon copies" (substantial copies that are not necessarily identical copies, they may have slight differences but can be identical or nearly identical) of the biomolecules eluted from the sample, and visualizing the biomolecules on the copies using antibodies or other molecules having specific affinity for the biomolecules of interest. Thin membranes 12 in a stacked or layered configuration are brought into contact with the sample and reagents, and reaction conditions are provided so that the biomolecules are eluted from the sample onto the membranes, whereupon the biomolecules can be visualized using a variety of techniques, as set forth herein.

Certain embodiments of the disclosure include a method of detecting an analyte in a biological sample using stacked contiguous layered membranes that permit biomolecules to move through a plurality of the membranes, while directly capturing the biomolecules on one or more of the membranes. Biomolecules from the sample are moved through the membranes under conditions that allow one or more of the membranes to directly capture the biomolecules, and biomolecules of interest are concurrently or subsequently detected on the membranes, for example by exposing the biomolecules of interest to a detector, such as a specific capture molecule (for example an antibody or a nucleic acid probe).

Alternatively, the biomolecule itself may be a detector (such as a nucleic acid probe) to which a sample is exposed. In this case, the biological sample is one or more purified nucleic acid probes placed in assigned locations on a surface of the stack, which are allowed to migrate through membranes (for example in a direction of movement transverse to the layers) to produce multiple substantial "copies" of the original probes in corresponding locations on the multiple membranes. The layers then can be separated and exposed to a target biological specimen, which may have nucleic acid molecules that hybridize to the probes.

In some examples, the biological sample is a tissue specimen that is placed on the stack of layered membranes, and biomolecules from the tissue specimen are directly captured by the membranes as the biomolecules move through the membranes. The membranes may, for example, be separated prior to detecting the biomolecules of interest, and the separated membranes are exposed to the detectors. Alternatively, the biological molecules of interest may be contained in a biological specimen to which the membranes are exposed. For example, the biomolecules directly captured by the membranes may themselves be nucleic acid probes or antibodies, and the membranes may be exposed to a biological specimen in which a nucleic acid or peptide (such as a protein) is to be detected.

Biomolecules detected on the membrane copies may be correlated with a biological characteristic of the sample. For example, a tissue specimen may be placed in a position on top of the stack, and a biomolecule of interest (such as a particular protein) may be detected in one of the membrane copies at a position that corresponds to the position in which the tissue specimen (or one of its substructures such as an organelle) was placed. The presence of that biomolecule in the tissue specimen can then be correlated with a biological characteristic of the sample. For example, a highly malignant tissue specimen may be found to contain a protein that may then be associated with the highly malignant phenotype of the specimen.

In particular examples, the method can be used to create a set of microarray substantial "copies" by applying a plurality of detectors, such as DNA probes, antibodies, or a combination thereof, to the stack of layered membranes. The stack of layered membranes provide a plurality of substrates through which the probes or antibodies (generally, detector molecules) move, and in which a portion of the probes or antibodies are directly captured by one or more of the substrates. The substrates can be subsequently separated to provide corresponding substrates having a plurality of DNA probes, antibodies or a combination thereof in corresponding positions of each of said substrates. The multiple membranes maintain a substantially coherent relationship between the probes and/or antibodies as they move through the substrate. This coherent relationship may or may not be a direct spatial correspondence, but the relative relationship between the biomolecules may be maintained in such a way that the identity of the biomolecules on the membranes can be known from the relationship in which the biomolecules were placed on the stack of layered membranes.

Contract Transfer

Figure 2A:
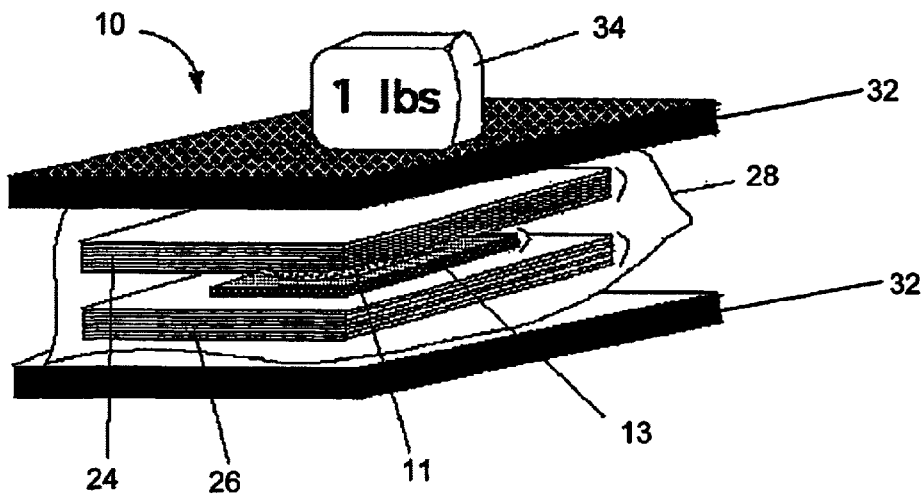
FIG. 2A is an oblique view of an apparatus shown transferring molecules from a tissue section onto a membrane stack.
Figure 2B:
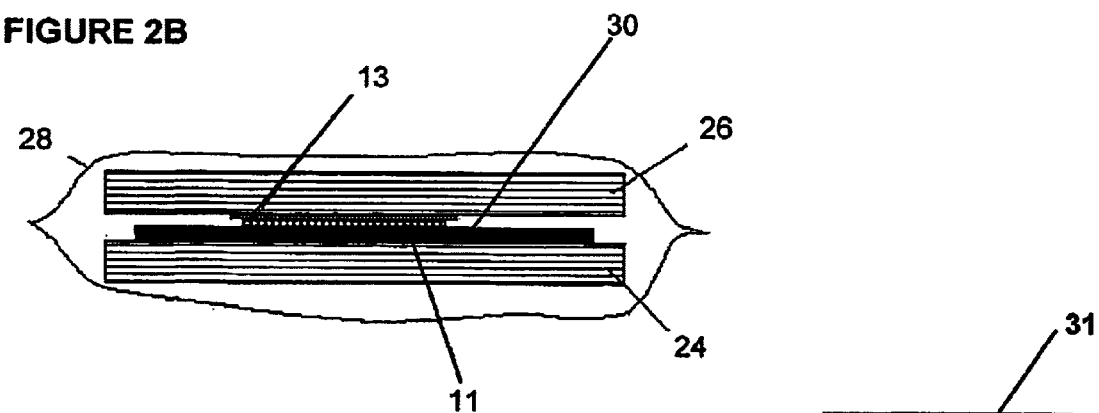
FIG. 2B is a front view of an assembled contact transfer stack, prepared for transfer in the apparatus illustrated in FIG. 2A.

There is illustrated in FIG. 2A an alternative embodiment of an apparatus 10 for transferring biomolecules from a substantially two-dimensional sample 11 onto a membrane stack 13, which stack in some embodiments is provided in the form of a kit Apparatus 10 generally includes a membrane stack 13 upon which a sample 11 (illustrated as a tissue section) may be placed, a pair of filter pads 24 and 26, and a fluid impervious enclosure 28, such as a plastic bag or the like. Optionally, the sample 11 (e.g., a tissue section) may be presented on a support 30 (as illustrated in FIG. 2B). In particular embodiments, the support 30 is a microscope slide or other fluid impervious support such as a piece of tape.

More specifically, in a first embodiment, membrane stack 13 comprises one or more membranes 12, for instance up to five membranes, generally constructed as described herein. The membranes 12 in stack 13 should have a high affinity for proteins and other biomolecules but have a low capacity for retaining such molecules. This feature permits the molecules to pass through the membrane stack with only a limited number being trapped on each of the successive layers, thereby allowing multiple "carbon copies" (substantial copies that are not necessarily identical copies, they may have slight differences but can be identical or nearly identical) to be generated. In other words, the low capacity allows the creation of multiple replicates as only a limited quantity of the biomolecules are trapped on each layer.

First and second filter pads 24, 26 are preferably constructed of a blotting paper such as GB004 Blotter Paper available from Schleicher and Schuell. Filter pads 24, 26 are saturated with a transfer buffer such as Tris or phosphate base buffers.

Enclosure 28 may comprise any collapsible, fluid impervious material adapted to envelop the sample 11, membrane stack 13, and filter pads 24, 26, which may be kit components. Enclosure 28 is preferably a plastic bag, such as a heat sealable pouch. By way of example, such a bag may be made of a resin, such as a polyester or other resin. In certain embodiments, enclosure 28 is a heat sealable pouch such as those available from Kapak Corp. (Minneapolis, Minn.).

Figure 3:
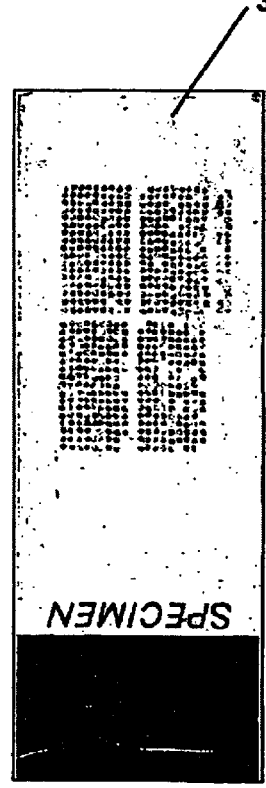
FIG. 3 is a photograph of a typical tissue microarray on a slide.

In use and operation, the sample 11 (e.g., a tissue section sample or tissue microarray 31, shown in FIG. 3) is positioned in contact with a face of a membrane stack 13 and both the sample and stack are placed between two filter pads 24, 26, which have been saturated with transfer buffer, to for an assembled contact transfer stack. The assembled contact transfer stack is placed inside fluid impervious enclosure 28, such as a plastic bag. The membranes are pre-wetted in the aforementioned transfer solution.

Fluid impervious enclosure 28 is placed between a pair of substantially flat surfaces 32, at least one of which also serves as a source of heat. By way of example, the pair of substantially flat surfaces 32 can be surfaces of a pair of heating elements such as those provided in gel dryers manufactured by Bio-Rad Laboratories (Hercules, Calif.). In other embodiments, the pair of flat surfaces 32 may be provided by MI Research devices, such as the PTC-200 Peltier thermal cycler, which provide a separate heated lid and a thumbwheel to adjust height and pressure of the lid and thereby provide pressure.

In embodiments where heat is applied only from one side of the assembled sample and stack, the heat is preferentially applied from the side of the sample rather than the membrane stack side, such that a heat gradient is created with the heat applied on the sample side.

To effect transfer, the bag and its contents are heated to a temperature of 60 to 95° C., in some embodiments 60 to 80°

C., or more particularly in some embodiments 70° C. The bag and its contents are heated for at least about an hour, and in some embodiments about two hours or more. Sufficient pressure is applied throughout the heating process to ensure that there is adequate contact between the sample and the membrane stack to facilitate transfer of biomolecules to the membrane stack. By way of example, such pressure can be applied using a weight 34 of 0.5 to 2 pounds, which may optionally be included as a kit component. Springs, clamps, or clips capable of applying pressure may be employed instead of a weight.

The combination of heat and pressure being applied causes biological components, including proteins and/or nucleic acids and/or carbohydrates and/or lipids, to be transferred from the sample 11 to membrane stack 13. This produces multiple copies or replicas of the biomolecular content of the tissue sample, due at least in part to the binding characteristics of the membranes.

To ensure that the binding capacity of the membranes is sufficiently low to prevent trapping of too much of the sample, in some embodiments the thickness of membrane substrate should be less than 30 microns, in some embodiments from 4 to 20 microns, and particular embodiments from 8 to 10 microns. The pore size of the substrate should be from 0.1 to 5.0 microns, in particular embodiments 0.4 microns. Another advantage of using such a thin membrane is that is lessens the phenomenon of lateral diffusion. The thicker the stack of membranes, the wider the diffusion of biomolecules moving through the stack.

The substrate includes a coating on its upper and/or lower surfaces to increase specific binding of the proteins or other targeted biomolecules. The coating in certain embodiments is nitrocellulose, but other materials such as poly-L-lysine may also be employed.

Tissue section sample 11 may be derived from fresh/frozen tissue or tissue that has been fixed in formalin (or another fixative) and paraffin embedded tissue. The section is created by conventional methods, for instance using a microtome. The thickness of a tissue section can vary from 3 to 30 microns depending on the desired number of membrane replicates to be created. As a rule of thumb, the thickness of the section should be one micron for each replicate sought. Thus, for example, a 10 micron section would be used to create ten membrane copies.

As used herein "tissue" means any material containing cells, proteins, or nucleic acids including plant, animal, and human material. In lieu of tissue section sample 11, a tissue microarray 31 (FIG. 3) may be employed. Tissue microarrays are described in Kononen et al, *Nature Medicine,* 4:844–847, 1998) and are provided by several commercial entities, such as the Vast Array™ tissue arrays available from Research Genetics (Huntsville, Ala.). Tissue macroarrays are similarly constructed, except that they contain tissue sections that are generally larger than microarray samples; the tissue samples used in tissue macroarrays may optionally be dissected by hand. Alternately, in some embodiments the biomolecules on a gel (e.g., an electrophoretic gel) or other substantially two-dimensional sample are transferred to a membrane stack using similar methods, in place of tissue section 14.

Gel-Based Transfer

The most widely used method for identifying and measuring biological molecules is gel electrophoresis, a collection of techniques for separating or resolving molecules in a mixture under the influence of an applied electric field based on (usually) the difference in their size and/or charge. Electrophoretic separation is most commonly performed using porous polymer gels. During one-dimensional electrophoresis, a mixture of proteins is applied to a gel and exposed to the flow of an electric current. Since smaller proteins migrate faster through the gel than larger ones, separation based on their size is achieved. By way of example, this one-dimensional approach can only generate about 100 distinct protein bands, which is inadequate for many applications since the estimated number of proteins expressed in a typical mammalian cell is between about 10,000–15,000 proteins.

In order to improve the resolving power of electrophoresis gels, a two-dimensional gel technique was introduced in the 1970s, wherein electrophoretic separation of the proteins based on their size is preceded by charge-based separation. Isoelectric focusing (IEF) electrophoresis, which separates proteins according to their charge (pH), is run in one direction and mass separation is carried out in a perpendicular direction. Such two-dimensional (2-D) gel electrophoresis (often abbreviated as "2-D PAGE," for two dimensional polyacrylamide gel electrophoresis) has become the backbone of proteomics. The technique is routinely employed for characterizing the proteome of different classes of tissues, cells, cell lysates, body fluids or exudates. The end result of 2-D PAGE is the production and separation of various protein "spots" in a two dimensional Cartesian plane where the coordinates of each spot are represented by charge and molecular weight. However, the major challenge of 2-D electrophoresis is the identification of the proteins after they have been separated on the gel.

Proteins that have been separated on gels are usually identified, detected, and analyzed by one of several different techniques. If the protein spot represents an unknown protein, the most common approach is to physically remove or excise the spot from the gel, digest it with an enzyme, and characterize the protein by mass spectroscopy. A computer generates a plot of protein fragments according to their mass, and this plot serves as a fingerprint that may be used to facilitate the identification of the original protein. As in the analysis of actual fingerprints, the ability of mass spectroscopy to identify a detected protein relies on the prior recovery and analysis of a reference protein whose fragments match those of the detected protein. The identification of a truly new protein by mass spectroscopy remains a significant challenge.

Although mass spectroscopy provides the most incontrovertible data, the method is time consuming, expensive and cannot be accomplished in the absence of expensive core facilities and highly trained personnel. Furthermore, the technique is used only to analyze the proteins that can be stained with a ubiquitous stain such as Coomassie blue. Unfortunately, ubiquitous stains are not sensitive and permit only a small fraction of the proteins in the sample to be visualized. In other words, mass spectroscopy of ubiquitously stained gels does not yield a broad "dynamic range" as it fails to identify certain low abundance—but potentially important—proteins. Among the low abundance proteins that may be left behind by these techniques are tyrosine kinases, cytokines, and transcription factors, which play a key role in many diseases.

An alternative approach to identifying gel separated proteins is immuno-blot analysis, which uses a detectable antibody specific to a protein of interest in lieu of a ubiquitous stain. The proteins are transferred onto a membrane, typically constructed of either nitrocellulose or of polyvinylidene difluoride (PVDF) and antibodies are applied to the membranes. Immuno-blotting is rapid and can be accomplished in less than a day. Also, it is estimated to be about 1000-fold more sensitive than Coomassie blue staining, allowing even low abundance proteins to be identified. It is significantly more specific as well. However, a key limitation of immuno-blotting is that at most only a handful of proteins can be identified on a single blot due to overlapping spots and cross-reactivity with different proteins in the sample. Since the 2-D gel process requires approximately 24 hours to complete, it would be prohibitively time consuming to create enough immuno-blots to identify the large quantity of proteins needed for most proteomics applications.

Thus, there is a clear need to develop techniques that permit large numbers of proteins across a wide dynamic range to be identified in parallel. Information potentially relevant to attempts to address this need can be found in the following references: Sanchez et at, *Electrophoresis*, 18:638–641, 1997; Neumann & Mullner, *Electrophoresis*, 19:752–757, 1998; Manabe et al., *Annal. Biochem.*, 143:39–45, 1984; Legocki & Verma, *Annal. Biochem.*, 111:385–345, 1981; and PCT International Publication No. WO00 045168, all herein incorporated by reference.

However, each of the techniques described in these references suffers from one or more of the following disadvantages: (i) not sensitive enough to detect low abundance proteins, (ii) cannot identify large numbers of proteins in a high-throughput manner, and (iii) requires specialized or sophisticated hardware that leads to loss of protein and a decrease in the resolution the protein spots during the transfer.

According to methods provided herein, biomolecules that have been electrophoretically separated on a gel, or via chromatography, etc. are transferred from the gel onto a stack of membranes. Examples of such membranes are membranes that are constructed and chemically treated to have a high affinity but low capacity for proteins. Suitable membranes and methods for their construction and preparation are described herein. The use of such membranes allows the creation of multiple replicates of the protein content of the gel.

The membranes are then incubated with a unique ligand species (a detector molecule) or mixture or cocktail of such, to assist in and permit detection and/or analysis of biomolecules on the membranes. The membranes are generally separated one from another prior to such incubation. Detector molecules/ligands can be any of a number of molecules that have binding specificity for a target molecule of interest, and include antibodies (such as monoclonal antibodies), antibody fragments (e.g., FAB, F(AB)$_2$, single chain antibodies, receptor proteins, solubilized receptor derivatives, receptor ligands, metal ions (particularly paramagnetic or radioactive ions), viruses, viral proteins (e.g., human rhinovirus or proteins thereof that bind to ICAM-1, or HIV or proteins thereof that bind to CD44), enzyme substrates, toxins, toxin candidates, pharmacological agents, pharmacological agent candidates, other small molecules that bind to specific proteins, as well as molecules that bind or hybridize to nucleic acids (e.g., nucleic acid probes or specific binding proteins or fragments thereof) etc. While each membrane has essentially the same pattern of biomolecules bound to it, different combinations of such biomolecules can be detected on each membrane due to the particular ligand or cocktail of ligands selected to corresponds to the particular layer.

The nature of the species of ligand(s) in the cocktail provided to the membrane determines the nature of information that can be obtained from that membrane. For example, by incubating a membrane with an antibody or antibody fragment, one is able to identify the presence or absence of protein molecules of the sample that bind to such molecules. In this way, for example, a membrane could be incubated with an antibody that specifically binds a protein kinase, in order to determine whether a particular protein is a protein kinase, or possesses an epitope that mimics that of a protein kinase. Similarly, by employing as the ligand, a cellular receptor protein, solubilized receptor derivative, or receptor ligand, the membrane would enable one to identify whether a particular protein was a receptor or receptor ligand. Since viruses and other pathogens are capable of binding to cellular receptor proteins, a cocktail containing a virus or viral protein could be employed in the same manner as a receptor ligand to identify whether a particular protein was a cellular receptor or receptor ligand. In an alternative embodiment, the cocktail could comprise one or more pharmacological agents to identify proteins that interact with such agents. Likewise, pharmacological agent candidates could be incubated with the membranes, thereby revealing the ability of such candidate molecules to bind to specific proteins. For example, an acetylcholinesterase inhibitor or a monoamine oxidase inhibitor (MAOI) could be incubated with a membrane to identify proteins that bind the inhibitor and which thus might be additional therapeutic targets of the inhibitor. Likewise, a compound suspected of possessing therapeutic potential could be incubated with a membrane to reveal whether it binds to proteins expressed, for example, in the liver or kidney, thereby revealing its potential to treat diseases affecting these organs. Examples of the methods and kits permit the further analysis of such binding to determine, for example, whether such proteins are expressed in other organs and tissues (e.g., the brain).

In one embodiment, a membrane will be incubated in the presence of a single ligand, or a cocktail of different ligands of the same class of ligands (e.g., antibodies, receptors, hybridizing probes, etc.). Alternatively, a membrane may be incubated with different classes of ligands. For example, a membrane that is incubated with antibodies that bind protein kinases and with a therapeutic candidate, can be employed to reveal therapeutic candidates that bind to protein kinases. Where mixtures or cocktails of ligands are employed, the cocktails are preferably formulated so that no two ligands bind overlapping or adjacent protein spots. Thus, for example protein spots that are too close together to be discriminated on a single membrane may be detected on separate membranes.

In an alternative embodiment, the ligand is permitted to bind to proteins of the sample prior to the transfer to a membrane. Thus, in some examples the ligand is provided to a living or deceased subject, to a tissue or cell, to a tissue or cell preparation, or to a tissue or cell extract, prior to the fractionation or separation of protein. The proteins are then transferred to membranes and the proteins and ligand are visualized. In such an embodiment, one can detect whether binding between a ligand and a protein of the sample and occurs in situ, and/or under physiological conditions. Optionally, the membranes can be incubated in the presence of additional ligand (which may be the same or different from the initially employed ligand) in order to detect competition between or among ligands for binding sites, to evaluate the avidity of binding, to examine binding complexes of three or more molecules, etc.

Figure 4A:
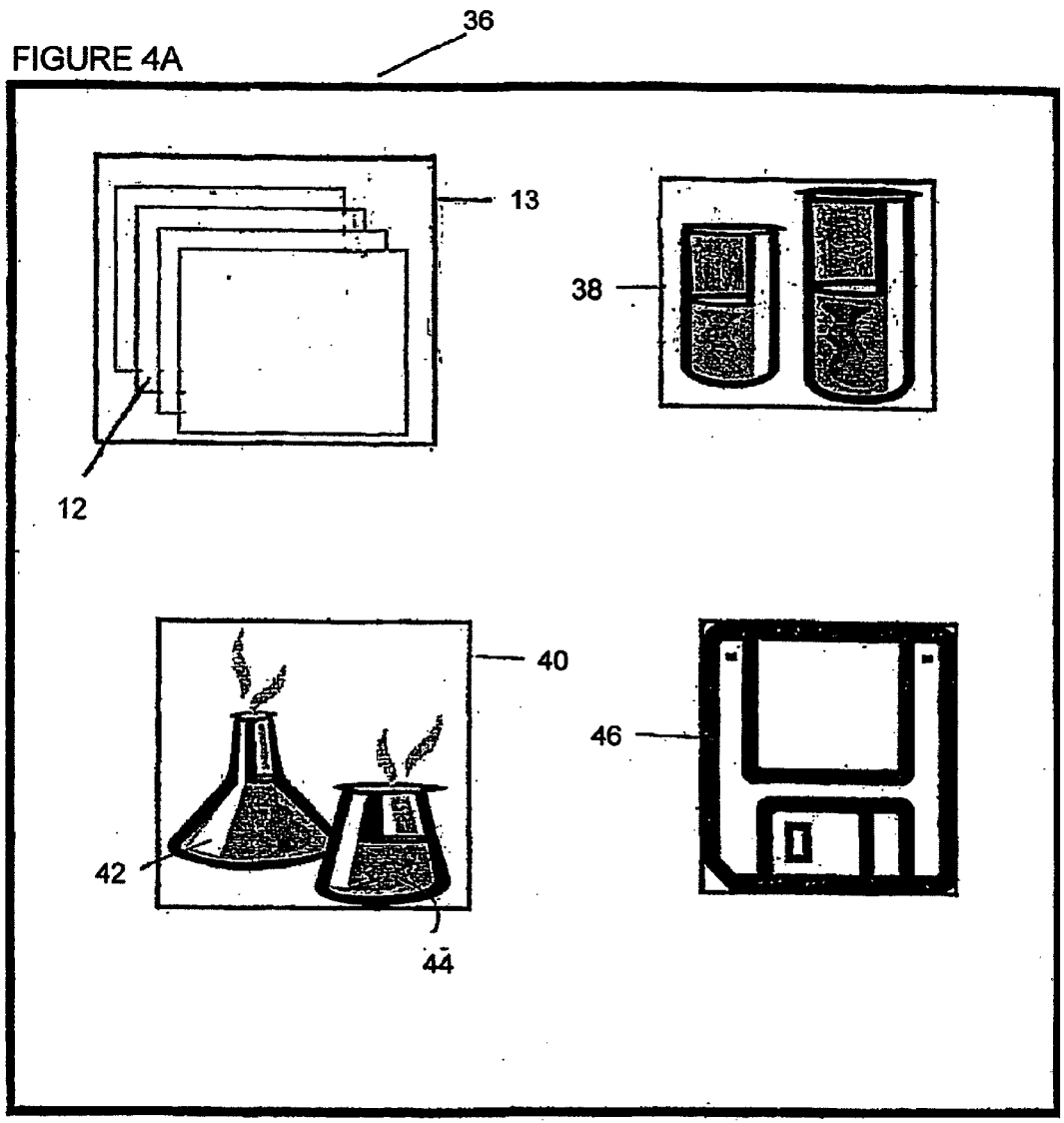
FIG. 4A is a schematic illustration showing the components of a kit according to one embodiment

Particular embodiments provide a method and a kit 36 for identifying (i.e. detecting, annotating, and/or characterizing) groups of proteins (not shown) that have been separated by gel electrophoresis. As illustrated in FIG. 4A, in one example kit 36 generally comprises the following components: (i) a stack of membranes 13 upon which the proteins are transferred, (ii) primary antibody cocktails 38, for instance one for each of the membranes 13, and (iii) other reagents 40 including (as in illustrated in kit 36) protein transfer buffer 42 and antibody detection chemistries 44. The kit 36 may also include software 46 that allows the user to analyze and manipulate the images produced so as to yield a "proteomic image" of the biological sample being tested and compare it to proteomic images from other samples in a database. Alternatively the software may be acquired or accessed independent of the kit In a specific embodiment, and with reference to FIG. 4A, membrane stack 12 comprises a plurality of membranes 13 adapted to be removably stacked atop one another, as shown.

Figure 5:
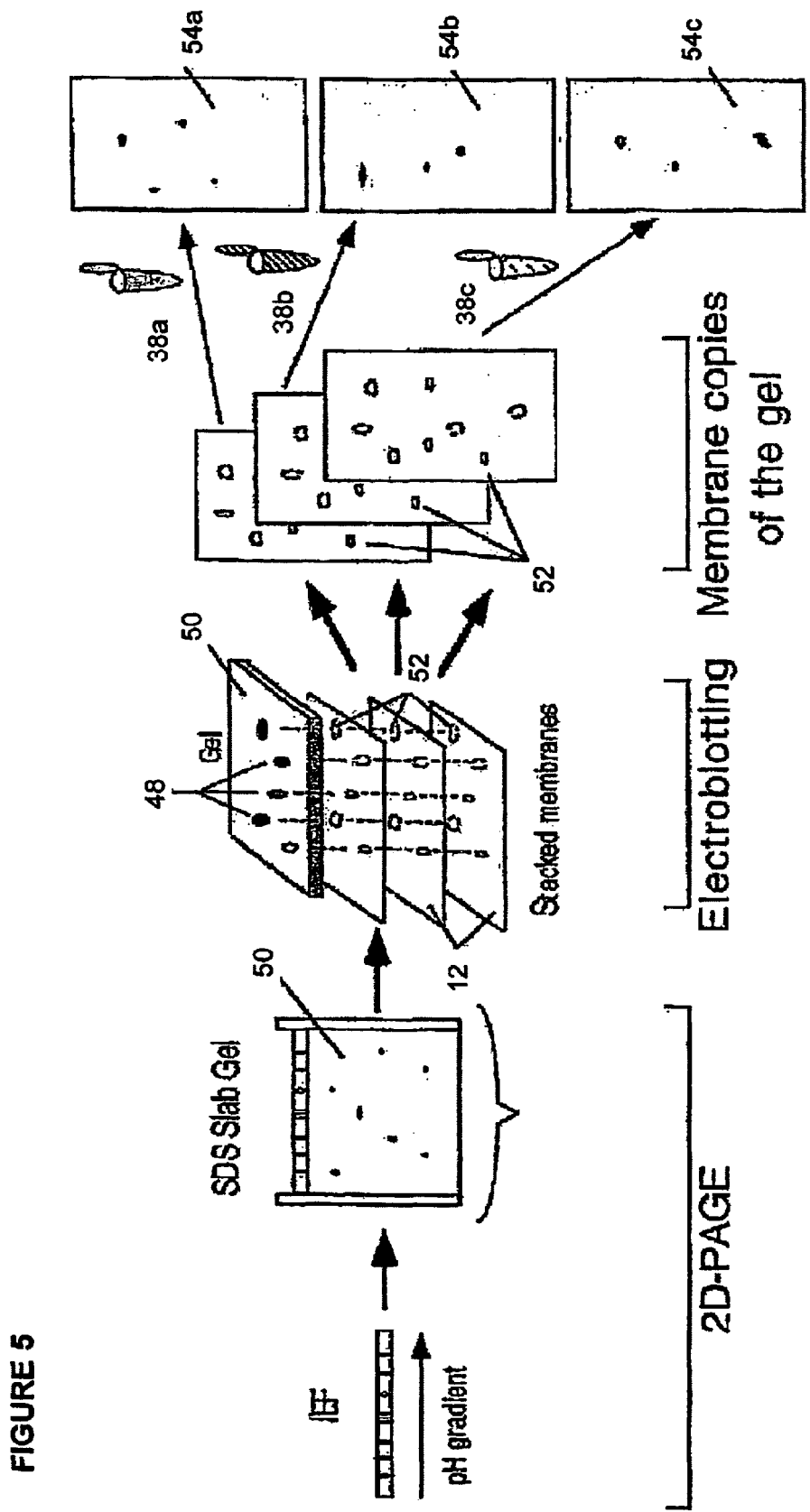
FIG. 5 is a schematic illustration showing a method according to one provided gel-transfer embodiment.

According to the method of a particular embodiment (as illustrated in FIG. 5), proteins 48 that have been electrophoretically separated on gel 50 are transferred from the gel through membrane stack 13. This allows the creation of multiple replicate blots 52 of the protein content of the gel. The membranes are then separated and each is incubated with one of the unique cocktails 38(a–c) of ligands, e.g., antibodies. The antibodies employed are labeled or otherwise detectable using any of a several techniques such as enhanced chemiluminescence (ECL). This produces unique spot patterns 54(a–c) on each of the membranes. The membranes with unique spot patterns 54 are then scanned or digitally imaged using an imaging instrument (not shown) so that the density of the spot may be calculated, compared to other samples, and displayed on a computer using software 46, as described herein.

One advantage of specific embodiments provided herein is that they provide a third dimension of protein separation for a biological sample, one additional dimension from the size and charge separations obtainable from 2-D gels. The layered membranes provide a cost-effective tool for selecting groups of compatible antibodies that can be used to detect subsets of proteins on the same membrane. Once selected these ligand combinations can be packaged in a kit and used repeatedly for the controlled analysis of proteomes displayed on stacked membranes. Since 15–20 replicates or copies can be generated from a single gel and ten or more ligands can be applied to each membrane several thousand different proteins can be identified from a single gel according herein described methods.

Since ligands can be used to detect many post-translational modification of proteins (e.g. phosphorylation) the present disclosure can be employed to identify protein function as well as structure.

Although these embodiments have been described with respect to 2-D gels, it is also contemplated that the methods and devices described can be employed with one dimensional gels (e.g., as for the identification of transcription factors separated by a gel-shift assay), or proteins may be separated from other proteins of a sample, by other means, as by chromatography. It is also contemplated that these methods can be used to generate duplicate copies of non-protein biomolecules, such as nucleic acids, lipids, sugars (such as polysaccharides) and combinations or complexes of two or more types of biomolecules.

In certain embodiments, buffer reagent for eluting proteins from a gel to a membrane stack comprises a mixture of glycine, methanol, and SDS as described herein. For 1-D gel analysis, protein staining can be carried out using FastBlue Stain (Chemicon).

Bi-Directional Transfer

In alternative embodiments of the provided methods, the sample from which biomolecules are to be transferred is not supported by an impervious support and the sample is placed between members of the membrane stack. Thus, in such embodiments one or more membranes is placed adjacent to each of two faces of the substantially two-dimensional sample, and transfer of the biomolecules from the sample to the membranes occurs in two directions (bi-directional transfer).

Figure 6:
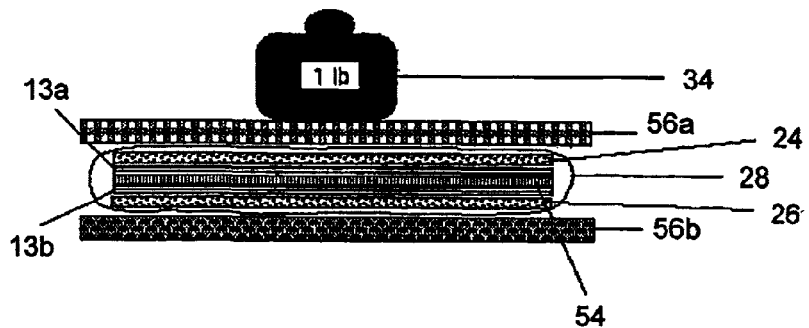
FIG. 6 is a sectional view of a stack of membranes shown operatively engaged with an apparatus to transfer proteins from a gel onto the membranes.
Figure 7A:
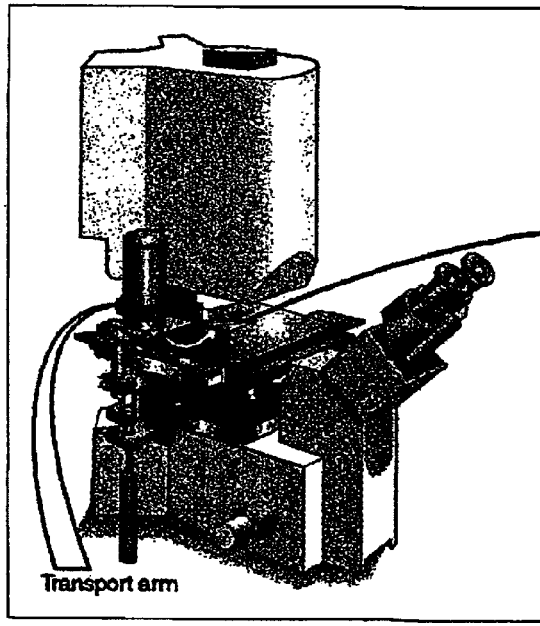
FIG. 7A is a perspective view of a typical prior art LCM instrument.
Figure 7B:
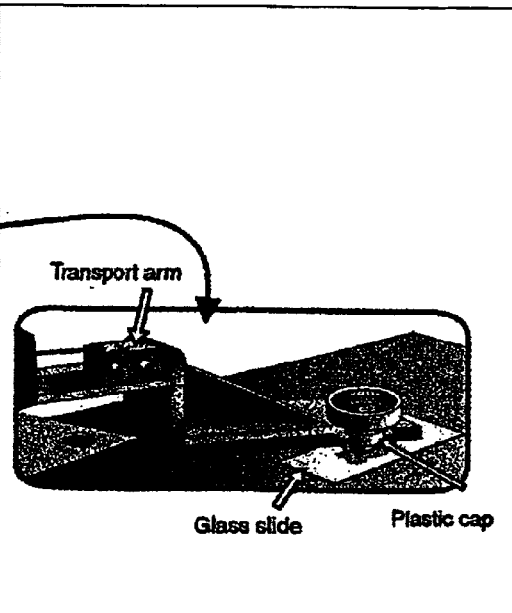
FIG. 7B is an enlarged perspective view of an LCM cap shown engaged with a glass slide via a transport arm.
Figure 7C:
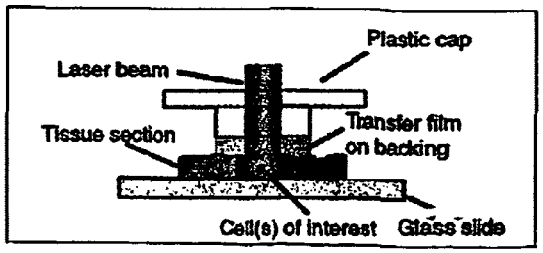
FIGS. 7C and 7D are side elevation views showing the transfer of cellular material from a tissue section on a glass slide to an LCM cap.
Figure 7D:
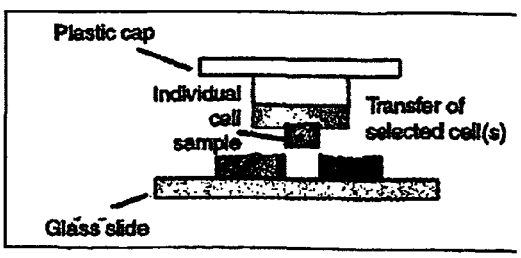

By way of example, this technique is illustrated schematically in FIG. 6. Here first and second membrane stacks 13a and 13b sandwich gel slab 54, which contains sample 11. A pair of filter pads 24 and 26, preferably constructed of a blotting paper such as GB004 Blotter Paper available from Schleicher and Schuell are provided adjacent to the membrane stacks as shown. Filter pads 24 and 26 are saturated with a transfer buffer such as TRIS or phosphate base buffers.

A collapsible, fluid impervious enclosure 28 is provided to envelop the pads, membrane stacks, and gel as shown in FIG. 7. Enclosure 28 (which in some instances is a plastic bag) is preferably a heat sealable pouch/bag such as those available from Kapak Corp. (Minneapolis, Minn.). Preferably, most of the air is removed from enclosure 28 by gentle squeezing and/or vacuum suction and it is sealed by a heat sealer such as the Impulse Sealer (American International Electric). Enclosure 28 is then placed between a pair of heating elements 56a and 56b such as those provided in Gel Dryers manufactured by Bio-Rad Laboratories (Hercules, Calif.). The enclosure 28 and its contents are optionally heated to a temperature of between about 50 to 90° C., preferably to about 80° C. for about 2–4 hours. In some embodiments, pressure is applied throughout the heating process using a weight 34.

The heat and pressure applied to contents of the enclosure permit proteins and other molecules to be transferred from the gel or other two-dimensional sample to the membrane stack. This produces multiple copies or replicas of the biomolecular content of the sample.

Transfer from Laser Capture Microdissection Samples

Under the microscope, tissues are heterogeneous, complicated structures with hundreds of different cell types locked in morphologic units exhibiting strong adhesive interactions with adjacent cells, connective stroma, blood vessels, glandular and muscle components, adipose cells, and inflammatory or immune cells. In normal or developing organs, specific cells express different genes and undergo complex molecular changes both in response to internal control signals, signals from adjacent cells, and humoral stimuli. In diseased tissues the cells of interest, such as pre-cancerous cells or invading groups of cancer cells, are typically surrounded by these heterogeneous tissue elements. Cell types undergoing similar molecular changes, such as those thought to be most definitive of the disease progression, may constitute less than 5% of the volume of the tissue biopsy sample. Therefore, a need arose to "microdissect" diseased cells from surrounding normal cells to permit molecular analysis of disease lesions in actual tissue.

To address this need researchers at the U.S. National Institutes of Health developed a technique known as "Laser Capture Microdissection" ("LCM") for procuring pure cells from specific microscopic regions of tissue sections. See Emmert-Buck, et al., *Science* 274:998–1001,1996; Bonner, et al., *Science* 278:1481–1483,1997, incorporated herein in their entirety. LCM allows small groups of cells to be isolated from tissue sections thereby allowing an investigator to collect only cells of interest so as to achieve high purity of the sample. Once collected, cells are homogenized and genomic DNA, total cellular RNA or total proteins can be isolated. Details of LCM are described, for example, in PCT International Patent Applications publications WO 09917094A2 and WO 098352A1, which are incorporated herein and are illustrated in FIG. 7.

In short, a laser beam focally activates a special transfer film which bonds specifically to cells identified and targeted by microscopy within the tissue section. The transfer film with the bonded cells is then lifted off the thin tissue section, leaving all unwanted cells behind (which would contaminate the molecular purity of subsequent analysis). This allows multiple homogeneous samples within the tissue section or cytological preparation to be targeted and pooled for extraction of molecules and analysis.

In order to simplify the process of handling the transfer film, the film may be permanently bonded to the underside of a transparent vial cap, such as those available from Arcturus Engineering Inc. (Mountain View, Calif.). After the targeted cells are transferred to the cap surface the cap is placed directly onto a centrifuge tube to extract biomolecules from the cap and purify biomolecules for subsequent analysis, for instance using electrophoresis gels, DNA microarrays and the like.

Unfortunately, many molecular biology assays such as Western blotting are difficult to perform on LCM-collected samples since the amount of material collected per unit of time is very small. While analysis of nucleic acids from LCM collected material is aided by the amplification techniques such as the polymerize chain reaction (PCR), protein amplification is not possible. Proteomics studies on LCM collected samples are thus particularly difficult.

Another current limitation of LCM is that different cell subtypes (e.g. epithelium and connective tissue) must be transferred to different caps. Since the biomolecules (proteins and nucleic acid) are removed from the cap for further analysis, different cell types cannot be mixed on the same cap since it could not be determined from which cell type a particular biomolecule originated. Thus users of LCM typically must process a different cap for each cell type in a tissue section, a procedure that is time consuming and creates variability in experimental design.

Embodiments provided herein include methods and apparatuses for detecting and analyzing biomolecules in a sample collected by LCM by eluting biomolecules away from the sample and binding them to one or more membranes in a layered or stacked configuration, then visualizing the biomolecules on the membranes.

In general, cellular samples embedded in/on an LCM transfer film or the like are positioned adjacent to a stack of one or more membranes, and reagents and reaction conditions are provided so that biomolecules are eluted from the cellular sample and transferred onto the membrane(s). Biomolecules on the membrane are then detected and visualized using one or more detector molecules, for instance antibodies or DNA probes having specific affinity for the biomolecules of interest.

Figure 8:
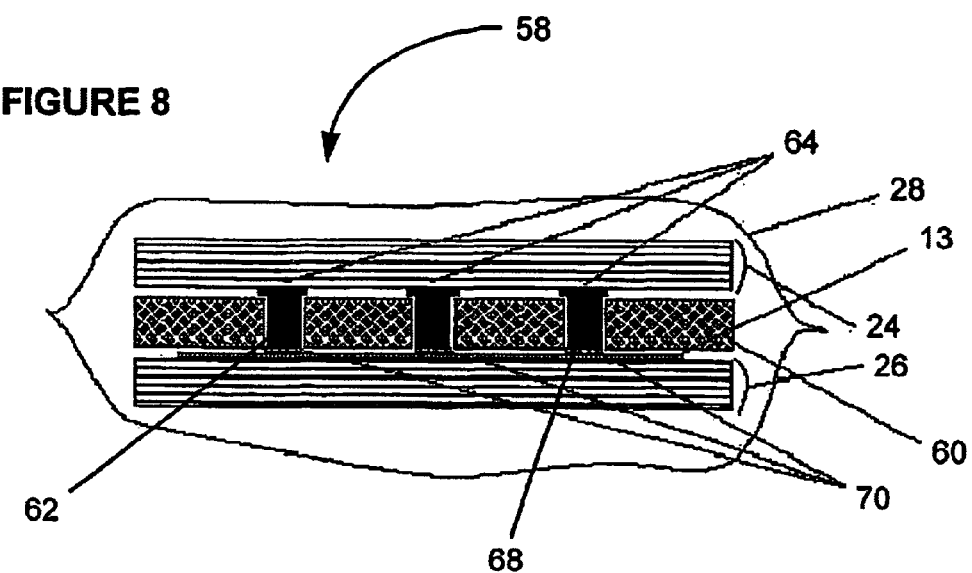
FIG. 8 is a longitudinal section view of one embodiment, in which LCM samples have been prepared for transfer through a membrane stack.

There is illustrated in FIG. 8 a longitudinal section view of one embodiment, preferably in the form of a kit, designated generally by reference numeral 58. Kit 58 generally comprises a membrane stack 13, LCM cap holder assembly 60, a pair of filter pads 24 and 26, and a fluid impervious enclosure 28 such as a plastic bag or the like.

In some embodiments, membrane stack 13 comprises up to 20 membranes, generally constructed as described herein. Representative membranes 12 in stack 13 have a high affinity for proteins and other biomolecules, but have a low capacity for retaining such molecules. In another embodiment, a single membrane is used in lieu of a plurality of membranes. If only one membrane is used it need not have the low capacity requirements of certain other embodiments, and it can be constructed of any of a variety of materials conventionally employed as blotting membranes, such as nitrocellulose or PVDF.

Figure 10A:
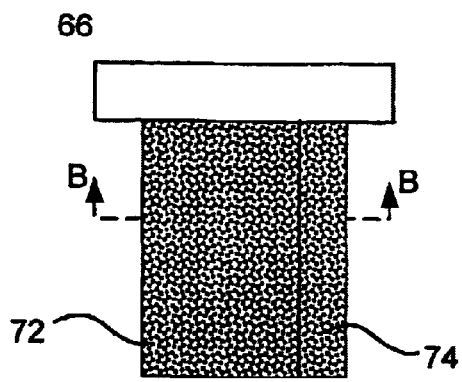
FIG. 10A is a side elevation view of a modified LCM cap according to provided embodiments.

LCM cap holder assembly 60 is preferably constructed of a heat conductive material such as metal and has generally rectangular dimensions. A plurality of apertures 62 are defined by cap holder assembly 60 with each aperture adapted to receive a standard LCM cap 64 such as those available from Arcturus Engineering, Inc. (Mountain View, Calif.) or a modified LCM cap 66 (FIG. 10). Mounted to caps 64 (or 66) is a standard LCM transfer film 68 having adhered thereto the selected cellular material 70 that serves as the transfer sample 11 from the tissue sample following an LCM procedure. By way of example, LCM is performed on tissue sections (such as frozen or fixed/paraffin embedded sections) using the equipment such as that illustrated in FIG. 7 according to known methods, such as those recommended by Arcturus Engineering, Inc.

First and second filter pads 24, 26 are preferably constructed of a blotting paper such as GB004 Blotter Paper available from Schleicher and Schuell. Filter pads 24, 26 are saturated with a transfer buffer such as Tris or phosphate base buffers.

Enclosure 28 may comprise any collapsible, fluid impervious material adapted to envelop the other kit components. Plastic bag 28 is preferably a heat sealable pouch such as those available from Kapak Corp. (Minneapolis, Minn.).

After microdissection, caps 26 can be stored frozen until transfer of the molecules is desired. Cellular material 70 embedded within transfer film 68 is hydrated through gradient of ethanol and optionally mildly digested with proteases. Caps 64 (or 66) are then inserted within apertures 62 defined in cap holder assembly 60 and the cap holder is placed adjacent to membrane stack 13 so that the transfer film 68 is in direct contact with a membrane. First filter pad 24 is placed above cap holder assembly 62 and second filter pad 26 is placed below membrane stack 13. (Both pads are soaked in a transfer buffer.) Pads 24 and 26, sandwiching the other components of the assembled stack of kit 58, are placed within enclosure 28. Most of the air is removed from enclosure 28 by gentle squeezing and/or vacuum suction and it is sealed by a heat sealer such as the Impulse Sealer (American International Electric).

Figure 9:
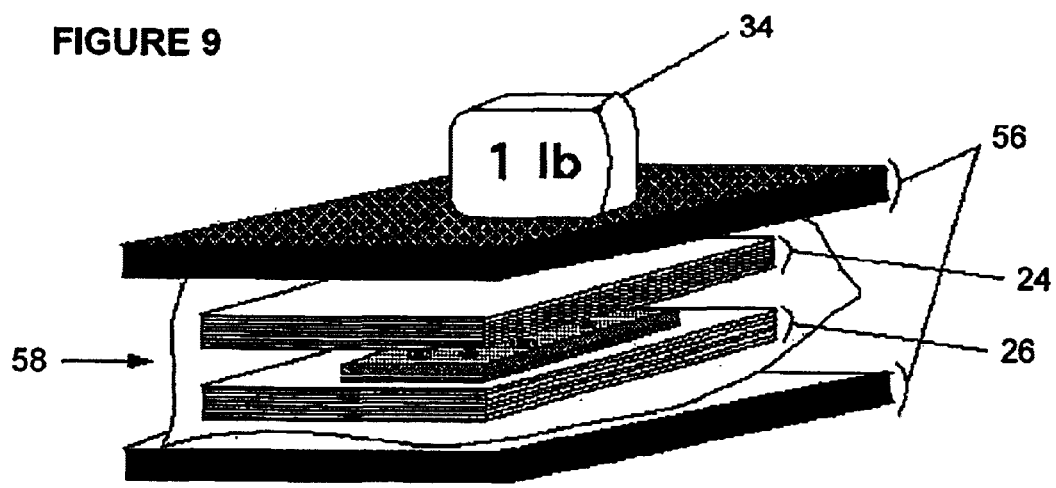
FIG. 9 is perspective view of one LCM transfer embodiment, shown in use and operation.

With reference to FIG. 9 plastic bag 28 is placed between a pair of heating elements 56 such as those provided in Gel Dryers manufactured by Bio-Rad Laboratories (Hercules, Calif.). The bag and its contents are heated to a temperature of between about 60 to 80° C., preferably to about 70° C. for about two hours. Pressure is applied throughout the heating process using a weight 34, which may optionally be added as a kit component.

In other embodiments, multiple caps are created from a single cell type and the biomolecules (proteins and/or nucleic acids) are transferred to the single membrane or membrane stack in the manner described herein. One membrane (or more) can then be cut into pieces corresponding to the number of caps so that the biomolecular content from each cap may be separately incubated with a different detector molecule or detection system.

Figure 10B:
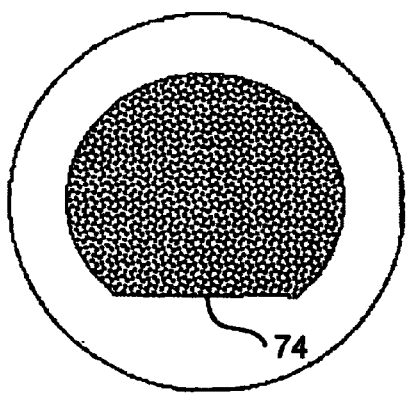
FIG. 10B is a section view taken along line B—B of FIG. 4A.

It may be desirable to prevent rotation of the LCM caps during the transfer process so that positions of the cellular samples remain fixed relative to the membranes. This would be useful when particular regions of the film 68 are allocated to particular cell types (e.g. epithelium vs. connective tissue or diseased vs. normal cells). By preventing rotation of the LCM caps the user can correlate the position of the biomolecules on the membranes with the region of film 68 and cell type from which the biomolecules originated. Lines or other indicia (not shown) may be provided on the membranes and caps 64 to aid the user in this process. In order to prevent rotation, the standard LCM cap may be modified as shown in FIG. 10. Modified cap 66 has a shank portion 72 that defines a flat surface 74 (shown in FIG. 10B) that is adapted to engage an similarly shaped aperture in the LCM cap holder assembly (not shown). The size of cap 66 and corresponding transfer film may be enlarged so that cells of interest from an entire tissue section may be microdissected or otherwise transferred onto a single cap, thereby saving time and reducing experimental variability as compared to using different caps for each cell type as is the practice currently in use.

"Microarray" Transfer

Another use of the membrane arrays provided herein is to make multiple copies of a cDNA or other microarray in a manner that is less expensive and labor-intensive than robotic systems. In particular embodiments, the plurality of DNA probes, antibodies, or combination thereof, is applied to the stack of membranes from a plate having a plurality of wells (e.g., a microtiter or like plate), each containing a different DNA probe or antibody. The DNA probes or antibodies are transferred from the wells to the stack so as to create a set of substantially replicate microarrays.

Figure 11:
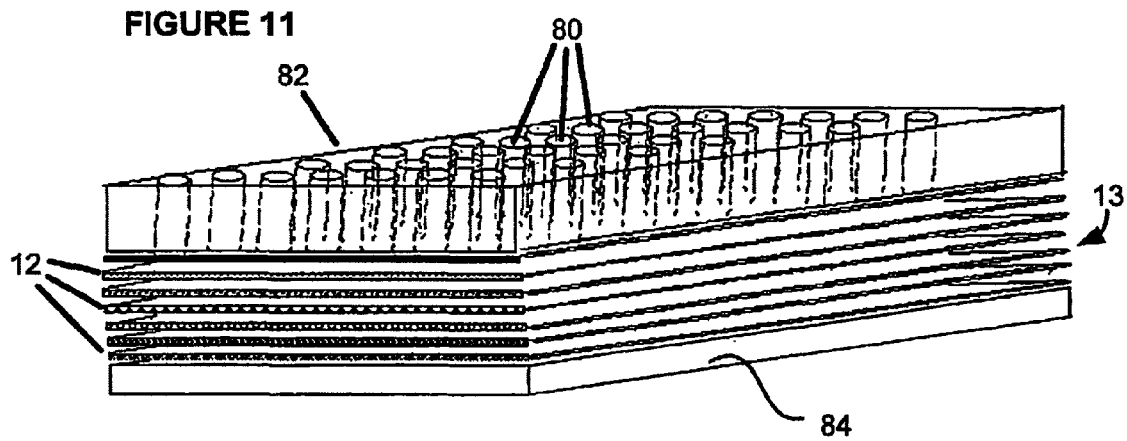
FIG. 11 is a perspective view of a transfer array shown in use with a microtiter plate.

With reference to FIG. 11, DNA sequences representing different genes are placed into individual microtiter wells 80 of a microtiter plate 82 (e.g. a 96-well plate). The microtiter plate 82 is placed adjacent to a stack 13 of membranes 12, to allow the contents of the microtiter wells 80 to be transferred from the respective wells to the stack of membranes 13. In the illustrated embodiment, contents of the wells are transferred from the wells 80 to a top surface of the stack of membranes 13, so that the contents are applied in a pattern that corresponds to a pattern of the wells.

The DNA is transferred through the membranes in a direction of movement from the wells toward a wick member 84, and the spatial orientation of the samples is maintained. Because of the high affinity, low capacity characteristics of membranes 12, as the nucleic acids traverse the capture membrane stack 13, a small percentage of DNA hybridizes to each membrane, creating a series of replicate copies, each one containing a grid of DNA spots that match the orientation of the DNA samples in the microtiter plate. Thus, a set of cDNA arrays may be created in a very rapid and inexpensive fashion. Antibody and tissue lysate arrays can also be created by this method.

IV. Types of Samples

Any two-dimensional sample material that contains releasable biomolecules can be used as a source of biomolecules in the provided transfer processes. By "two-densional" it is meant that the material is, or can be formulated so that it is, substantially flat and relatively thin. Representative examples of substantially two-dimensional samples include tissue samples such as thin section slices (e.g., archival or frozen tissue samples), tissue arrays, cDNA or other nucleic acid microarrays, protein microarrays, 1-D protein gels, 1-D nucleic acid gels, 2-D protein gels, and so forth.

It is further contemplated that the described transfer methods, arrays, and devices can be used in forensic procedures to detect and study biological material such as bodily fluids; to detect biological (e.g., microbial) contamination of food or other substances; and so forth. In order to provide the sample in a substantially flat and thin format, substances may be suspended in a liquid or gas, then run through and optionally affixed to a filter such as a sheet of filter paper, with the filter then used as the transfer sample. By way of example, a soil sample or fluid sample could be so prepared for transfer. Some substances may be compressed into a substantially flat form, for instance by rollers or another spreading mechanism; by way of example, a food sample (e.g., ground meat) could be so prepared. Generally these samples can be referred to as structurally transformed samples, because their format is altered to render them substantially two dimensional prior to transfer onto a membrane stack.

Embodiments provided herein may be used to identify biomolecules (e.g., proteins or nucleic acids) in any biological sample including bodily fluids (e.g. blood, plasma, serum, urine, bile, cerebrospinal fluid, aqueous or vitreous humor, or any bodily secretion), a transudate, an exudate (e.g. fluid obtained from an abscess or any other site of infection or inflammation), fluid obtained from a joint, and so forth. Additionally, a biological sample can be obtained from any organ or tissue (including or autopsy specimen) or may comprise cells.

V. Membranes

Also provided herein are membranes, which can be used in the described methods of biomolecule separation.

In particular embodiments, the membranes comprise a material that non-specifically increases the affinity of the membranes to the biological molecules (or a class of biomolecules such as proteins or nucleic acids) that are moved through the membranes. For example, the membranes may be dipped in, coated with, or impregnated with nitrocellulose, poly-L-lysine, or mixtures thereof. In certain examples the membranes are not treated with a material that blocks the non-specific binding of the biomolecules to the membranes, at least during transfer of the biomolecules through the membranes. However, in other embodiments, some such blocking agents can be added to the membranes, as long as the amount of blocking agent minimizes the amount of biomolecules bound, without blocking it altogether. In certain examples, blocking agent may be added to the membranes after transfer of the biomolecules through the membranes, but before or during exposure to the detectors.

In particular examples, the membranes are sufficiently thin to allow th biomolecules to move through th plurality of membranes (for example 10, 50, 100 or more) in the stack. Such membranes, for example, have a thickness of less than 30 microns. The membranes may be made of a material that does not substantially impede movement of the biomolecules through the membranes, such as polycarbonate, cellulose acetate, or mixtures thereof.

The material of the membranes may maintain a relative relationship of biomolecules as they move through the membranes, so that the same biomolecule (or group of biomolecules) move through the plurality of membranes at corresponding positions. In such examples, this coherence of relative relationships allows the different membranes to be substantial "copies" of one another, much like a "carbon copy" would be. However, like a "carbon copy" there may be some differences between the different "copies" present in the different membranes.

In some embodiments, a membrane stack will include a number of individual membranes, for instance at least 2, at least 5, at least 10, at least 20, at least 50, or even more in some instances. Membranes in the stack are generally constructed as described herein. Examples of the membranes are constructed of a porous substrate coated with a material that increases the affinity of the membrane to the biomolecules being transferred. The substrate may be constructed of polycarbonate or a similar polymeric material that maintains sufficient structural integrity despite being made porous and very thin. Representative membranes for use in the methods, devices, and apparatuses have a high affinity for proteins and/or other biomolecules, but have a low capacity for retaining such molecules. This binding profile permits biomolecules to pass through the membrane stack with only a limited number being trapped on each successive layer, thereby allowing multiple "carbon copies" of the biomolecules in the sample to be generated. In other words, the low capacity allows the creation of multiple replicates as only a limited quantity of the biomolecules is trapped on each layer.

Figure 12:
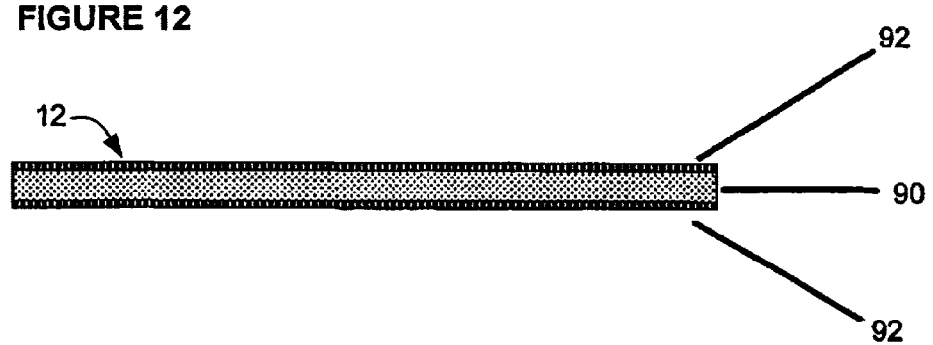
FIG. 12 is a longitudinal sectional view of an individual membrane according to one provided embodiment.

With reference to FIG. 12, individual membranes 12 are constructed of a porous substrate 90 coated with a material that increases the affinity of the membrane to the biomolecules being transferred. Substrate 90 is, for example, constructed of polycarbonate or a similar polymeric material that maintains sufficient structural integrity despite being made porous and very thin. However, in lieu of polycarbonate the substrate 90 may for example be constructed of cellulose derivatives such as cellulose acetate, as well as polyolefins, (e.g., polyethylene, polypropylene, etc.).

The illustrated membrane 12 includes a coating 92 on its upper and lower surfaces to increase non-specific binding of the proteins or other targeted biomolecules. Although the binding to the coating is "non-specific" in the sense that it does not recognize particular proteins or other biomolecules, such as particular nucleic acids, it may be specific in that it recognizes and specifically binds classes of biomolecules, such as proteins or nucleic acids, or combinations thereof. Coating 92 in specific disclosed embodiments is nitrocellulose, but other materials such as poly-L-lysine may also be employed.

Before being applied to substrate 90, the nitrocellulose is dissolved in methanol or other appropriate solvent in concentration from 0.10%–1.0%. The membranes are immersed in this solution as described more fully in the Examples, below. In lieu of coating 92, nitrocellulose or other materials with an affinity for biomolecules can be mixed with the polycarbonate before the substrate is formed thereby providing an uncoated substrate having all of the desired characteristics of the membrane. Alternative coating methods known in the art may be used in lieu of dip coating including lamination. Alternatively, only one surface may be coated, such as the surface that faces the sample, instead of both surfaces.

It is a particular feature of certain embodiments that membranes 12 have a high affinity for proteins and other biomolecules, but have a low capacity for retaining such molecules. This feature permits the molecules to pass through the membrane stack with only a limited number being trapped on each of the successive layers thereby allowing multiple "carbon copies" to be generated. In other words, the low capacity allows the creation of multiple substantial replicates as only a limited quantity of the biomolecules are trapped on each layer. If a membrane were used that had a high binding capacity for biomolecules-such as with nitrocellulose membranes conventionally used with gel blotting-multiple replicas could not as easily be made. More specifically, the affinity and capacity of membrane 12 should be such that when at least five and preferably more than ten membranes are stacked and applied to a sample according to a disclosed method, most of the biomolecules of interest can be detected on any and all of the membranes, including those positioned furthest from the sample.

Figure 13:
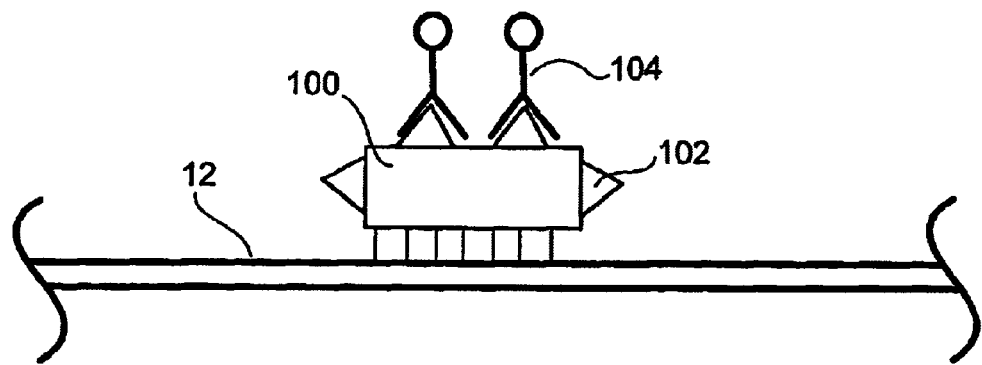
FIG. 13 is a schematic drawing, illustrating direct capture.

With reference to FIG. 13, the aforementioned technique may be described as "direct capture" since the target biomolecules 100 are captured directly on the surface of membranes (or within the membrane), instead of being captured indirectly by a binding agent (such as an antibody or nucleic acid probe) applied to the membrane. During this disclosed process different components of the sample bind to the membrane with the same affinity, but directly proportional to their concentration in the sample (a component with a higher concentration will leave more molecules on each membrane, and a component with a lower concentration will leave less molecules on each membrane). A detector molecule 104, such as a labeled antibody that specifically binds to the biomolecule 100 at illustrated epitopes 102, may be utilized to detect biomolecule bound to the membrane. In examples in which the amount of a component bound to the membrane is proportional to the amount of the component in the sample, an amount of the detector molecule can be correlated to an amount (or relative amount) of the biomolecule detected.

Figure 14:
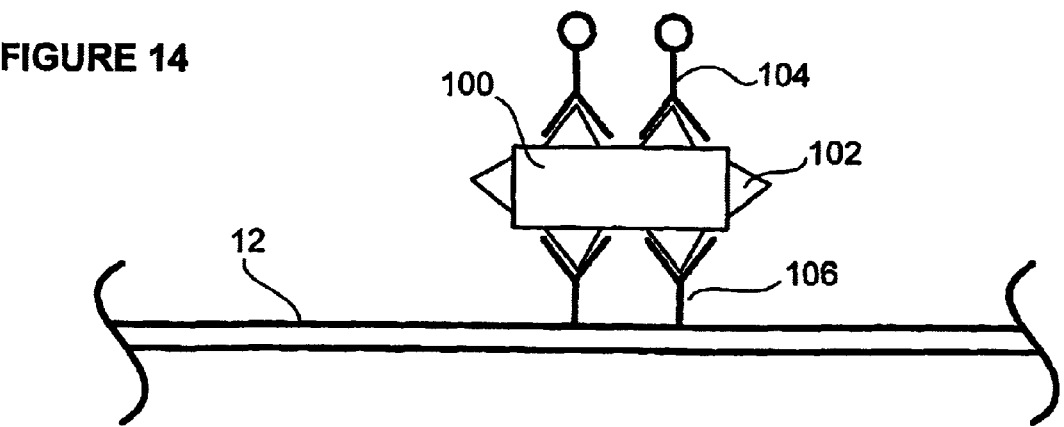
FIG. 14 is a schematic drawing, illustrating indirect capture.

In order to achieve high affinity and high capacity for a particular group of biomolecules from a sample, coating of the membranes with a captor molecule 106 is performed in the method described by Englert et al. (*Cancer Research* 60:1526–1530, 2000). This may be referred to as "indirect capture" and is illustrated in FIG. 14. Captor 106 can be cDNA, antibody, or any other protein specific for the target of interest. Single-stranded cDNA molecules generated by number of means (Polymerase Chain Reaction, nick translation, reverse transcription, oligonucleotide synthesis) or proteins (like immunoglobulin) can be directly attached to the membrane. Alternatively, the linker-arms that would allow spatial control of the captor binding could be directly attached to the membrane followed by captor attachment to them. This will expose the majority of the active target recognition sites increasing that way capacity of the indirect capture. Streptavidin coated membranes may be employed to bind end-biotinylated nucleic acids and randomly biotinylated proteins, or protein A and protein G to bind immunoglobulins.

Figure 15:
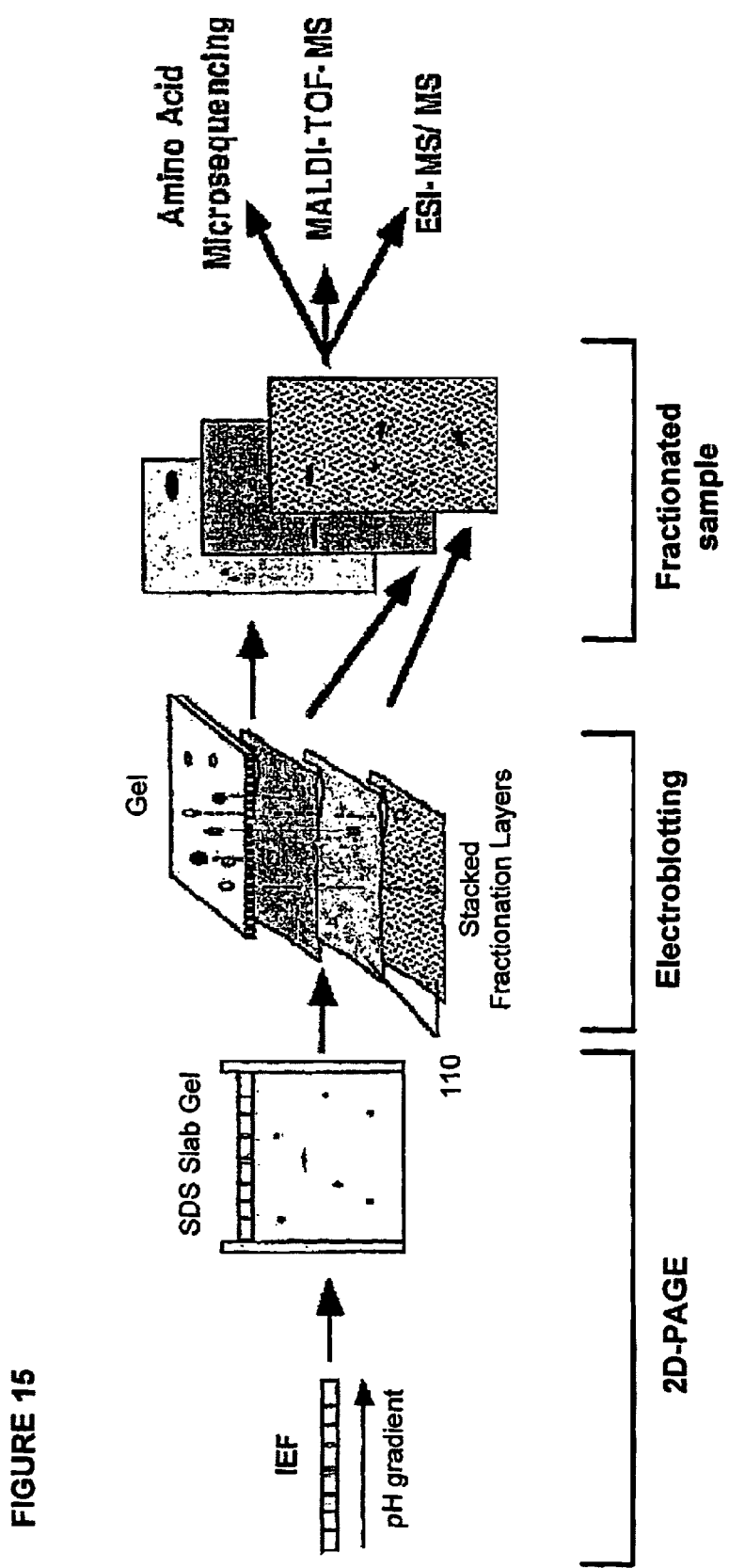
FIG. 15 is a schematic illustration showing a method according to another gel-transfer embodiment

In another embodiment (illustrated in FIG. 15), each of the membranes 108 comprise a ligand coating (e.g., a unique ligand coating, in that it is different from the others in the stack) that selectively binds to proteins in the biological sample based on a particular characteristic of the protein chemistry (e.g. hydrophobicity, carbohydrate content, etc.) As a result, the membranes 108 function to fractionate the proteins rather than replicate them as with membranes 12 in other described embodiments. The coating could be made in many different ways so that each membrane binds a selective subset of the total protein content in the sample. For example, carbon chains of increasing length, starting with a small carbon molecule can be used in the coating. As the number of carbons increases the ability to bind to proteins increases. Thus, for example, the first layer may have a six carbon-chain coating and will only bind to the most hydrophobic proteins in the sample, the remaining proteins will pass through to the next layer; the second layer has an eight-carbon chain and will pull out slightly less hydrophobic proteins while the remaining proteins pass through; the third layer has a ten carbon-chain, etc.

Thus, with another embodiment, each of the membranes will bind to a different group of proteins essentially permitting "3-D gel electrophoresis" by allowing proteins to be separated into three dimensions: in the X and Y dimensions by charge and mass, and then in the Z dimension by an additional chemical characteristic. The proteins on the membranes according to the second embodiment can be visualized by the immuno-staining and imaging methods set forth below. They may also be advantageously analyzed by mass spectrometry either without additional cleavage or after such cleavage (see, e.g., WO00 045168), or by other means. Examples of the methods and kits facilitate such analysis because the stratification by the different membranes helps to expose moderate and low abundance protein spots that would otherwise be undetectable on standard 2-D gels. The more spots that are available for analysis, the more data can be generated by mass spectroscopy or by such other approaches.

Other Membrane Characteristics

It is a particular feature of some embodiments that membranes used for the transfer have a high affinity for proteins and/or other biomolecules, but have a low capacity for retaining such molecules. This feature permits the molecules to pass through the membrane stack with only a limited number being trapped on each of the successive layers, thereby allowing multiple replicate "carbon copies" to be generated. In other words, the low capacity of the membrane material allows creation of multiple replicates, since only a limited quantity of the biomolecules (e.g. proteins) are trapped on each layer.

More specifically, in specific embodiments the affinity and capacity of membrane should be such that when at least five and preferably more than ten membranes are stacked and applied to a sample according to one of the provided methods, most of the biomolecules of interest can be detected on any and all of the membranes, including those positioned furthest from the sample. If a membrane were used that had a high binding capacity—such as the transfer membranes used with conventional gel blotting, multiple replicas could not be made in this manner unless the binding capacity of the membrane was overwhelmed by the amount of biomolecule applied to the membrane.

To maintain the binding capacity of membrane sufficiently low to avoid trapping of too much of the sample, the thickness of the substrate is, for example, less than about 30 microns, and in particular embodiments is between about 4–20 microns, for example between about 8 to 10 microns. The pore size of the substrate is, for example, between about 0.1 to 5.0 microns, such as about 0.4–0.6 microns, and more specifically 0.4 microns. Another advantage of using a thin membrane is that is lessens the phenomenon of lateral diffusion. The thicker the overall stack, the wider the lateral diffusion of biomolecules moving through the stack.

It will be appreciated that because the size of the membranes in the stack/array can be varied, the user has the option of analyzing a large number of different samples in parallel, thereby permitting direct comparison between different patient samples (e.g. different patient samples, or patient samples and a reference standard, or samples of different tissues or species, etc.). For example, different samples from the same patient at different stages of disease can be compared in a side-by-side arrangement, as can samples from different patients with the same disease. By way of alternative example, the area of protein separation resulting from most 2-D gels is generally between about 10×10 cm to 20×20 cm; membranes used for transfers of 2-D gels may vary accordingly.

Membrane Construction

The membrane substrate includes a coating on its upper and lower surfaces to increase specific binding of the proteins or other targeted proteins. The coating is preferably nitrocellulose but other materials such as poly-L-lysine may also be employed. Before being applied to substrate, the nitrocellulose is dissolved in methanol or other appropriate solvent in concentration from 0.1%–1.0%. The membranes are immersed in this solution as described more fully in the Examples, below. In lieu of coating, nitrocellulose, or other materials with an affinity for proteins, can be mixed with the polycarbonate before the substrate is formed thereby providing an uncoated substrate having all of the desired characteristics of the membrane. Alternative coating methods known in the art may be used in lieu of dip coating, including lamination. In all instances it should be understood that preferably only one surface—the surface that faces the sample—is coated or treated, instead of both.

Framed Membranes

Figure 16:
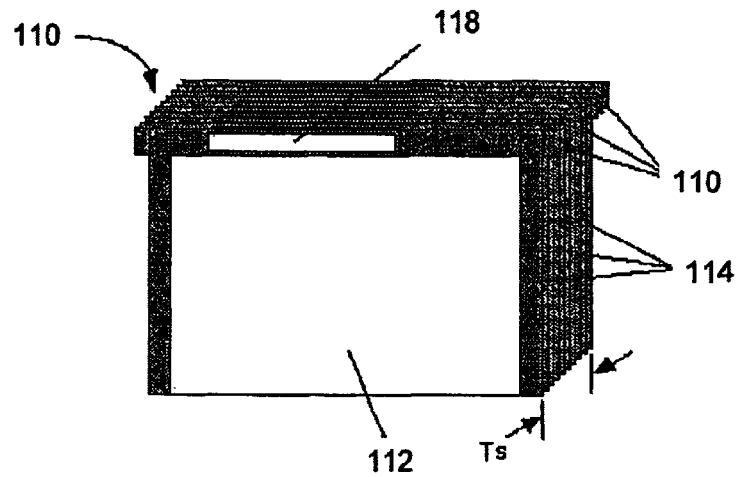
FIG. 16 is a perspective view of a representative framed membrane stack.
Figure 17:
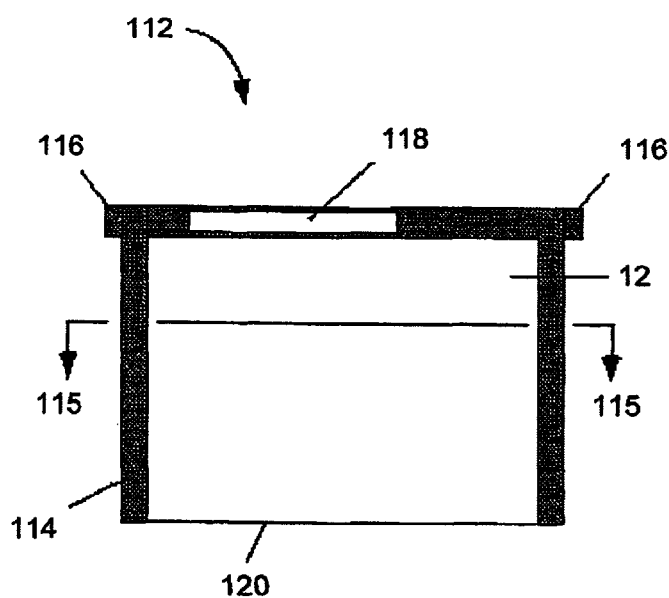
FIG. 17 is a front elevation view of a single framed membrane.
Figure 18:
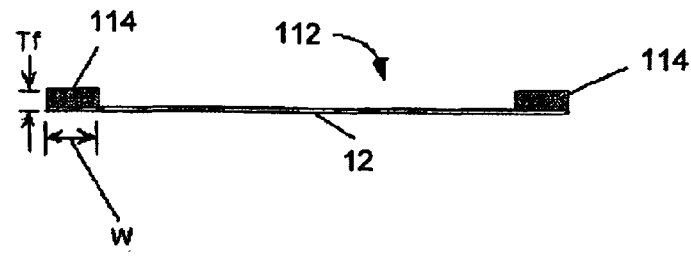
FIG. 18 is a sectional view of the single membrane taken along line 115—115 of FIG. 17.

In another embodiment, with reference to FIGS. 16–18, framed membrane stack 110 comprises a plurality of individual membrane units 112 releasably secured to one another. Each membrane unit 112 comprises a membrane 12 having a frame 114 mounted about the periphery thereof. Membrane unit 112 can vary in size but should be large enough so that membrane 12 can overlay a typical electrophoresis gel.

The number of membrane units 112 included in stack 110 can vary depending on the number of proteins to be detected from the gel. For most applications, from 3 to 25 or more membranes will be sufficient, preferably from 5 to 15 and most preferably about 10 to 12. The entire thickness, Ts, of stack 110 (FIG. 16) is in some embodiments no more than about 0.25 cm.

In some embodiments, in order to give each membrane sufficient rigidity to enable it to be separated the other membranes in stack 110 and individually processed, a frame 114 is mounted onto the periphery of membrane 12 thereby forming membrane unit 112. Frames 114 preferably comprise a generally "Z" shaped configuration covering three sides of the membranes while defining an open space or gap 120 that functions as a channel to permit the manual removal of air pockets or fluids in the manner described.

The composition and dimensions of frame 114 should be such that the frame provides sufficient rigidity for the user to grip the frame with one hand and manipulate the membranes as needed. At the same time, the frames must be sufficiently thin so that when stacked they do not interfere with protein transfer from the gel onto the membrane stack 110. Each membrane 12 in stack 110 should be capable of making direct contact with adjacent membranes during the transfer process described herein.

The width W (FIG. 18) of frame 114 is preferably between about 0.3 to 0.7 cm and the thickness of the frame, Tf, is between about 0.005 to 0.03 cm., most preferably about 0.01 cm thick. Thus, frame 114 is about ten times thicker than membrane 12. In certain embodiments, the materials that comprise frames 114 are able to maintain their structure and function at temperatures of up to 80° C. but are able to melt when applied to a typical heat-sealing apparatus. One skilled in the relevant art will readily appreciate that a variety of compositions and configurations of frames 114 could meet these requirements. Examples of materials that may be employed to make frames 114 are transparency film available from Canon or any thin plastic sheet made of polycarbonate, polyester, polyvinylchoride or polyvinilechloride.

As best viewed in FIG. 17, a pair of outwardly depending tabs 116 is defined by frame 114. Each tab is adapted to be sealed to the corresponding tab on an adjacent membrane so as to hold stack 110 together during the gel transfer process. After the proteins are transferred onto the membranes tabs 116 are cut with a scissors so that the membranes may be separated and incubated in separate detection solutions.

At least one side of frame 114 defines a surface 118 upon which indicia may be imprinted. The indicia may include the name of the product or manufacturer or the membrane number. Machine-readable indicia such as a bar code or the like (not shown) may also be provided.

Frames 114 may be mounted to the perimeter of membranes 12 by various means readily familiar to those skilled in the art including use of adhesives such as rubber cement or 3M adhesive or conventional heat-sealing or laminating techniques.

VI. Analysis of Membrane Replicates

After transfer, the processed membranes (or layers) can be separated and each incubated with one or more different detector molecules (such as nucleic acid hybridization probes, lectins, or antibodies) specific for particular targets of interest. In certain embodiments, the detectors/probes employed are labeled or otherwise detectable using any of a variety of techniques such as chemiluminescence. Thus, while each membrane has essentially the same pattern of biomolecules bound to it, different combinations of biomolecules can be made observable on each membrane by selecting particular probes to be applied and detected.

By way of example, one membrane layer may display proteins involved in programmed cell death (apoptosis) while an adjacent layer may display enzymes involved in cell division such as tyrosine kinases.

In addition to proteins, nucleic acids may be targeted and detected by using labeled DNA hybridization probes rather than antibodies. Moreover, both protein and nucleic acid targets can be detected in parallel by applying both antibodies and nucleic acid probes to different layers of the stack. Similarly, carbohydrates can be detected using carbohydrate-binding molecules such as lectins.

Digital images of membranes may be created using a variety of instruments including the Image Station® CCD instrument available from Kodak Scientific Imaging (New Haven, Conn.). Alternatively images may be captured on film (such as X-ray film) and digitalized by flat bed scanners. Software is preferably provided to align the images and perform densitometry functions. The user can select the region of interest for analysis and the signal intensities are recorded and normalized. The numerical intensity values are then compared.

For analysis of transferred proteins, after the transfer by any of the herein-described protein-transfer techniques, the membranes are separated from stack and each is incubated in a separate solution of primary antibody specific for a desired protein. Only the band containing this protein binds the antibody, forming a layer of antibody molecules. After incubation for about 1–8 hours, the membranes are usually washed in buffer to remove unbound antibody.

For detection of the proteins on the membranes (in the form of bands, spots, or "in situ" from tissue transfers), the loaded membranes are incubated in a secondary antibody that binds to the primary antibody. The secondary antibody may be covalently linked to an enzyme such as horseradish peroxidase (HRP) or alkaline phosphatase (AP) that catalyzes substrate and protein/antibody complex can be visualized using a number of techniques such as ECL, direct fluorescence, or calorimetric reactions. ECL is preferred. Commercially available flatbed scanners may be employed in conjunction with film. Alternatively, specialized imaging instrumentation for ECL, such as the Kodak IMAGE STATION available from NEN may be utilized and digital imaging software can be employed to display the images according to the preference of the user.

In lieu of antibodies, other ligands may be employed as detectors. Ligands can be antibody fragments, receptors, receptor ligands, enzymes, viruses or viral particles, enzyme substrates or other small molecules that bind to specific proteins. Moreover, in addition to identifying proteins of interest structurally, kits can also be employed to identify the functional state of proteins. One way to do so is to use phospho-specific antibodies to determine the phosphorylative state of protein(s) of interest. Another approach to identifying protein function is to first renature the proteins on the membranes by any of a number of techniques known in the art such as incubating the membrane in Triton-X® (octylphenol polymerized with ethylene oxide). Once renatured, proteins will regain their enzymatic activity and one of several substrate degradation assays known in the art can be used. With this approach the activity of kinases, phosphates and metalloproteinases can be determined.

Panels for scientific research may be grouped by the proteins involved in a particular cellular phenomenon such as apoptosis, cell cycle, signal transduction, etc. Panels for clinical diagnostics may be grouped by proteins associated with a particular disease such as Alzheimer's disease, prostate cancer, etc.

In many embodiments, the detectors/ligands employed are labeled or otherwise made detectable using any of several techniques, such as enhanced chemiluminescence (ECL), fluorescence, counter-ligand staining, radioactivity, paramagnetism, enzymatic activity, differential staining, protein assays involving nucleic acid amplification, etc. The membrane blots are preferably scanned, and more preferably, digitally imaged, to permit their storage, transmission, and reference. Such scanning and/or digitalization may be accomplished using any of several commercially available scientific imaging instruments (see, e.g., Patton et al., *Electrophoresis* 14:650–658, 1993; Tietz et al., *Electrophoresis* 12:46–54, 1991; Spragg et al., *Anal Biochem.* 129:255–268, 1983; Garrison et al., *J Biol. Chem.* 257:13144–13149, 1982; all herein incorporated by reference).

Example Detection Chemistries with Detector Cocktails

In certain embodiments, after proteins have been transferred through the membrane stack, individual membranes layers are separated and each is incubated in a separate antibody (or other detector molecule) cocktail. A key advantage of creating multiple replicate blots is that many more detector molecules (e.g., antibodies) can be usefully employed than if all of the detectors had to be crowded onto a single blot.

An exemplary process for designing the ligand cocktails—and for determining which proteins will be identified on each membrane layer—is provided below. First the panel of proteins of interest is selected. These can be randomly selected proteins and/or proteins that are not directly related to one another or may be groups of known proteins previously implicated to play a role in one or more particular cellular phenomena (e.g. apoptosis, cell cycle progression) or a particular disease (e.g. prostate cancer specific antigen, PSA). These should be proteins that have been characterized by sequence or coordinates on 2-D gels or for which ligands have been or could be generated. Data bases of annotated 2-D gels include the Quest Protein Database Center (http://siva.cshl.org), the Swiss 2-D PAGE database (http://expasy.cbr.nrc.ca/ch2d), Appel et al. *Electrophoresis.* 14(11): 1232-1238, 1993; the Danish Centre for Human Genome Research (http://biobase.dk/cgi-bin/celis), Celis et al., *FEBS Lett.* 398(2–3):129–134, 1996, etc. Antibodies may be obtained from a variety of sources such as BD Transduction Laboratories (Lexington, Ky.) or Santa Cruz Biotechnology (Santa Cruz, Calif., USA).

Although, as discussed above, any of a broad class of ligands may be employed, for simplicity the embodiment is illustrated with reference to the use of antibody ligands. Immunological identification of the proteins on the membranes thus preferably involves the selection of antibodies having a high affinity and specificity for their targets. However, antibodies, both monoclonal or polyclonal, frequently recognize more then one protein in Western blotting detection. This cross-reactivity phenomenon becomes increasingly apparent as the concentration of antibody increases relative to that of the sample proteins. Hence, the first step in the antibody selection process preferably involves choosing antibodies (and their working concentrations) that consistently visualize preferably 1 but no more then 5 proteins on the same membrane. When the detector antibody binds to more than one spot, the undesired proteins ("false spots") can be eliminated based on their X-Y positions on the membranes. Since the molecular weight and charge (pI) of a given protein is generally constant, it should appear at about the same coordinates on the gel each time it is run.

If two or more proteins in a sample are of similar size and charge—and therefore migrate to the same general vicinity on the gel—they would likely create overlapping spots if detected on the same membrane. In a preferred embodiment, examples of the method avoid this problem by designing the antibody cocktail to detect adjacent or overlapping proteins on different membranes.

Figure 19:
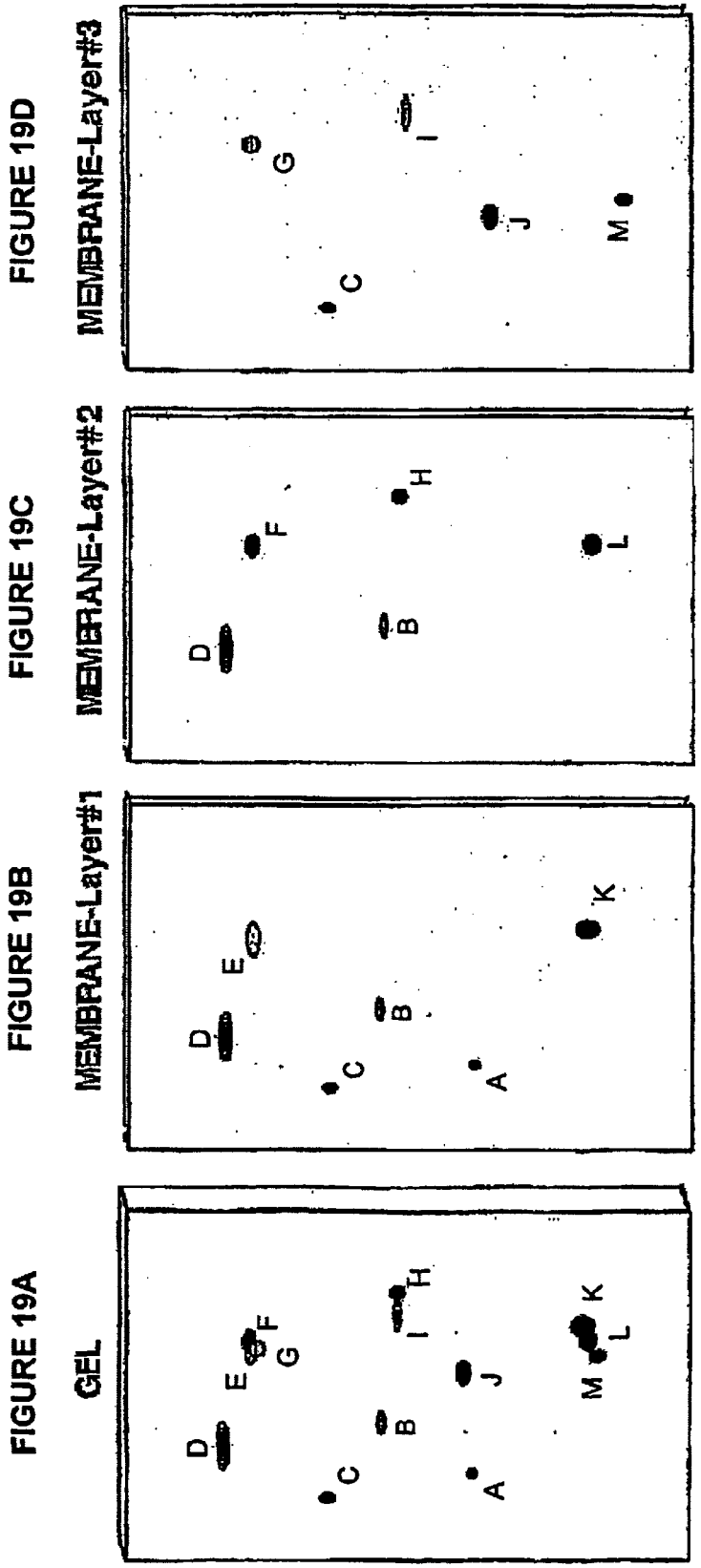
FIG. 19 is a schematic illustration showing a hypothetical example illustrating the method of creating the antibody cocktails. The Gel (A) shows proteins as detected by Coomassie Blue staining prior to transfer. Membrane-Layer #1 (B), Membrane-Layer #2 (C), and Membrane-Layer #3 (C) show proteins detected on membranes with antibodies.

The cocktail design process can be readily understood with reference to the following hypothetical example (illustrated in FIG. 19). For simplicity in this example, thirteen proteins annotated as A–M in FIG. 19A are sought to be identified using only a three-layer membrane stack. The ligands employed in the example are antibodies, and three cocktails, one for each stack, each with four to six different antibodies, are employed.

For the first membrane cocktail (corresponding to layer one) antibodies are screened for protein spot A and the most specific antibody is selected. Antibodies for spots B–E are picked the same way. Because spots F and G overlap with spot E these are put aside for other layers. The second and third cocktails (corresponding to membrane layers two and three) are created using the same considerations: (1) if the spot position generated by any two antibodies cannot be easily distinguished, the antibodies will not be used in the same cocktail; (2) if any antibody results in a background spot near the spot generated by another antibody, the two antibodies will not be included in the same cocktail unless the background spot is remote from other spots on that layer (e.g. spots B and D on layer 2 created due to cross-reactivity from antibodies directed to other spots), in which case such cross-reactivity is simply ignored when the membrane spots are compared to the template. Applying these considerations to the hypothetical example results in three cocktails corresponding to the layers illustrated in FIGS. 19B–D.

Once assembled, the antibody cocktails will be additionally tested for their specificity by two different control tests. In a first test, membranes made from the transfer of a single gel (or from several gels that contain the same sample and were prepared in the same manner) will be probed with cocktails that differ in only one antibody component (each cocktail will lack one of the antibodies). As a result of this procedure, immunoblotted membranes should differ from each other in only one spot. In a second test, antibody cocktail will be incubated for 0.5–12 hours at 4–25° C. with a mixture of epitopes (peptides or proteins) that are used for immunization. During this incubation, free antibodies bind to the appropriate epitopes and become immobilized and functionally inactive. Since the cocktail becomes depleted of free antibodies subsequent incubation of the membrane with this free antibody depleted mixture should yield no specific signal.

Each cocktail will also include one or more antibodies against "housekeeping" proteins (i.e., abundant structural proteins found in all eukaryotic cells such as actin, tubulin, etc.). Thus, for example, the antibodies employed with respect to membrane Layer #1 of FIG. 19 will contain an antibody to actin, which will result in the production of a spot. These antibodies serve as internal landmarks to normalize samples for loading differences and to compensate for any distortion caused by gel running process. Once the cocktails are designed, they can be reused in any kit that seeks to identify the same panel of proteins that were identified in creating the cocktails, regardless of the origin of the sample.

It will be appreciated that the present disclosure allows not only the simultaneous characterization of a large number of different proteins but also permits the characterization of a large number of characteristics of a single protein based on number of different characteristics. For example, the protein p70 S6 kinase, required for cell growth and cell cycle progression, is activated by phosphate group attachments (phosphorylation) to threonine on position 229 and/or 389 of the protein. Identification of this kinase would provide not only a determination of its presence or absence but also a demonstration of its activity. By way of example, with a kit containing at least a four-membrane stack, four copies can be made of a 2-D gel. The first membrane would be incubated in antibody specific for the whole protein to determine if this enzyme is present in the sample or not The second membrane can be used in kinase assay to determine if the enzyme is active or not. The third membrane can be probed with phospho-p70 S6 kinase (Thr229) antibody to determine if activity of the enzyme is due to activation of this site. The fourth membrane can be probed with phospho-p70 S6 Kinase (Thr389) antibody to determine if the activity of the enzyme is due to activation of that site. And since all of these tests are done on the single sample (rather than different batches of the same sample) the information obtained is more reliable.

Figure 4B:
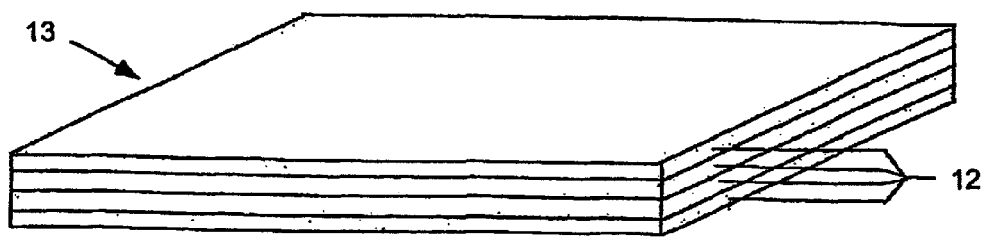
FIG. 4B is a perspective view of a membrane stack.

Antibody cocktails (such as those illustrated in FIGS. 4 and 5, reference number 38) are preferably stored in vials, preferably made of plastic or glass, and are optionally combined in a kit to create a "panel" of protein targets of interests. Panels for scientific research may be grouped by the proteins involved in a particular cellular phenomenon such as apoptosis, cell cycle, signal transduction, etc. Panels for clinical diagnostics may be grouped by proteins associated with a particular disease such as Alzheimer's, prostate cancer, etc.

VII. Kits

Other embodiments of the disclosure include kits that contain a membrane array for detecting biomolecules (such as proteins or nucleic acids) in a sample. The array includes a plurality of membranes, each of which has a non-specific or substantially same affinity for the biomolecules. Certain provided kits also include one or more containers of detector molecules, such as antibodies or probes (or mixtures of antibodies, mixtures of probes, or mixtures of the antibodies and probes), for detecting biomolecules captured on at least one of the membranes. In particular examples of the kit, the membranes are polymer substrates containing or coated with a material (such as nitrocellulose) for increasing an affinity of the substrate to the biomolecules.

Kits may additionally contain reagents for effecting the detection of detector/ligand-biomolecule binding, buffer, and/or instructions or labels that indicate the particular detector or detector cocktail to be applied to a particular membrane. Software such as that discussed herein may also be included in the kit or may be accessible via modem, the Internet, by mail, or by other means.

Primary antibodies to particular groups of proteins, such as biochemical pathways may be optionally included with a kit. Alternatively the user can supply primary antibodies.

The methods and kits allows up to several thousand discrete protein spots to be identified, annotated, and, at the user's option, compared to the pattern of protein spots generated from other biological samples stored in a database.

Figure 20:
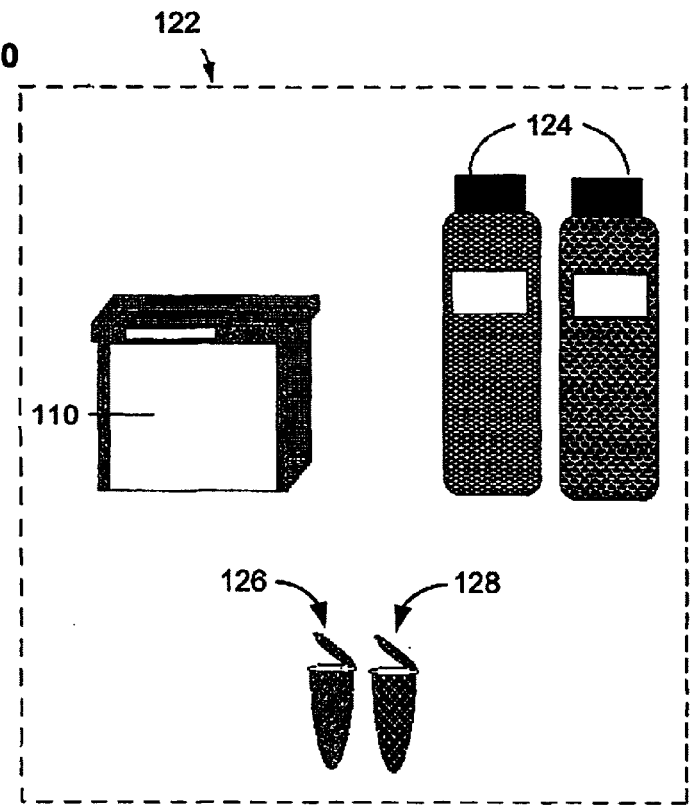
FIG. 20 is a schematic illustration showing the components of a kit according to one embodiment.

Certain kit embodiments have been discussed above, including first kit 36 and second kit 58. Also provided is another specific embodiment, directed to a method and a kit 122 for identifying (i.e. detecting, annotating, and/or characterizing) groups of proteins that have been separated by gel electrophoresis. As illustrated in FIG. 20, representative kit 122 comprises the following components: (i) a membrane stack 13 or framed membrane stack 110 (as illustrated) upon which the proteins are transferred, (i) protein transfer reagent(s) 124 and (iii) protein detector molecules, such as stain 126 and protein-specific detector molecule 128. The kit may also include software 46 (not shown in FIG. 20) that allows the user to analyze and manipulate the images produced so as to yield a "proteomic image" of the biological sample being tested and compare it to proteomic images from other samples in a database. Alternatively the software may be acquired or accessed independent of the kit.

In some embodiments, transfer reagent is also provided with a kit. Examples of transfer reagents include Tris, Phosphate, Tris/Glycine or Phosphate/Glycine buffers with an alkaline pH (e.g., 8.0–9.5), with or without methanol (usually 20% or less) and/or SDS (in some embodiments 0.05% or less, and in particular embodiments 0.025% or less). Specific examples of transfer reagent suitable for use in examples of such kits are in the Examples.

In addition to identifying proteins of interest structurally, kits are provided that can be employed to identify the functional state of proteins. One way to do so is to use phospho—specific antibodies to determine the phosphorylation state of protein(s) of interest. Another approach to identifying protein function is to first renature the proteins on the membranes by any of a number of techniques known in the art (such as incubating the membrane in Triton-X-100® (octylphenol ethylene oxide condensate). Once renatured, some proteins will regain their functional activity and one of several substrate degradation or modification assays known in art can be used. With this approach the activity of kinases, phosphates and metalloproteinases, etc., can be determined.

VIII. Devices and Apparatuses

In certain provided embodiments, particularly those which employ contact transfer, the transfer can be effected by placing the assembled membrane stack into a gel drier-type apparatus, which applies heat and/or pressure to the stack. The combination of heat and pressure being applied causes biological components, including proteins and/or nucleic acids and/or carbohydrates and/or lipids, to be transferred from the sample 11 to membrane stack 13. This produces multiple copies or replicas of the biomolecular content of the tissue sample, due at least in part to the binding characteristics of the membranes.

In lieu of gel dryers, a specialized instrument 130 (FIG. 21) may be employed to provide heat and/or pressure to the sample and membrane stack. The instrument comprises a body 134 and a lid 136, each having a face 132a, 132b which serves as one of the substantially flat surfaces 132. The surfaces may be provided by the upper face 132b of the body 134 and the lower face 132a of the lid 136 directly, or may be provided by a substantially flat panel or other flat object disposed on a face 132a, 132b of the body 134 or lid 136.

One or both of the substantially flat surfaces may protrude in order to ensure adequate contact to provide pressure between them. In the illustrated embodiment, for instance, the upper substantially flat face 132a is a surface of a member that protrudes from th lower face 132a of the lid 136. In some embodiments, one or the other or both of the substantially flat surfaces 132a, 132b may be compressible (for instance, somewhat spongy), to further ensure that pressure applied to the sample and membrane stack is relatively complete and even across the surface of the stack.

Figure 21:
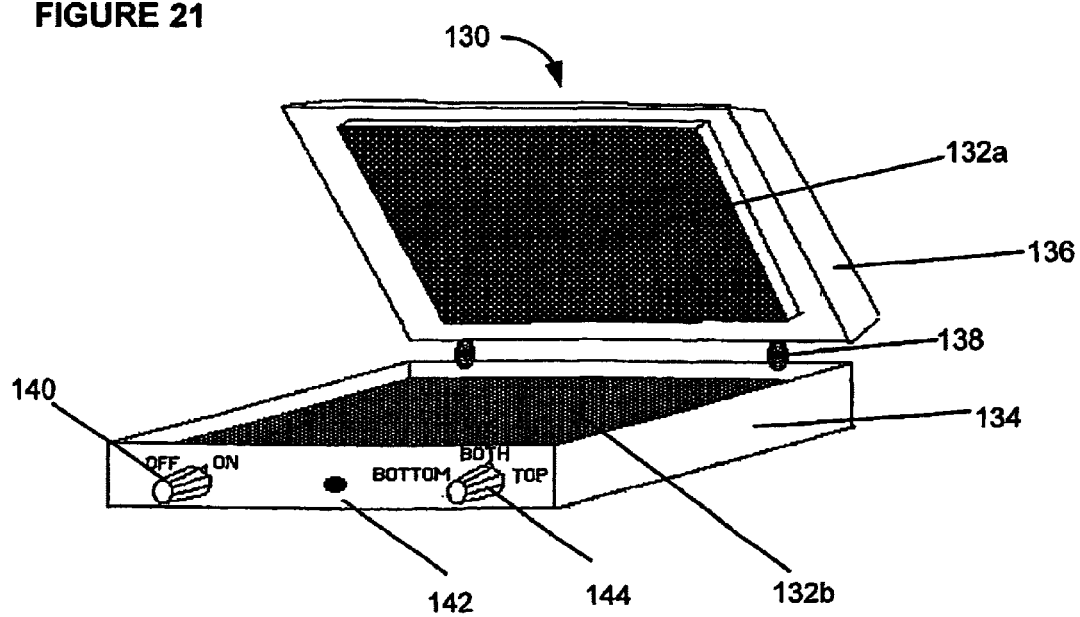
FIG. 21 is an oblique view of a pressure heater apparatus.

The lid 136, in some provided embodiments including that illustrated in FIG. 21 may be of sufficient weight to provide sufficient pressure to a sample and membrane stack placed under the lid 136 so that it facilitates biomolecule transfer as described herein. Such weight is not required, but in those embodiments wherein the lid 136 does not provide sufficient weight, another mechanism for applying pressure is included. Such means includes for instance a separate weight (not shown), such as a weight 34 placed on the upper surface of the lid 136, or clips, springs, clamps or the like that urge the lid 136 toward the base 134 with sufficient force to provide the amount of pressure needed to facilitate transfer.

In some embodiments, the lid 136 may be hingedly attached to the body 134, such that when the lid 136 is lifted it does not come fully away from the body 34 but remains connected in at least one place. In the illustrated example (FIG. 21), two hinges 138 are provided to maintain the connection between the body 134 and the lid 136. In particular embodiments, the hinge or hinges 138 are "loose" or "floating," in that they permit some play between the lid 136 and the body 134. This play permits the device to accommodate assembled contact transfer stacks of different thickness, while still adequately applying sufficient and even pressure to the stack. Though some embodiments are large enough to accommodate multiple stacks in side-by-side arrays, it is not recommended that stacks of substantially different thickness be transferred in the same device at the same time, as the applied pressure may not be adequate on thinner stacks when a substantially thicker stack is present between the faces 132a, 132b.

Some embodiments of the device 130 are capable of supplying heat as well as pressure to the contact transfer stack. These embodiments may contain, for instance, a heater element (not shown) in the body 134 or the lid 136, or both, that provides heat to one or both of the substantially flat faces 132a, 132b. Examples of such heated devices 130 will be equipped with an internal or external power source, for instance a battery (not shown) or connection to a source of alternating current (not shown). Methods of and mechanisms for providing heat to a surface are well known, as are thermostats for controlling the level of heat provided. Specific examples of heated devices 130 will include a mechanism for controlling whether or not heat is generated (e.g. an "ON/OFF" switch 140 as shown in FIG. 21), a mechanism for regulating the level of heat produced (e.g., a thermostat, with or without a user control), and/or an indicator that indicates when the device is heating or heated. In the illustrated embodiment, an indicator light 142 is provided, which is capable of indicating when the device reaches a factory-set temperature (e.g., 80° C.), and is thus ready for use.

Specific examples of the heated device 130 that include a heater element in both the lid 136 and the body 134 may include a mechanism or control (such as dial 144) for selecting whether one, the other, or both heater elements are engaged when the device is turned on.

IX: Applications

The heat and pressure applied to contents of the enclosure permit proteins and other molecules to be transferred from the embedded cellular material to the membrane stack. This produces multiple copies or replicas of the biomolecular content of the cellular sample. The processed membranes (or layers) are then separated and each is incubated with one or more different probes or antibodies specific for particular targets of interest. The probes employed are labeled or otherwise detectable using any of a variety of techniques such as chemiluminescence. Thus, while each membrane has essentially the same pattern of proteins bound to it, different combinations of proteins are made visible on each membrane due to the particular probes or antibodies selected to be applied. For example, one membrane layer may display proteins involved in programmed cell death (apoptosis) while an adjacent layer may display enzymes involved in cell division such as tyrosine kinases. In addition to proteins, nucleic acids may be targeted by using labeled DNA probes in lieu of antibodies. Moreover, both protein and nucleic acid targets can be detected in parallel by applying both antibodies and probes to different layers of the stack. Commercially available flatbed scanners and digital imaging software can be employed to display the images according to the preference of the user.

Figure 22:
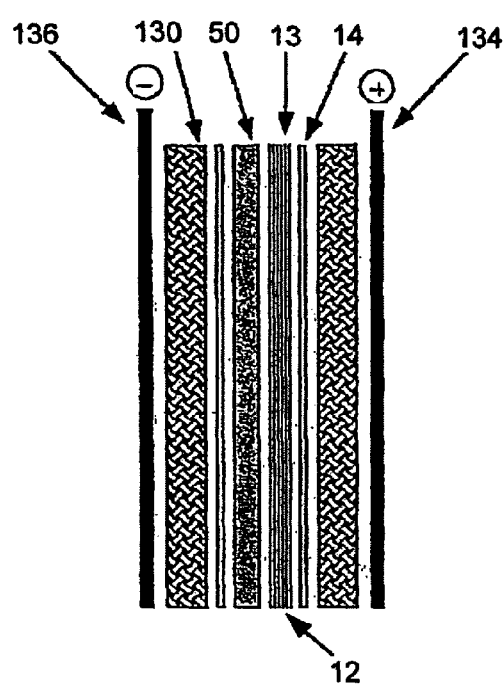
FIG. 22 is a longitudinal section view of a stack of membranes shown with apparatus to transfer proteins from a gel onto the membranes.

With reference to FIG. 20, kit 122 may be used to identify proteins that have been separated on electrophoresis gels, both two-dimensional gels and one-dimensional gels. Proteins are isolated from a biological sample and separated on the gel according to techniques well known in the art, such as those described herein and in Manabe, *Electrophoresis*. 21(6):1116–1122, 2000; Oh et al., *Electrophoresis*. 20:766–774, 1999; Dunn, *J Chromatogr.* 418:145–185, 1987, In some embodiments, after gel 50 is run, it is removed from the electrophoresis apparatus and sandwiched and placed in a transfer apparatus such as the type typically used in creating Western blots. Such devices are available, for example, from Biorad Laboratories, Inc., Novex, Inc. and Amersham Pharmacia. Membrane stack 13 is positioned between the electrodes adjacent to gel 50 as illustrated in FIG. 22. While only about a half-dozen membranes are shown in FIG. 22 it will be appreciated that up to one hundred may be employed depending on the number of targets sought to be identified in a panel, the quantity of proteins present in the sample, and the thickness of the material employed to construct membranes 12. Optionally, membranes 12 may be packaged in a suitable sealed enclosure or frame (not shown) to maintain their integrity and prevent contamination. Sponge pads 130, preferably constructed of foam, rubber or filter paper and layers of filter paper 14 are also sandwiched between the electrodes as shown in FIG. 22.

Transfer buffer (25 mM Tris pH 8.3, 192 mM glycine, 0.025% SDS and 20% methanol) is applied to elute and transfer proteins from the gel 50 to the membranes 12. Any of a variety of conventional methods for effecting such transfer may be employed, including wet tank transfer, and semi-dry transfer. In a wet tank transfer, the membranes are immersed into a tank containing buffer, in a semi-dry transfer, the membranes are blotted with moist pads. In both cases, the membranes are subjected to a voltage potential (e.g., 125–150 mAmps for 1–10 hours). In such transfer, it is important that a tight contact be created between the membranes and the gel. Wet tank transfer is preferred. For a membrane of $10\times10$ cm$^2$, a tank containing 400–500 ml of buffer may be employed. Preferred transfer conditions are 60–110 mAmps for 1–2 hours.

After transfer the membranes are separated and incubated with detector antibody(s). Antibodies are selected based on the types of target molecules sought. Membranes are washed in a buffer, and the protein/detector complex can be visualized using a number of techniques such as ECL, direct fluorescence, or colorimetric or calorimetric reactions. Commercially available flatbed scanners may be employed in conjunction with film, to detect or record signals. Alternatively, specialized imaging instrumentation (e.g., for ECL), such as the Kodak IMAGE STATION (NEN) may be utilized. Digital imaging software can be employed to display the images according to the preference of the user, as discussed herein.

In addition to use with 2-D gels, provided methods may be employed to identify proteins that have been separated by a 1-D gel such as conventional gels for separating proteins by size, and gel shift assays. Gel shift assays (also known as "mobility shift assays") are the most commonly used tool for studying protein—DNA interactions. The assay is based on labeling of the DNA fragment that contains presumptive protein binding site and incubation of that labeled fragment with protein that binds to that site. If they interact, complex will be formed. If source of protein is a cell extract (rather than a solution of in vitro synthesized proteins), the complex may contain number of proteins, of unknown identity, that interact with each other. After binding, a mixture of DNA and proteins is loaded onto a non-denaturing polyacrylamide gel and the proteins are separated based on their size. DNA-protein complexes are visualized by exposure to X-ray film, or by other means. The higher the bands are in the gel, the larger the size of the DNA-protein complex. In most cases, this type of analysis does not reveal identity of the protein(s) in the complex.

Figure 23:
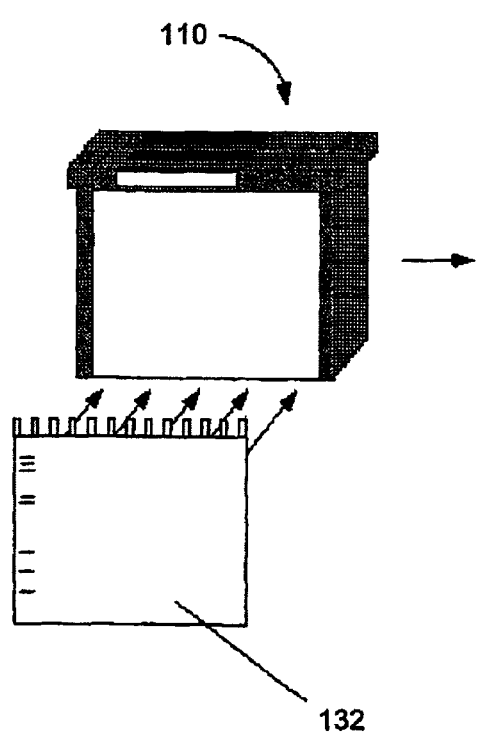
FIG. 23 is a schematic illustration of one embodiment in use and operation, showing the transfer of proteins from a gel to the membrane stack so as to create multiple replicates of the protein content of the gel.

As illustrated in FIG. 23, membrane stack 110 may be used to identify biomolecules that have been separated on electrophoresis gels, including proteins that have been separated on one-dimensional (1-D) gels 132 or two dimensional (2-D) gels (such as 50, not shown in this figure) as well as nucleic acids that have been separated on agarose gels. The following description relates to use of embodiments in conjunction with protein detection of 1-D gels.

Proteins are isolated from a biological sample and applied and separated onto a gel 132, typically a sodium dodecyl sulfate—polyacrylamide gel, which is cast, for example, as a square slab gel with a thickness between 0.5 to 2.0 mm. Pre-cast gels useful with the present disclosure can be obtained from a variety of suppliers including InVitrogen (Carlsbad, Calif.).

Unlike with conventional blotting, wherein less than 30 micrograms of protein is loaded into each well of the gel, according to specific methods herein between about 50 to 100 micrograms of protein is loaded into each well. The amount loaded will depend upon the number of "copies" of membranes to be created and size of the protein one wishes to detect (see Example 11).

Figure 24:
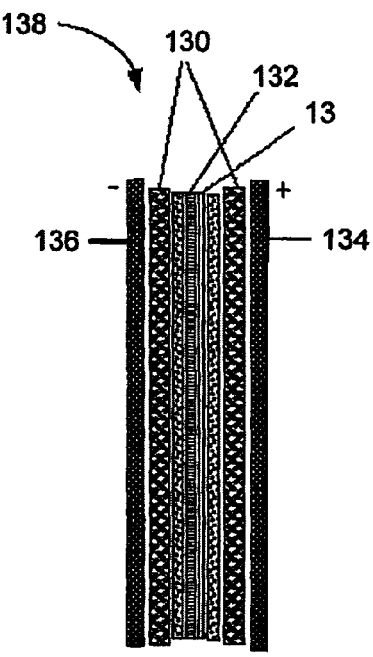
FIG. 24 is a sectional view of a stack of membranes shown operatively engaged with an apparatus to transfer proteins from a gel onto the membranes.

In some embodiments, the components of transfer buffer 124 are provided in separate containers, which are combined and applied to elute and transfer proteins from the gel 132 to the membranes 12. About 500 milliliters may be used in each transfer, with average length of the transfer being about 1–2 hours. With reference to FIGS. 23, 24, and 6, separated proteins on gel 132 are transferred to framed membrane stack 110 (though a stack of unframed membranes could be used) by one of several alternative techniques.

A first technique, illustrated in FIG. 24, involves electric transfer using a standard gel electro-blotting apparatus such as the MiniCell unit (Bio-Rad Laboratories, Calif.). Gel 132 is removed from the electrophoresis apparatus and placed adjacent to membrane stack 110. The gel 132 and membrane stack 110 are then placed between the anode 134 and cathode 136 of electro-blotting apparatus 138 with sponge pads 130 positioned as shown. The electro-blotting apparatus 138 is activated with a voltage of about 59–63 volts for about 60–70 minutes.

A second transfer technique (referred to as bi-directional contact transfer) is illustrated in FIG. 6. Here first and second membrane stacks 13a and 13b sandwich gel slab 54. A pair of filter pads 24 and 26, for instance constructed of a blotting paper such as GB004 Blotter Paper available from Schleicher and Schuell, are provided adjacent to the membrane stacks as shown. Filter pads 24 and 26 are saturated with a transfer buffer such as TRIS or phosphate base buffers.

A collapsible, fluid impervious enclosure 28 is provided to envelop the pads, membrane stacks, and gel as shown in FIG. 6. Plastic bag enclosure 28 is preferably a heat sealable pouch such as those available from Kapak Corp. (Minneapolis, Minn.). In many embodiments, it is best to remove most of the air from bag 28, for instance by gentle squeezing and/or vacuum suction. The bag is then sealed by a heat sealer such as the Impulse Sealer (American International Electric). Enclosure 28 is then placed between a pair of heating elements 56a and 56b such as those provided in Gel Dryers manufactured by Bio-Rad Laboratories (Hercules, Calif.). The bag and its contents are preferably heated to a temperature of between about 50 to 90° C., preferably to about 80° C. for about 2–4 hours. Pressure is preferably applied throughout the heating process using a weight 34. Alternatively, a specific device for applying heat and/or pressure (such as that illustrated in FIG. 21) can be employed.

The heat and pressure applied to contents of the enclosure permit proteins and other molecules to be transferred from the gel to the membrane stack. This produces multiple copies or replicas of the biomolecular content of the gel.

In addition to their use in identifying the proteins of the proteome, the methods and kits provided herein can be used to measure the concentration of a protein (either in absolute terms, or relative to the concentration of another protein). Likewise, they can be used to measure the distribution of variants of a protein, and to identify proteins that are analogous in structure or function to identified (e.g., human) proteins, or to identify plant clones or transgenic animals that express a particular protein or protein variant (which may be linked to, or associated with, a trait or phenotype).

X. Image Analysis Software

Software 46 is made available to users of any of the provided kits by providing it on a diskette to be included within the kit (e.g., kit 36, 58, or 122) or by making it accessible for downloading over the Internet or a private Intranet network, or by other means. The function of software 46 is to translate the visible spots generated by detector molecules (such as antibody cocktails 38) into useful information about the proteome of the sample being tested. This information primarily includes the quantity of the proteins in the test sample relative to a control and, in some cases, information about certain functional aspects of these proteins. Suitable software can be obtained from, or adapted from, any of a variety of sources (e.g., http://www.2dgels.com/home.html and http://expasy.proteome.org.au).

Figure 25:
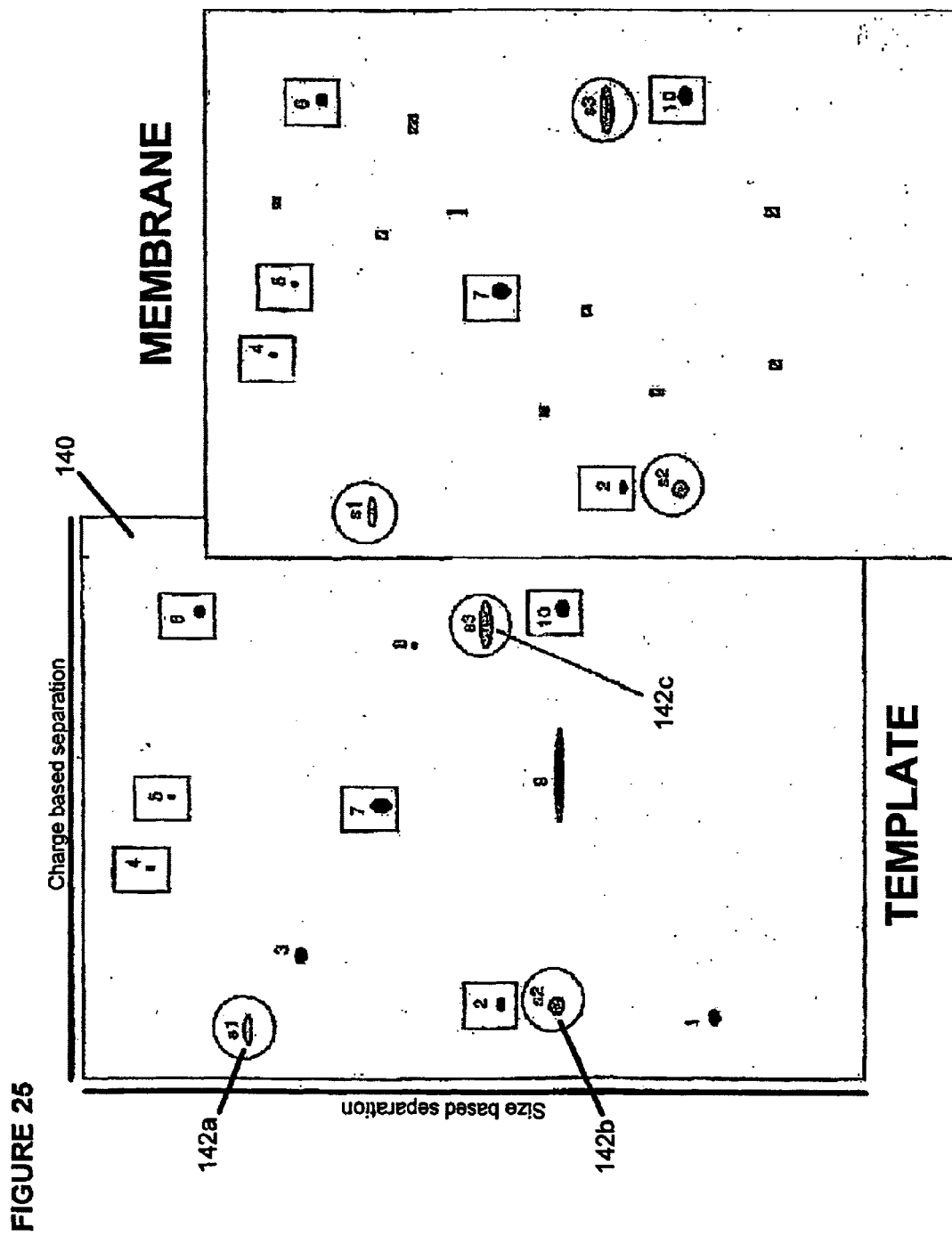
FIG. 25 is a schematic illustration showing a comparison between a template image with a sample membrane.

After it is determined which molecules (e.g., proteins) will be identified on each layer for a given panel/kit, a template image such as that shown for a 2-D gel (reference numeral 140) is created corresponding to each layer (FIG. 25) and stored in software 46. In this example, the 2-D gel X-Y coordinates of each protein can be ascertained from any of a number of references and databases. Thus, referring to FIG. 25, template image 140 is the image of what a membrane would look like if all of the targeted proteins assigned to the layer are present in the sample being tested along with the landmark "housekeeping" proteins 142a, 142b, 142c. Each antibody cocktail generates a unique dot pattern on the corresponding membrane to which it is applied as a result of the selection process outlined above. A template membrane 140 will be used by image processing software to analyze experimental membranes generated by users. Important feature of the template is existence of the internal landmarks 142. These spots will originate from the set of antibodies targeted against housekeeping proteins present in every sample regardless of origin. Since their relationship always stay the same these landmarks will serve to normalize samples for loading differences and to compensate for any distortion caused by gel running process.

Image analysis will start with digitalized image(s) of the experimental membranes. As the first step, the user matches templates with the membranes. Software then compares an image of the template and an image of the membrane and performs alignment of spots/bands. The user has options of visual alignment control and the ability to hand correct minor discrepancies. The second step of analysis will include densitometric readings of the spots on experimental membranes. This data is stored in the database. The third step includes numerical data manipulation. Intensity values of each experimental spot on the membrane are divided with values of the landmark spots. This step generates normalized intensity values for each spot on the membrane. All the spots of interest can thus be compared with each other.

Software 46 preferably allows the user to select the kind of comparative analysis to be performed (i.e. comparing the spots or bands present in one sample with those in another sample or comparing those present on one membrane with those of another membrane within the same membrane stack). Results of the analysis are displayed in, for instance, tabular format and user is given the option to go back and compare magnified sections of the images of interest.

In one embodiment, software is provided with template images corresponding to each of the membrane images. Such software allows the identity of the protein in each spot to be confirmed based upon the vertical and horizontal position of the protein's spot on the gel. Examples of such software also allow the density of each spot to be calculated so as to provide a quantitative or semi-quantitative read-out as described herein. Such software may also have links to a database of images generated from other gels to allow comparisons to be made between different diseased and normal samples, or links to images or data (structure, sequence, function, etc.).

In some embodiments, software is also provided to overlay images of the bands or spots or cells onto a master image of a ubiquitously stained sample or gel. A key feature of examples of such software is the ability to quantify the biomolecules by determining the density of the bands or spots and comparing them to a control. This process is known as "normalization." For analysis of 1-D gels a variety of commercially available programs may be employed such as the 1-D Image Analysis Software available from Eastman Kodak Co.

Having now generally described the invention, the same will be more readily understood through reference to the following examples, which are provided by way of illustration, and are not intended to be limiting of the present invention, unless specified.

EXAMPLES

Example 1

Construction of Polycarbonate Membranes for Protein Binding

Native, non-coated polycarbonate membrane (Millipore, Mass.) has low affinity and low binding capacity for proteins. To improve its protein binding characteristics, polycarbonate membranes were coated with either poly-L lysine (referred to as PC+Lysin in FIG. 26) or nitrocellulose (referred to as PC+NC in FIG. 26). Membranes (177 square centimeters) were immersed for one minute in 5 ml of either aqueous solution of 0.1% poly-L-lysine or 0.1–1.0% nitrocellulose solution in 100% methanol. After coating, membranes were suspended in vertical position and air-dried at room temperature for 5–10 minutes. Poly-L-lysine treated membranes were before use additionally baked for two hours at 50° C. Small squares (0.25 square centimeters) of both treated and non-treated membranes were incubated in TBST solution (50 mM TRIS pH 8.0, 150 mM NaCl and 0.05% Tween-20) with 1.0–100.0 ng/μl of goat immunoglobulin labeled with Cy3 fluorescent dye (Amersham Pharmacia Biotech, USA) for 0.5–2 hours at room temperature.

Figure 26A:
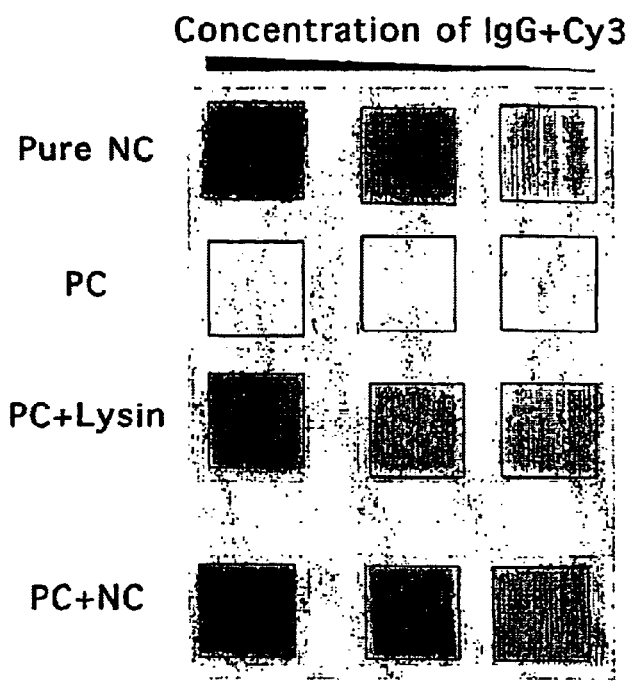
FIG. 26A shows scanned images of the membranes incubated in protein comparing the intensity of signal.
Figure 26B:
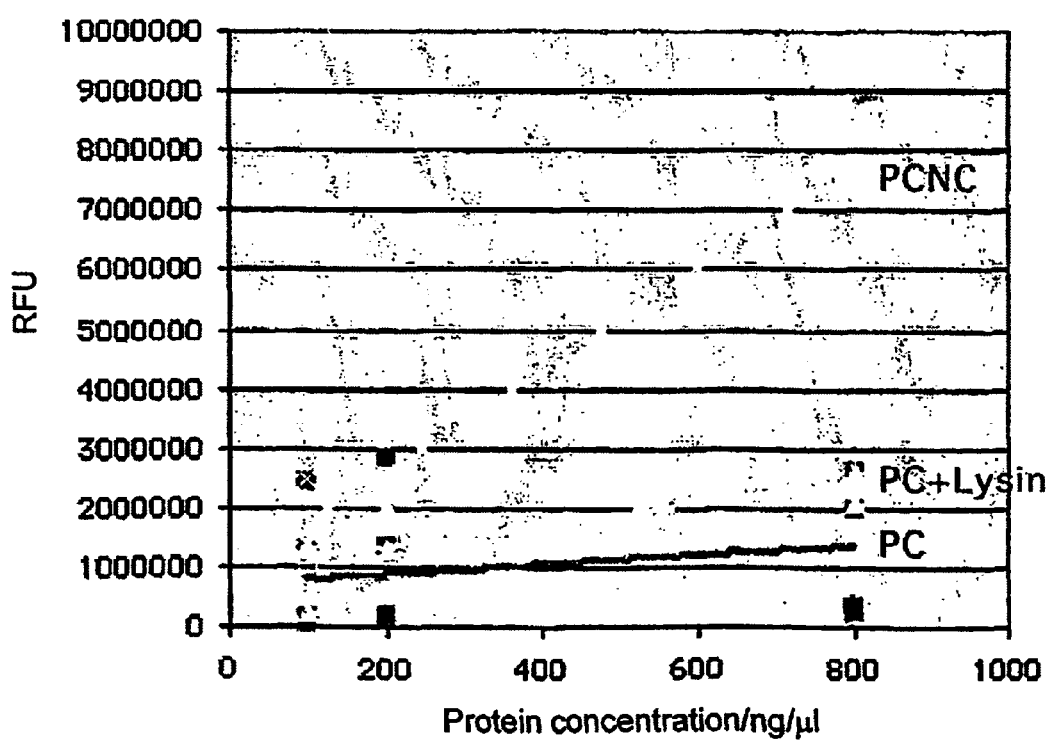
FIG. 26B is a chart plotting the amount of protein bound to different membrane materials.

Membranes were washed in TBST and examined on STORM scanner (Molecular Dynamics, USA). The results are shown in FIG. 26A. The intensity of the signal was quantified by ImageQuant (Molecular Dynamics, USA) and data points from five different experiments were plotted using Microsoft Excel. The results shown in FIG. 26B demonstrate that polycarbonate membranes have a low protein binding potential that can be considerably enhanced by coating the membrane with poly-L-lysine (PC+Lysin) or nitrocellulose (PCNC).

Example 2

Testing the Porosity of Prepared Polycarbonate Membrane Layers

To demonstrate porosity of manufactured layers, native, poly-L-lysine or nitrocellulose coated membranes were blocked in 5% bovine serum albumen solution in 50 mM TRIS pH 8.0 to prevent any protein binding. Fifty-one square centimeter pieces were cut out and stacked together to make a pile. A non-blocked pure nitrocellulose layer was used at the bottom to capture proteins (NC-trap). Three adjacent 20 micrometer thick frozen sections of normal breast tissue were collected on a polycarbonate membrane with 5.0 um pore size and embedded in a 2% agarose gel and transferred side by side through each stack. Between 50 and 100 milliliters of TBST buffer was used per square centimeter of the membrane stack with average length of the transfer being 1 hour. After transfer, proteins remaining in the tissue sections and total proteins on the NC-trap were visualized by Ponceau S staining (SIGMA, Mo.).

Figure 27:
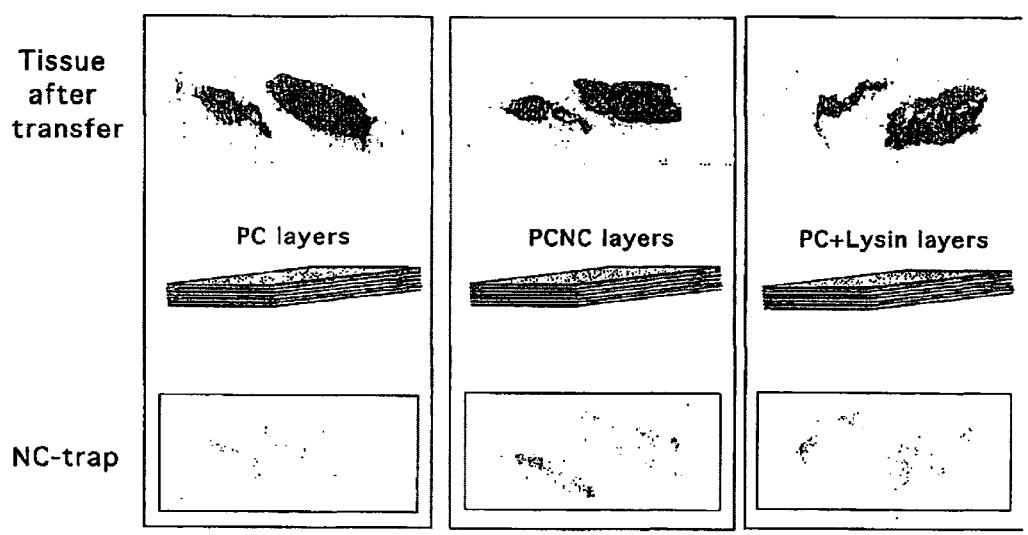
FIG. 27 shows images of tissue sections that show that portions of total biomolecules can be successfully transferred through a stack of polycarbonate (PC) layers onto the trap.
Figures 27A, 27B, 27C:
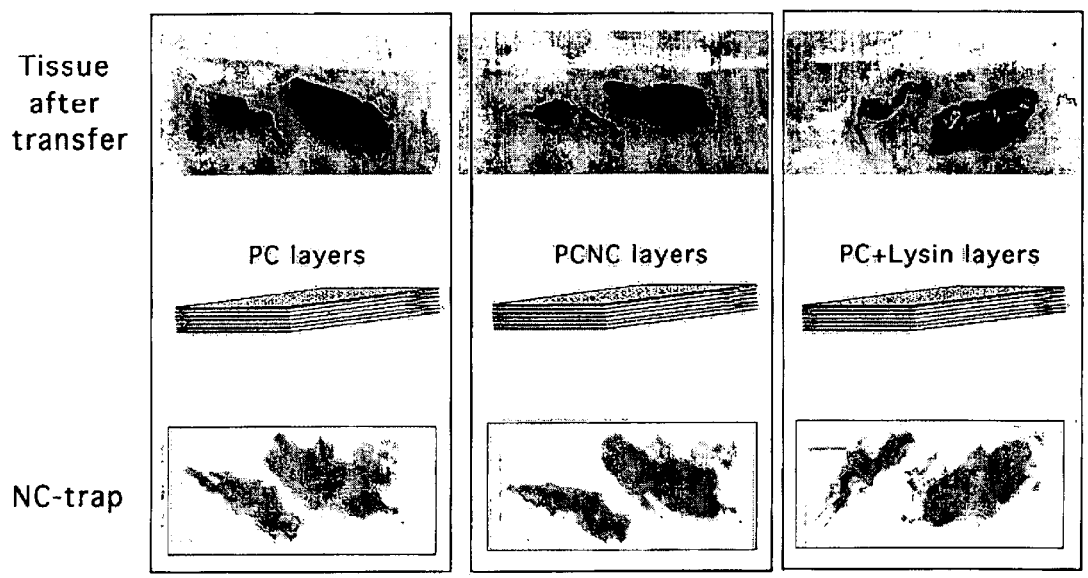
FIG. 27A shows transfer through polycarbonate membranes.
FIG. 27B shows transfer through polycarbonate coated with nitrocellulose.
FIG. 27C shows transfer through polycarbonate coated with poly-L-lysine membranes.

As shown in FIG. 27, the outline of the total proteins transferred through the stack and trapped on the nitrocellulose layer very closely resembled the outline of the applied tissue section. This suggests that not only were membranes porous enough to allow for the proteins to be transferred, but also that at least up to 50 polycarbonate membranes can be used in this kind of assay without apparent distortion of the image due to lateral diffusion.

Example 3

Demonstration of Low Capacity Protein Binding to Nitrocellulose Coated Polycarbonate Layers Examples 1 and 2 demonstrate that proteins in solution can bind to a single nitrocellulose coated polycarbonate layer and that complete saturation of the layer with proteins does not affect its porosity. To ascertain how much of the total protein would be trapped on each individual layer during the tissue section transfer, 20 micron thick frozen sections of normal and tumor breast tissue were placed adjacent to each other on a polycarbonate membrane with 5.0 um pore size, embedded in 2% agarose gel and transferred through 14 layers of nitrocellulose coated polycarbonate to the NC-trap on the bottom, in 100 ml/cm² of buffer containing 25 mM TRIS pH 8.3, 192 mM glycine, 0.05% SDS and 20% methanol. After transfer, proteins left over in the tissue sections were visualized by Ponceau S staining (SIGMA, U.S.A.) and total eluted proteins captured on the NC-trap were visualized by BLOT FastStain (Chemicon, USA). The image formed on the trap demonstrated successful transfer of the protein through the membranes.

To determine whether sufficient total protein trapped on each membrane during the transfer to perform immunological detection 14 arbitrarily selected antibodies were used. Antibodies were: Anti-GAPDH, 1:100 (Chemicon, MAB374); Anti-Rsk, 1:1,000 (Transduction Laboratories, R23820); Anti-Stat5a, 1:500 (Santa Cruz Biotechnology, sc-1081); Anti-IFNalpha, 1:500 (Biosource, AHC4814); Anti-RARalpha, 1:1,000 (Biomol, sa-178); Anti-phospho-EGFR, 1:1,000 (Upstate, 05–483); Anti-non-phospho EGFR, 1:1,000 (Upstate, 05–484); Anti-phospho-NR1, 1:500 (Upstate, 06–651); Anti-Stat1, 1:2,000 (Transduction Laboratories, G16920); Anti-Rb, 1:1,000 (Santa Cruz Biotechnology, sc-50); Anti-Jak1, 1:500 (Santa Cruz Biotechnology, sc-295); Anti-tubulin-alpha, 1:500 (Santa Cruz Biotechnology, sc-5546); Anti-beta-actin, 1:2,000 (SIGMA, A5441).

Figure 28:
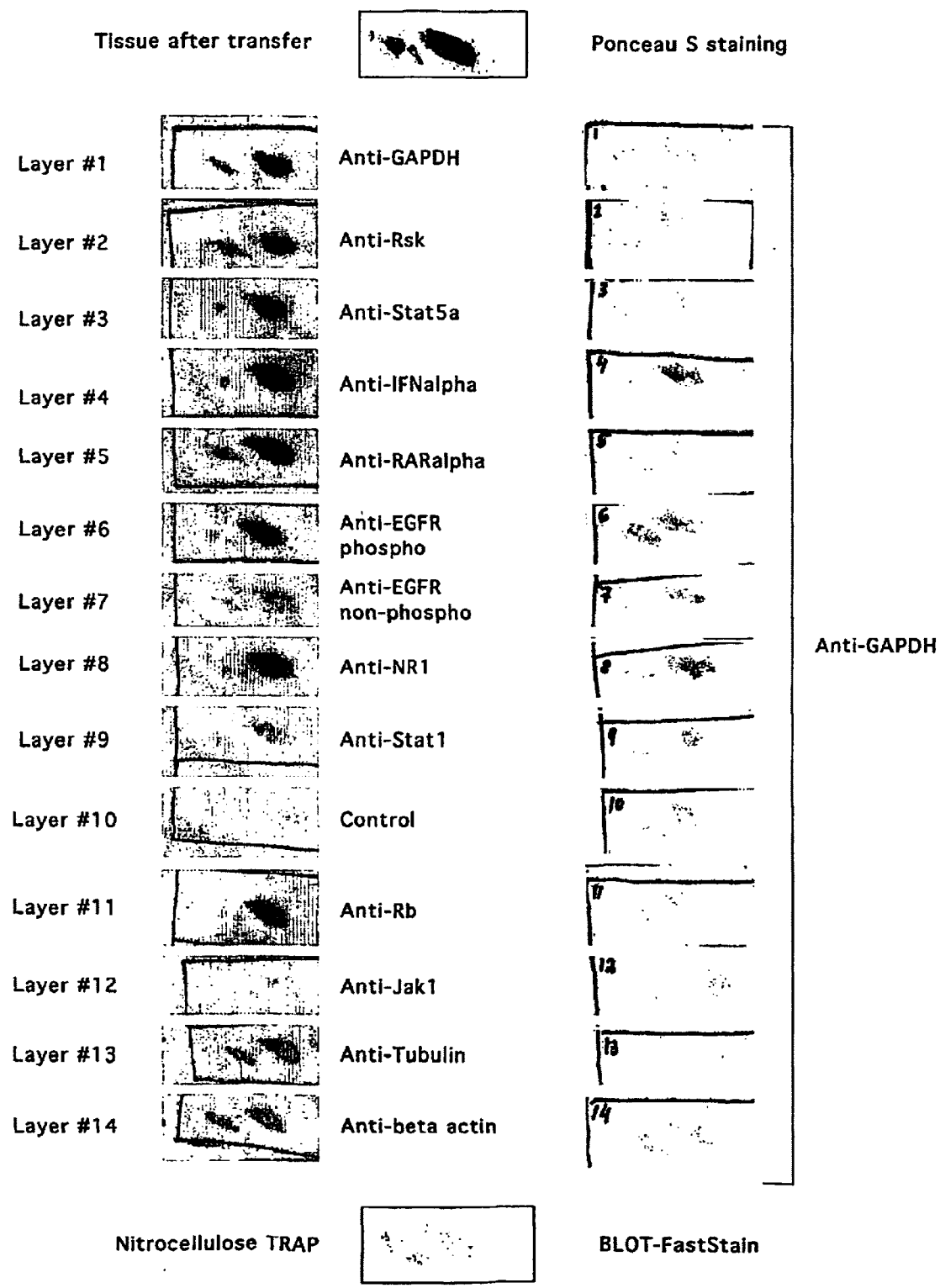
FIG. 28 is a series of images showing immunodetection of different proteins from two regions (healthy and cancerous) of a breast tissue using the membrane array.

Polycarbonate layers were first blocked in 1× casein solution (Vector Labs, U.S.A.) for one hour at room temperature and incubated overnight at 4° C. in primary antibodies as listed in FIG. 28 followed by TBST washes and incubation in alkaline phosphatase (AP) conjugated secondary antibodies (1:2,000 dilution) (Rockland, U.S.A.). Membranes were then incubated for five minutes in enhanced chemiluminescence (ECL) substrate (Vector Labs, USA) followed by visualization of the protein by exposing the membranes to X-ray film (Kodak, USA).

The results showed that methods provided herein allow detection of a number of different proteins. To ascertain how the membranes performed with respect to the amount of total protein captured, the membranes were each incubated with the same antibody, allowing determination of the protein content on each of them. Anti-GAPDH antibody was used for three hours at room temperature, washed in TBST, incubated with anti-mouse secondary antibody conjugated to horseradish peroxidase (HRP) and visualized in enhanced chemiluminescence substrate specific only for HRP (Pierce, USA). After ECL reaction membranes were exposed to film as stated before. The results confirmed that all of the membranes did capture a similar portion of the total protein and differences seen in the first part of the experiment are not the result of differences in membrane "loading." For documentation purposes, the X-ray film was scanned on the flat bed scanner (Lacie, USA) and images were processed using ADOBE PhotoShop 4.0.

Example 4

Transferring Proteins from Tissue Microarrays

A five microns (5 $\mu$M) thick paraffin section of a tissue microarray originating from the National Institutes of Health (NIH) Tissue Array Research Program (TARP) was collected on tape and transferred through four membranes in the manner described above. The membranes were as provided above. The transfer solution contained 50 mM TRIS and 380 mM glycine. This yields a buffer with approximately pH 8.6, but this can be adjusted to anywhere in a range of pH 8.0 to 9.5.

Plastic pouch enclosing membrane stack and tissue array was placed in a Gel Drier (BioRad) and lid of the drier was used as a pressure and heating (80° C.) source. Heat and pressure were applied for two (2) hours.

After transfer, membranes were gently washed in TBST buffer (50 mM TRIS pH 8.0, 150 mM NaCl and 0.05% Tween-20) and stained with FAST Blue Stain (Chemicon) according to manufacturer instructions. Scanning on an Astra 2200 scanner (UMAX) digitalized images of the individual layers. After staining, membranes were rinsed in TBST buffer, blocked for 15 minutes in 1× casein solution (Vector Laboratories, Inc.) and incubated overnight at 4° C. in primary antibody (anti-cytokeratin (1:5,000, Sigma) or anti-PSA (1:500, Script)). The membranes where then washed in TBST, incubated in the complex of secondary antibody and alkaline phosphatase, and washed again. Localization of the target protein (tytokeratin or PSA) was visualized by enhanced chemiluminescence (ECL) (DuoLux, Vector Laboratories, Inc.) and Biomax MR film (Kodak). The images were digitalized by scanning on an Astra 2200 scanner (UMAX).

Figure 29:
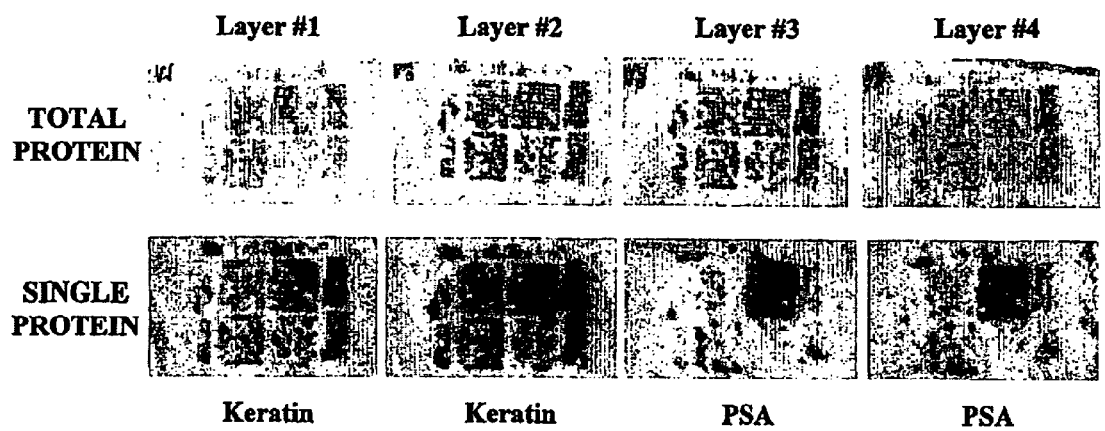
FIG. 29 is a series of photographs of four membrane replicates of a tissue microarray. The top row shows total protein staining of the replicates with a ubiquitous stain; the bottom row shows immunodetection of two specific proteins, keratin and prostate specific antigen (PSA).

The results, shown in FIG. 29, demonstrate that membrane replicas can be made from tissue arrays by using the described techniques without loosing spatial resolution. It also demonstrate that immunodetection of a single protein is possible on these membranes.

Example 5

Differential Protein Expression in Different Tumors

Membrane copies of the TARP array were prepared and assayed as stated in the previous example. For detection, the following primary antibodies were used: anti-cytokeratin (1:5,000, Sigma), anti-PSA (1:500, Script), anti-p53 (1:1,000, Transduction Laboratories) and anti-p300 (1:500, Transduction Laboratories).

Figure 30:
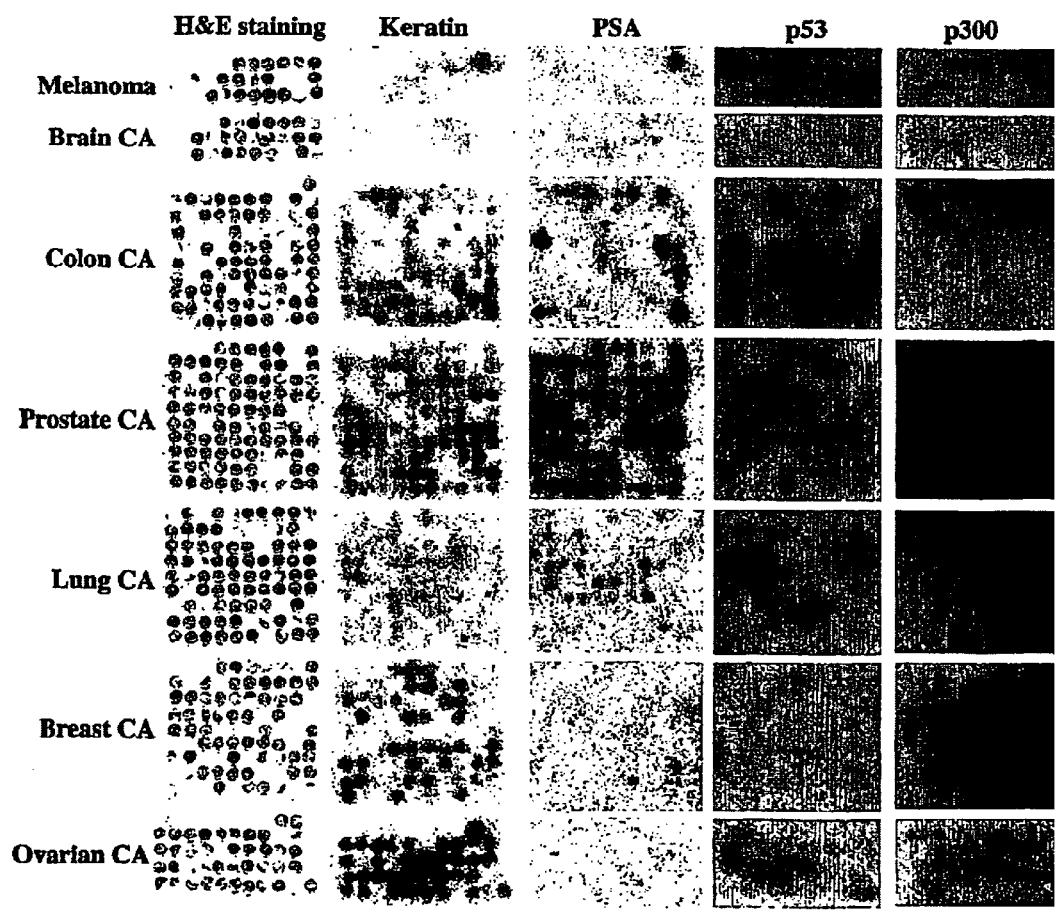
FIG. 30 is a series of photographs showing a tissue microarray before transfer (stained with hematoxylin and eosin (H&E)) and four replicates thereof immunodetected with antibodies to four different proteins (keratin, PSA, p53, and p300) as indicated.

The results, shown in FIG. 30, demonstrate that different tumor types express different amounts of the same protein (for instance, PSA is primarily expressed in the prostate cancer samples) and that the same tumor type can express different amount of the same protein (for instance, p53 and p300 are expressed in only a subset of colon carcinoma samples).

Example 6

Immunodetection on Membranes Using Antibodies Ineffective in IHC

Membrane copies obtained from the transfer of normal human tonsilar tissue, normal human kidney tissue, and TARP tissue array were produced as described in the previous examples. In some cases, the membranes were subjected to antigen retrieval, by immersing them in a solution of 0.1 M sodium citrate containing 10 mM EDTA pH 8, for 5 minutes, at 95° C.

Following blocking in a 1× casein solution (Vector Laboratories) for 30 minutes, the membranes were incubated with monoclonal antibodies diluted at 1:20–1:50 for 16 hours at 4° C. Primary antibodies were used essentially as directed in the manufactures' instructions; each of the antibodies selected are noted by the manufacture to be ineffective when used to detect proteins in formalin preserved tissue samples, even when the samples are subjected to antigen retrieval. The following antibodies were used: anti-CD3 (CALTAG); anti-EGFR; anti-Progesterone Receptor; (Dako); and anti-erbB2 (Zymed). Following TBST washes, proteins were visualized as described in Example 4.

In each case, the antibody yielded clear signals on the transferred membranes but would not yield signals when used for IHC on adjacent sections, directly on a corresponding microarray. Thus, transfer of biomolecules to membranes using the described contact transfer method is effective for immunodetection visualization using antibodies that are ineffective in IHC.

Example 7

Transferring Proteins from Cells Collected by LCM to Membranes

Five microns thick frozen section of squamous carcinoma of the head and neck was collected on plain glass slide. The slide was fixed in 100% ethanol for three minutes, immersed in 0.5% ethanol solution of Azure Blue (SIGMA) for one minute followed by five minutes incubation in xylene. LCM was performed as recommended by the manufacturer (Arcturus). Each LCM cap received approximately 50 laser hits, corresponding to 250–300 cells during a 15–20 minute time period. Immediately after this, caps were stored at −80° C. until transfer.

Just prior to transfer, caps were hydrated through an ethanol gradient and transfer was assembled as shown in FIG. 8. Five different membrane layers were used. Transfer buffer contained 25 mM TRIS, 192 mM glycine and 0.025% SDS. The assembled package was placed in a gel drier (BioRad) and lid of the drier was used as a pressure and temperature (80° C.) source. The transfer process took about two hours.

Figure 31:
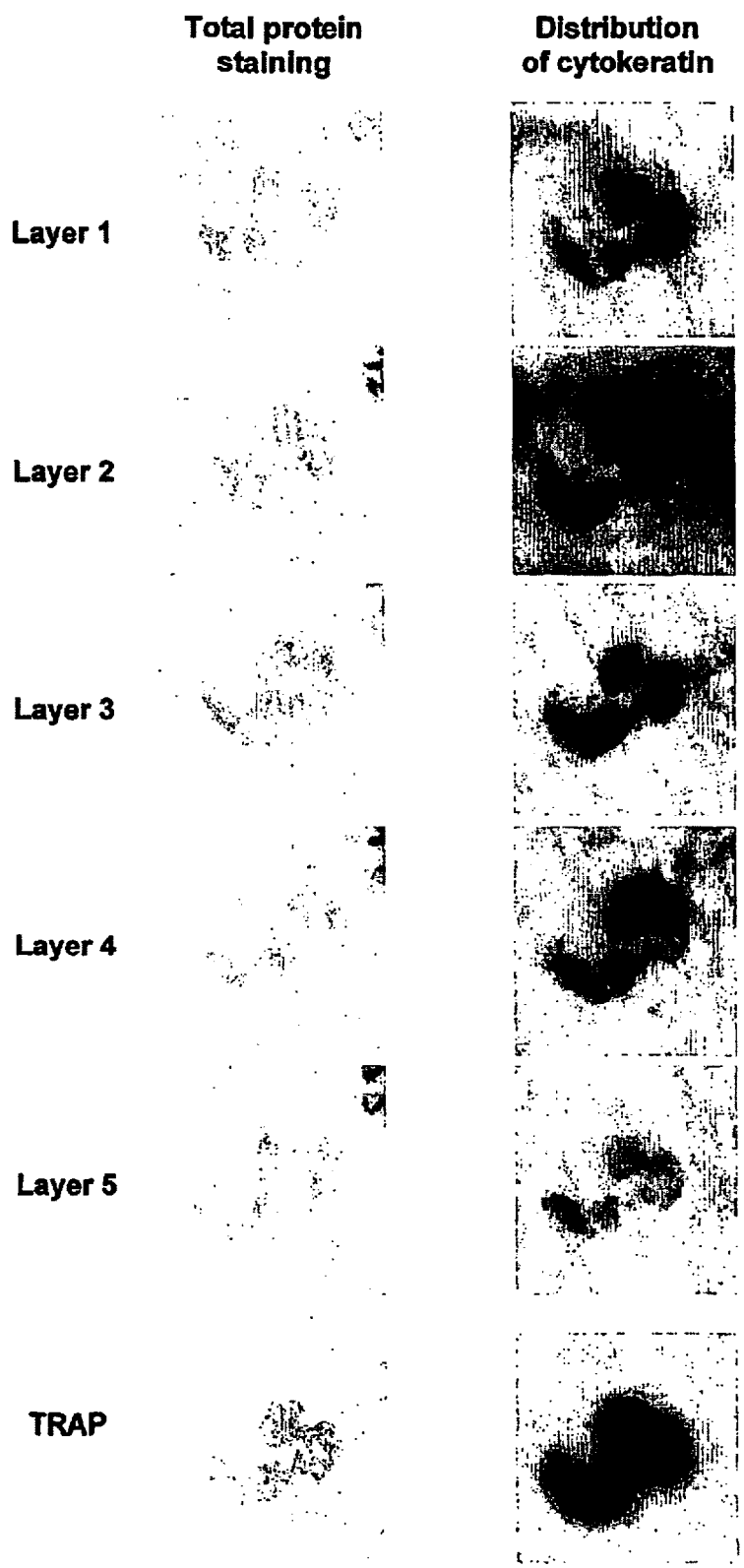
FIG. 31 is a series of photographs showing total proteins captured on the membranes (first column) and immunodetection of cytokeratin (second column).

After transfer, the stack was disassembled, membranes were washed in TBST buffer (50 mM TRIS pH 8.0, 150 mM NaCl and 0.05% Tween-20) and then stained with FAST Blue Stain (Chemicon) according to manufacturer instructions. Scanning on Astra 2200 scanner (UMAX) produced digitalised images of the layers. After staining, membranes were rinsed in TBST buffer, blocked for 15 minutes in 1× casein solution (Vector Laboratories, Inc.) and incubated overnight at +4° C. in anti-cytokeratin antibody (1:5,000, Sigma), washed in TBST, incubated in the complex of secondary antibody and alkaline phosphatase, washed again and location of the protein was visualized by ECL (DuoLux, Vector Laboratories, Inc.) and Biomax MR film (Kodak). The resultant image was digitalised by scanning on an Astra 2200 scanner (UMAX). FIG. 31 shows "copies" that were made on five membranes, and that antibodies were effectively used to detect proteins on each layer.

Example 8

Transfer and Capture of Proteins From a 1-D Gel

This example demonstrates that polycarbonate coated nitrocellulose (PCNC) membranes, with their high binding affinity but low capacity for the proteins eluted from the gel, can be used to make multiple copies of a gel.

1.0 μg/lane of biotinylated protein marker (Vector Laboratories, Inc) was separated by 15% PAGE and electro-transferred in 25 mM Tris, 192 mM glycine, 0.025% SDS and 20% methanol (60–110 V for 1–2 hours) through a stack of PCNC membranes; the number of membranes per stack was 5–20, depending on the experiment At the end of the stack, one pure nitrocellulose membrane was used to capture proteins that were not bound to PCNC layers ("NC trap"). Transfer was performed from 0.5–3 hours at 60–110 V in a Ready Gel Cell apparatus (BioRad).

Figure 32:
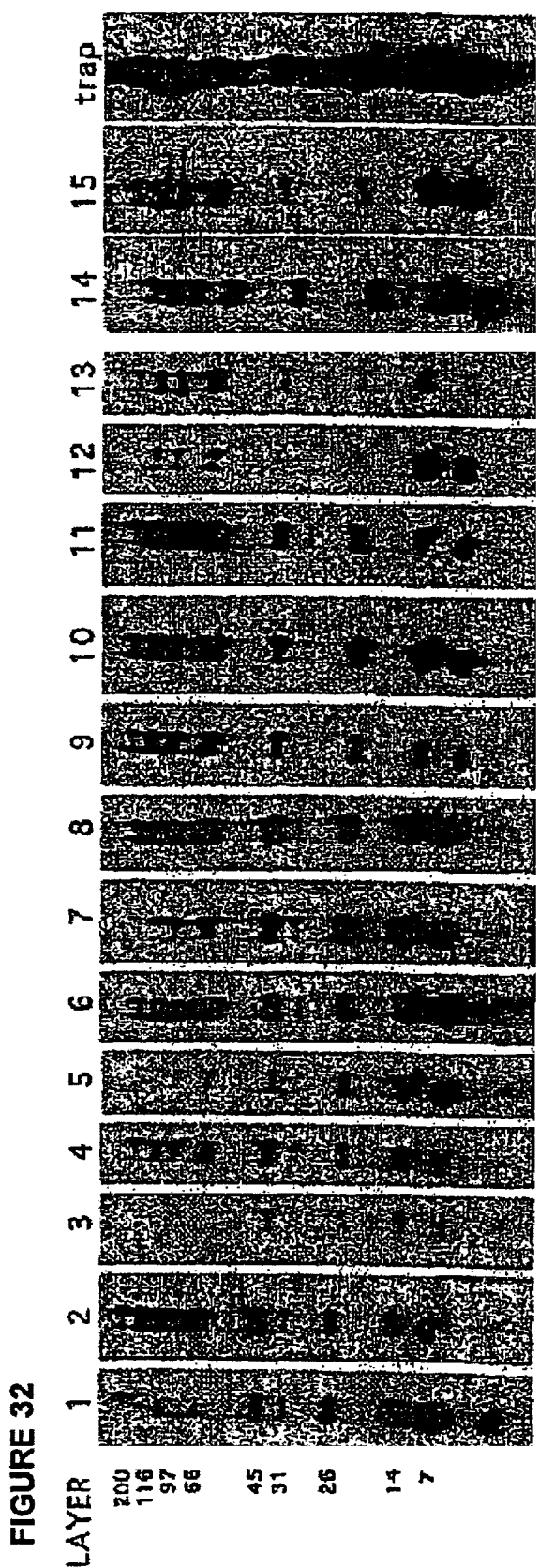
FIG. 32 is a photograph of images of the membranes with biotinylated protein bound to them. Proteins were separated by 1-D PAGE, transferred through the membrane stack and visualized with streptavidin-alkaline phosphatase complex (strep-AP) and enhanced chemiluminescence (ECL) reagent.

After transfer, membranes were rinsed in 50 mM Tris pH 8.0 and 150 mM NaCl (TBS buffer), blocked for 10–60 minutes in 1× casein solution (Vector Laboratories, Inc.), and incubated for 30 minutes in VECTASTAIN ABC-AmP reagent (Vector Laboratories, Inc.). Membranes were washed again in TBST, rinsed in 0.1 M TRIS pH 9.5, incubated in DuoLux reagent (Vector Laboratories, Inc.) for 3–5 minutes, and exposed to Biomax MR film (Kodak). An example of one representative experiment is shown in FIG. 32.

Results demonstrated that:
1. PCNC stack of membranes did not interfere with post-transfer Western blotting procedure—proteins were transferred from the gel through the stack and to the NC trap;
2. A wide range of protein sizes were transferred through the stack with very similar transfer efficiency—7 kDa-200 kDa proteins were detected on the NC trap; and
3. PCNC layers captured proteins regardless of their size.

In order to determine compatibility of PCNC membranes with immunodetection, Jurkat cell were lysed in buffer (50 mM TRIS pH 8.0 and 1% SDS) and 20 μg/lane of total protein was separated by 15% PAGE. The resultant gel was electro-transferred through a stack of PCNC membranes in 25 mM TRIS, 192 mM glycine, 0.025% SDS and 20% methanol. Transfer was carried out at 60–110 V for one to two hours.

Figure 33:
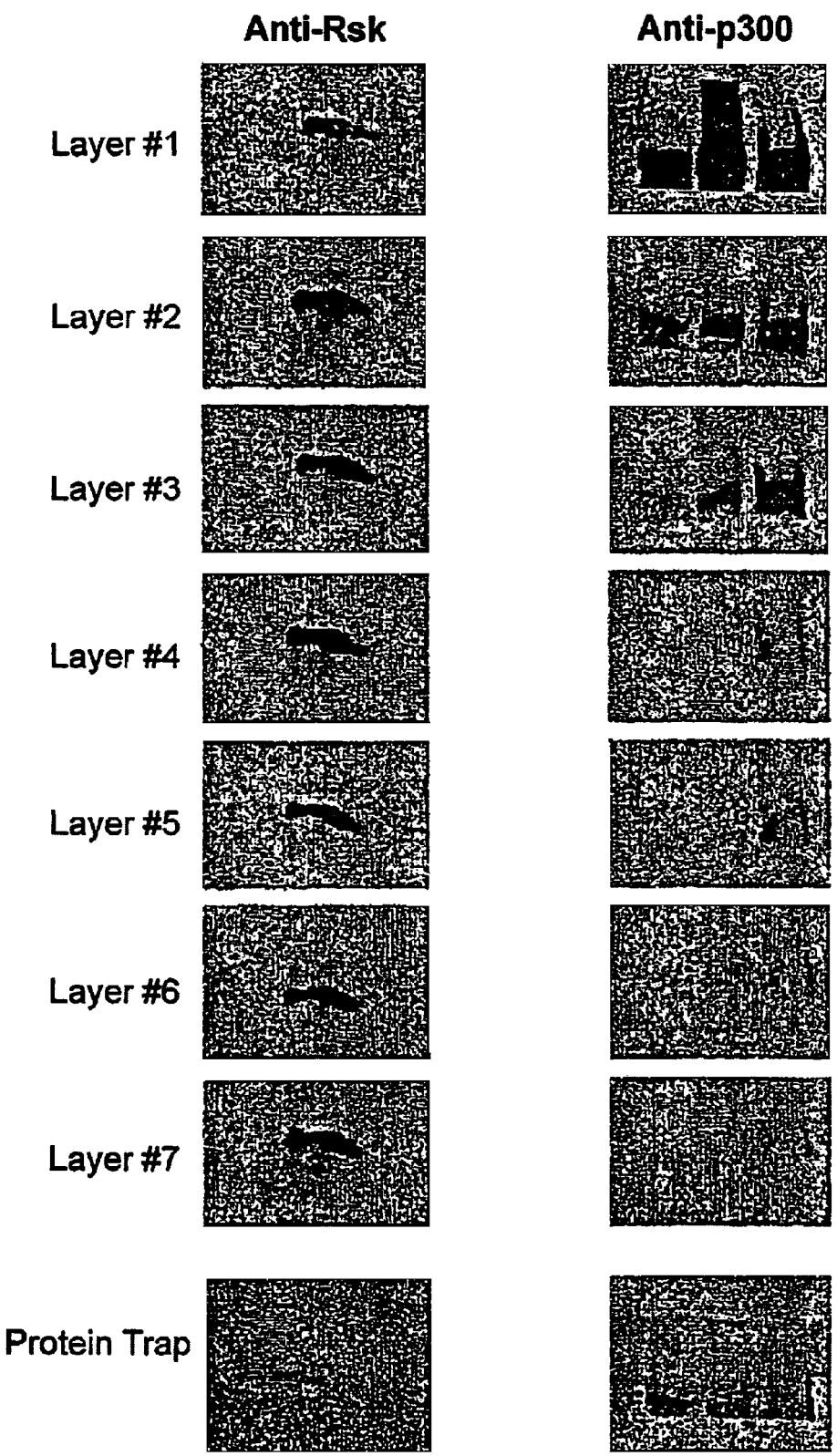
FIG. 33 is a photograph of images of the membranes with Rsk and p300 proteins bound to them. Protein separation and blotting was performed as stated in FIG. 15.

All of the membranes were incubated in primary anti-Rsk (1:100, Transduction Laboratories) and anti-p300 (1:500, Transduction Laboratories) antibody, washed in TBST buffer, incubated with the complex of secondary antibody and alkaline phosphatase, and washed again. The location of the protein on the blots was visualized using ECL (DuoLux, Vector Laboratories, Inc.) and Biomax MR film (Kodak). The results, shown in FIG. 33, demonstrated that PCNC membranes are suitable for this type of protein detection. Each membrane captured sufficient protein to be detected by immunological methods, but each single membrane did not capture too much protein, enabling a number of copies of the same gel to be generated.

Example 9

Transfer and Capture of Proteins From a 2-D Gel

2-D protein gels have greater separation capabilities than 1-D gels. Two-dimensional separation allows identification of hundreds or even thousands of proteins on the same gel. Proteins separated by 2-D gels are identified by protein sequencing or immunological features. Sequencing requires expensive equipment, highly trained operators, and its use is limited to a small number of privileged groups. Immunodetection is easier to do but it is a low throughput technique, since traditional blotting procedures generate only one membrane per gel.

As described above, one can make 10 or more 1-D gel copies using PCNC membranes. In order to find out if 2-D gels can be "copied" the same way, the proteins present in 500 μg of Jurkat cell protein lysate were separated by 2-D PAGE. A commercial immobilized pH gradient (IPG) from 3.0 to 10.0 (Pharmacia Biotech, Uppsala, Sweden) was used for first-dimension separation. Eight to 12 hours of in-gel sample rehydration was used for protein loading. Proteins were separated for a total of 15,000–30,000 Vhrs. After equilibration, the IPG strips were transferred onto vertical gradient gel (4–20%, Novex) for second dimension separation.

After electrophoresis, the 2-D gel was transferred in 25 mM Tris, 192 mM glycine, 0.025% SDS and 20% methanol (60–110 V for 1–2 hours) through a stack of five PCNC membranes. The membranes were then rinsed in TBST buffer, then blocked for 10–60 minutes in 1× casein solution (Vector Laboratories, Inc.) prior to probing with specific antibodies. Individual membranes were probed by incubating them overnight at 4° C. in anti-GAPDH (1:5,000, Chemicon), anti-beta-actin (1:5,000, Sigma) and/or anti alpha-tubulin (1:1,000, Calbiochem) antibody. The membranes were then washed in TBST, incubated in the complex of secondary antibody and alkaline phosphatase, and washed again. The location of the protein was visualized by ECL (DuoLux, Vector Laboratories, Inc.) and Biomax MR film (Kodak).

Antibodies were first applied separately to three different membranes (from three different gels) to find the precise spatial location of specific proteins in the 2-D gel. These three proteins (GAPDH, actin, and tubulin) differ in their size and charge, and were spatially separated from each other on the gel.

Figure 34:
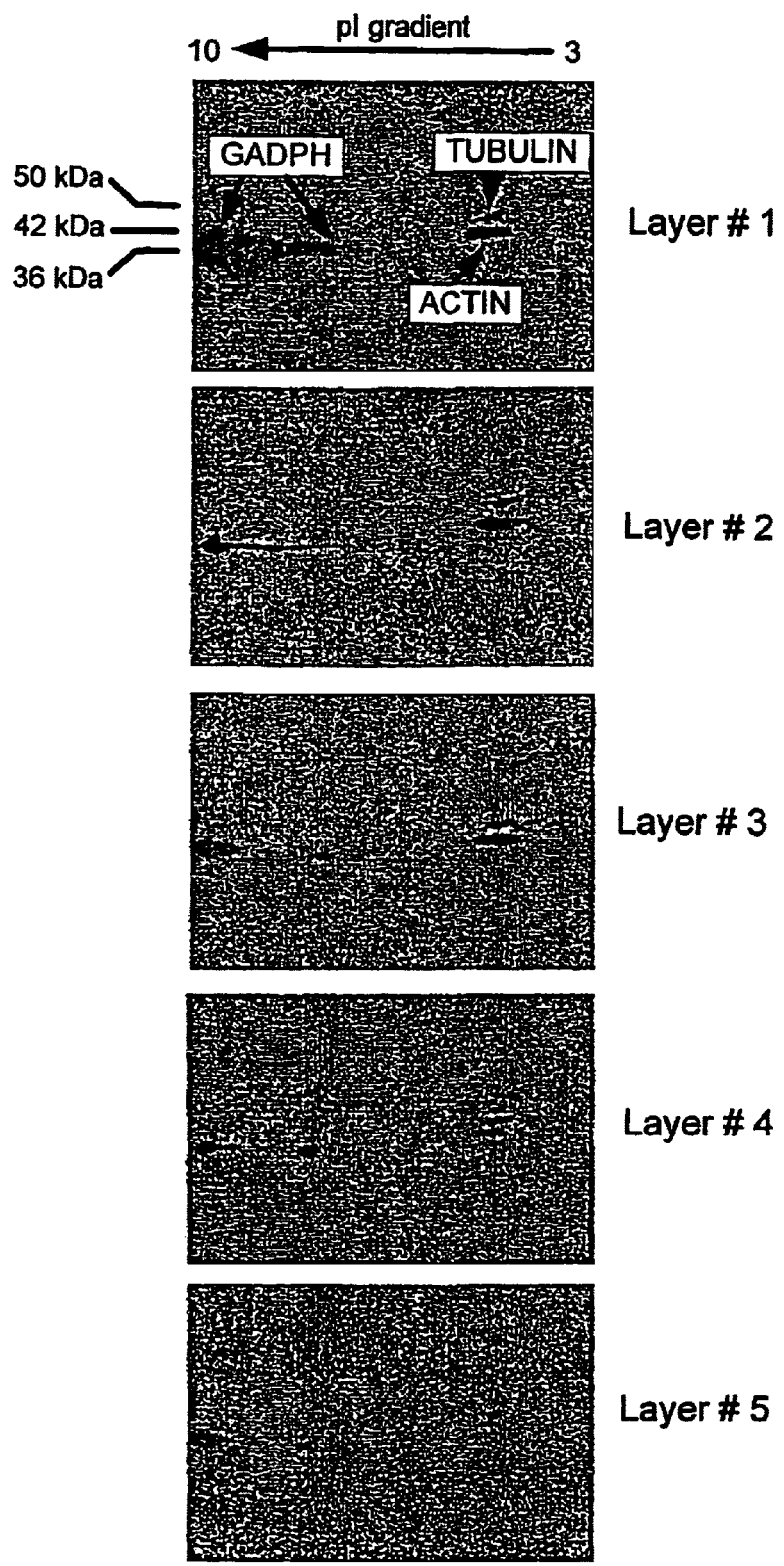
FIG. 34 is a photograph of images of the membranes with GAPDH, Alpha-tubulin and Beta-actin bound to them. Proteins were separated by 2-D PAGE, transferred through the membrane stack and visualized with primary-secondary antibody-alkaline phosphatase complex and ECL reagent.

In order to increase the throughput of immuno-detection, all three antibodies were mixed together and applied as a detector cocktail to all five membranes from the same gel. The results of this experiment are shown in FIG. 34. Generating multiple replicas of the same gel and using an antibody cocktail approach increased throughput of the immunological protein identification on 2-D gels.

Example 10

Use of Layered Membranes for Protein-DNA Complexes Identification

The following example demonstrates the ability of the layered membranes of the present invention to speed up and simplify the identification of the proteins of a protein-DNA complex. It shows that copies of the gel were made and each of the membranes was successfully immuno-probed with a different antibody of interest.

250 ng of recombinant his6-c-rel and 120 ng of purified recombinant his6-CREB were incubated alone or in combination with 0.2 ng of $^{32}$P-5' labeled duplex oligonucleotide (SEQ ID NO: 1), in 10 μl of buffer containing 10 mM HEPES, 50 mM NaCl, 20% glycerol, and 4 mM βME. The hybridization reaction was allowed to proceed at room temperature for 30 minutes. Samples were separated by electrophoresis on 4% polyacrylamide gel at 180 Volts for one hour, then transferred in 25 mM TRIS, 192 mM glycine, 0.025% SDS and 20% methanol (60–110 V for 1–2 hours) through a stack of four PCNC membranes (as described herein) and one NA45 DEAE membrane (Schleicher & Schuell). This last layer of charged cellulose was used to trap DNA released from the gel that transferred through the entire thickness of the stack. After transfer, registration (orientation) marks were made using a 19G needle. The DEAE membrane was dried, exposed overnight to a phosphoimager screen, and visualized on a Phosphorimager: SI (Molecular Dynamics).

Figure 35:
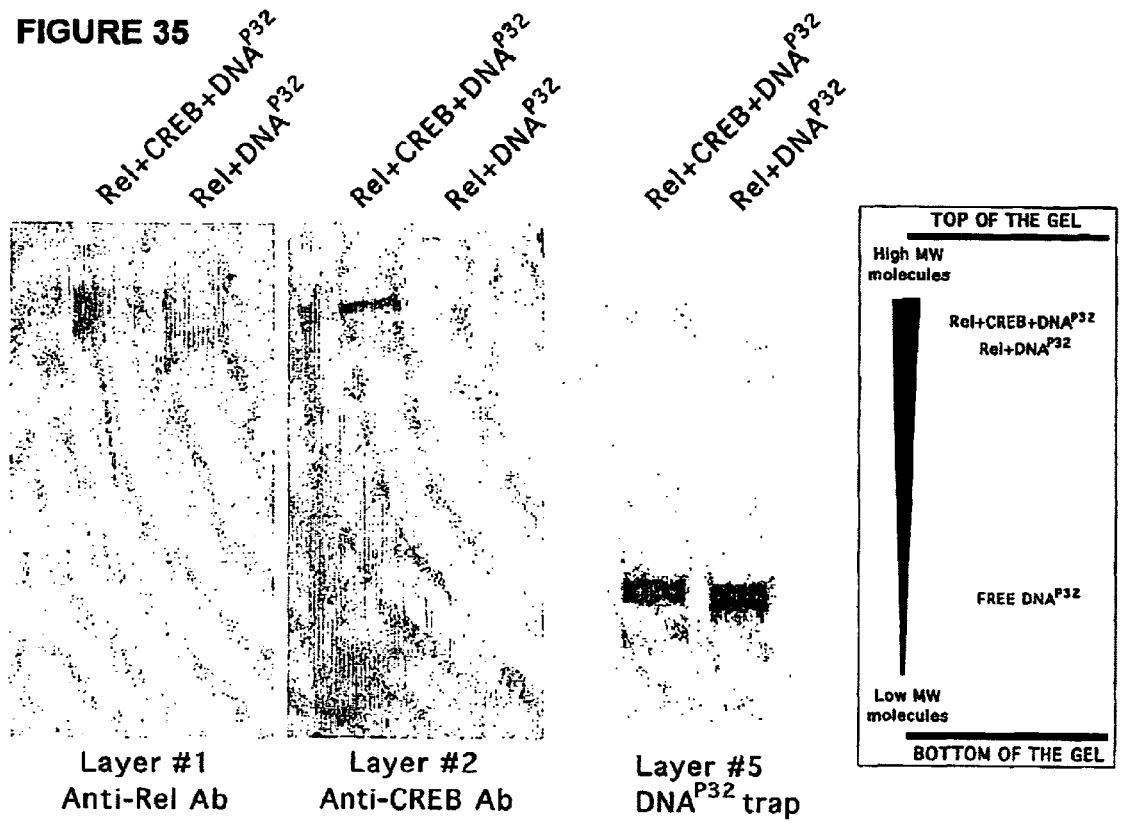
FIG. 35 is a photograph of images of the membranes with protein or DNA attached to them and a diagram that explains the relationship between different protein-DNA complexes and their position in the gel.

First and second PCNC membranes were rinsed in TBST buffer, blocked for 10–60 minutes in 1× casein solution (Vector Laboratories, Inc.) and incubated overnight at 4° C. in anti-rat antibody (1:200, NCI Laboratory of Pathology, Transcription Regulation Unit Chief, Dr. Kevin Gardner) and anti-His (1:10,000, Stratagene). The membranes were washed in TBST, incubated in the complex of secondary antibody and alkaline phosphatase, then washed again. The location of the specific proteins was visualized by ECL (DuoLux, Vector Laboratories, Inc.) and Biomax MR film (Kodak). Images of all of the membranes were aligned in Adobe Photoshop (FIG. 35).

The results demonstrated that the layered membrane array provides fast and reliable identification of proteins from a protein complex.

Example 11

Uniformity of Protein Capture on Multiple Membranes

During electrotransfer, proteins are pushed (or pulled) out of the gel onto the membrane substrate. The speed of their migration is influenced by the magnitude of the electric current and size of the protein. A higher voltage will push proteins out of the gel faster then a lower voltage. Even with fixed current flow, smaller proteins generally move faster then larger ones. The length of the transfer is another variable that can influence quality of membrane copies. If transfer is too short, not enough of the protein will leave the gel and be accessible for binding onto the membranes.

An analysis of the results obtained with the methods and materials described herein indicates that, regardless of the amount of protein that is present in the gel, more uniform membrane copies can be generated if transfer is performed for shorter time with higher voltage. All of the transfers in this Example are performed for 60–70 minutes at 59–63 volts. Keeping the transfer conditions constant, the influence of protein load amount on the ability to create membrane copies was examined.

Total protein extracted from the Jurkat cell line (cells of lymphatic origin), the HN12 cell line (epithelial cells of keratinocyte origin) and the SW480 cell line (cells of adeno-epithelial origin) were used for this Example. All cell lines were cultured in a 37° C. humidified incubator in DMEM media with 10% added serum. At about 80–90% confluence, cells were harvested by scraping them from the dish; the cells were then resuspended in phosphate buffered saline (PBS) with 1% added SDS. The concentration of the total protein was determined by BCA Protein Assay Reagent (Pierce). Approximately 30–100 micrograms of total protein was separated by 4–20% polyacrylamide gel electrophoresis (PAGE) (BioRad). A suitable protein gel running buffer was used in the electrophoresis to separate the proteins (for instance, 25 mM TRIS pH 8.3, 192 mM glycine, 0.1% SDS). In addition, protein size markers (Bio-Rad Kaleidoscopic Standard, catalog number 161–0324) were loaded on the gel.

After electrophoretic separation, proteins were transferred through a 10-layered array by electroblotting (Bio-Rad catalog number 170–3930). A fiber pad, or more than one fiber pad was used at the anode and the cathode during electroblotting. Thus, starting from the cathode side of the electroblotting cassette, the fiber pad (on the bottom of the sandwich), filter paper, gel, and membrane stack are layered in order, with one membrane (the first membrane, denoted membrane "1") in contact with the gel. When assembled, the electroblotting cassette tightly squeezes the "transfer sandwich" (unlike a single membrane transfer, which can be gently squeezed). Fiber pads may be added on the outside of the sandwich umtil the cassette seems "overfilled." When the sandwich has the proper thickness, it may be necessary to force the cassette closed.

The electroblotting procedure will vary depending on the system used (for Bio-Rad devices, transfer is accomplished at 59–63 volts for 60–70 minutes; for Novex devices, transfer is accomplished at 25 volts for 120 minutes). To facilitate later labeling of individual membranes, holes can be punched (for instance, using a 23 g–25 g needle) distinguishable locations, such as in the center of each protein standard band, and in the center of each well.

After transfer, the membrane stack was removed from the gel by gently peeling up one corner, and the frames were opened or removed. The membrane stack was then washed in Tris or phosphate buffered solution, and the membranes separated while they are still in the solution. Before immunodetection, the membranes are immersed in Blocking Reagent (20/20 GeneSystems) for 15 minutes.

Membranes were separately stained with Sypro Ruby (Molecular Probes) as recommended by the manufacturer and visualized on an Image Station 440CF (Kodak). Fluorescence intensities were taken from three different regions of every sample on every membrane using KODAK ID Image Analysis Software (Kodak). The first region included proteins from 20–40 kDa in size. The second region included proteins from 40–100 kDa in size. The third region included proteins 100-150 kDa in size. The relationship between different groups was analyzed using Microsoft Excel®.

Figure 36:
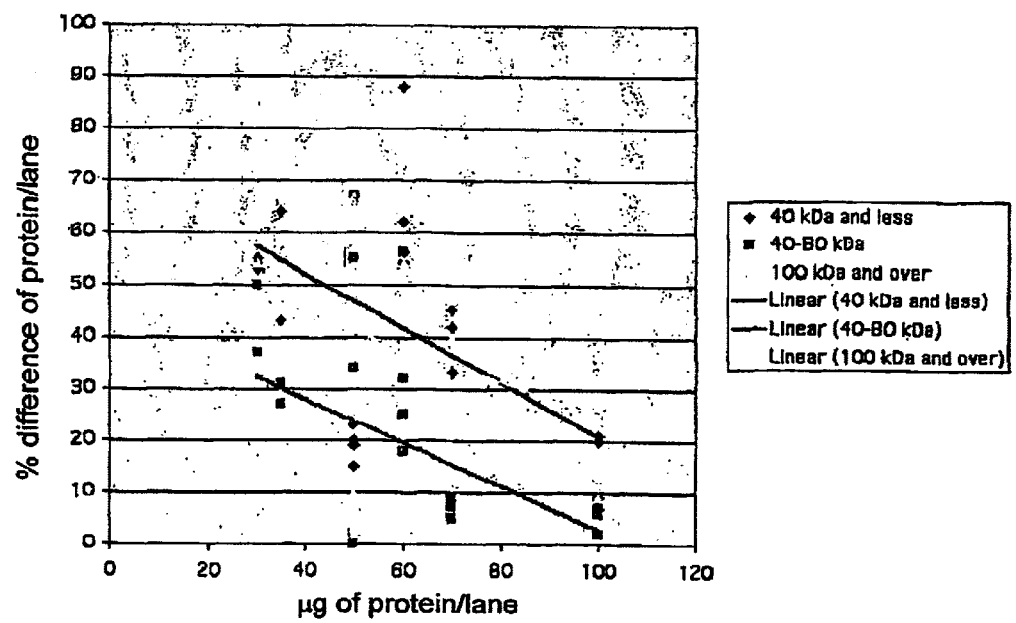
FIG. 36 is line graph showing the relationship between protein loading on the gel, protein size, and uniformity of transfer to the membranes.

A data plot (FIG. 36) demonstrates that the smallest variability in total protein loading per membrane was seen for proteins 40–100 kDa in size. The data also suggest that the amount of protein loaded was an important variable in this system. For proteins that are 40–100 kDa in size, it was determined that loading of 70–100 µg per lane kept variability between the membranes in the less than 10% range.

Example 12

Detecting Presence and Functional State of Multiple Proteins Separated on a Single Gel To determine the feasibility of detecting the presence and functional state of multiple proteins from the same gel, the presence and functional state of EGFR and c-myc protein was checked in parallel. Samples used were from the Jurkat cell line, HN12 cell line, and SW480 cell line; cells were cultured and harvested as stated in Example 11. Thirty micrograms of total protein was loaded per lane of 4–20% polyacrylamide gel (BioRad) and separated for two hours at 50 V. After electrophoresis, the gel was equilibrated for 10 minutes in 1× transfer buffer from 20/20 Gene Systems, Inc. and electrotransfer was assembled with a seven-layered membrane stack (20/20 Gene Systems, Inc). A MiniCell blotter (BioRad) was used for the electrotransfer. Transfer was performed for 60–70 minutes at 59–63 V. After transfer, membranes were separated in 50 mM Tris pH 8.0, 150 mM NaCl and 0.05% Tween-20 (TBST), blocked in 1× casein solution (Vector) for 15 minutes at room temperature and incubated with antibodies diluted in TBST as indicated in TABLE 1 for 12 hours at 4° C.

TABLE 1

| Layer Number | Protein | Manufacturer | Part Number | Ab Dilution |
|---|---|---|---|---|
| 1 | Total EGFR | Neomarker | MS-610 | 1:500 |
| 2 | Total EGFR | Santa Cruz | SC-03 | 1:200 |
| 3 | Phospho-EGFR | Upstate | 05-484 | 1:1,000 |
| 4 | Phospho-EGFR | Upstate | 05-483 | 1:1,000 |
| 5 | Total c-myc | Santa Cruz | SC-764 | 1:200 |
| 6 | Total c-myc | Neomarkers | MS-127 | 1:500 |
| 7 | Phospho-myc | Cell Signaling | 9401L | 1:1,000 |
| 1–7 | Alpha-tubulin | Calbiochem | CP06 | 1:500 |

After incubation with primary antibody, each membrane was washed separately three times for five minutes each in TBST and incubated in 1:4,000 dilution of horseradish peroxidase (HRP) conjugated secondary antibody (Amersham) in 1× casein solution for 30 minutes at room temperature. Membranes were then washed for five minutes in TBST and twice for five minutes each in 50 mM TRIS pH 8.0, 150 mM NaCl (TBS), incubated for five minutes in ECL PLUS substrate (Amersham) and exposed to Biomax MR film (Kodak) from 1–45 minutes.

The image of the film was digitized on an Astra 2200 scanner (Umax) and manipulated in ADOBE Photoshop 5.0. Following incubation in the first set of antibodies, all of the membranes were incubated in anti-alpha-tubulin antibody for two hours at room temperature and signal visualized as stated above, with the exception that the secondary antibody was conjugated with alkaline phosphatase (AP) (Vector) and the ECL reagent used was DuoLux (Vector).

Figure 37:
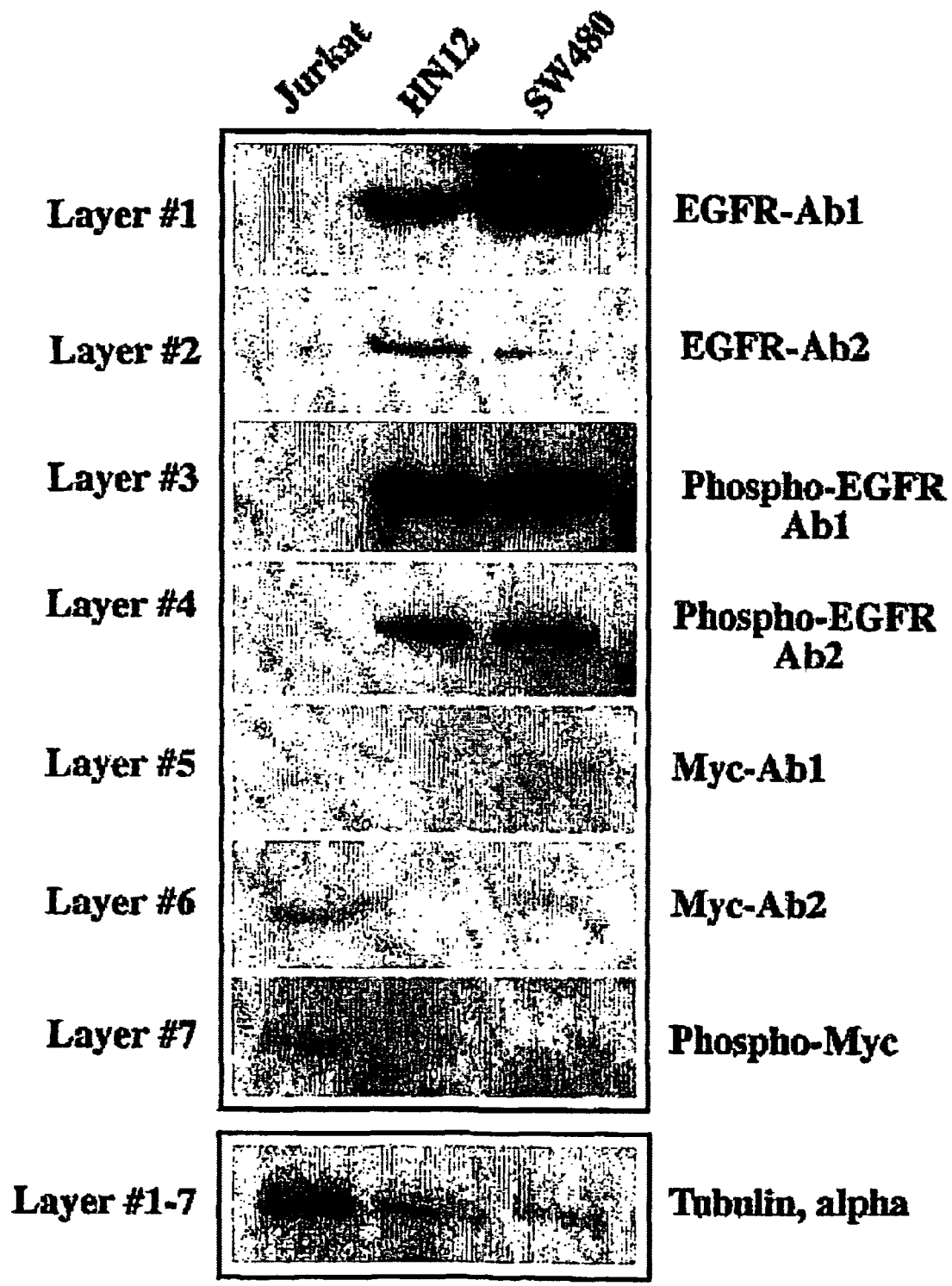
FIG. 37 is a photograph showing differential expression of gel-separated proteins from three cell samples (Jurkat, HN12, and SW480) blotted onto a seven-layer stack of membranes.

The result of this Example, shown in FIG. 37, demonstrated that multiple membrane copies made from the same gel could be used to determine the presence and functional state of multiple proteins from the same sample: In this Example, both total and activated forms of EGFR and c-myc protein were detected in extracts prepared from the SW480 cell line. Results also demonstrated that different samples could be compared to each other to reveal the presence of total protein (for instance, EGFR was expressed in HN12 and SW480 cells, but not in Jurkat cells) and that the presence of total protein does not necessarily mean functional activity (c-myc was present in both Jurkat and SW480 cell lines but only Jurkat cells had an active, functional form).

Example 13

Detecting Proteins Involved in Epidermal Growth Factor Receptor (EGFR) Signaling Pathway Advantages of certain of the encompassed embodiments include that they permit analysis and comparison, in parallel, of a number of different proteins from multiple samples. The value of this parallel approach is even greater where the proteins of interest belong to a single biological system (e.g., all are component s of a receptor signaling pathway). Since analysis for all of the proteins is done on a single sample, comparative studies are easier to perform, and it is expected that the results are more consistent and reliable.

In this Example, the functional state of nine proteins that are involved in signaling through the EGFR pathway were analyzed and compared. Four different keratinocyte cell lines were cultured and harvested as described above (see Example 11). One hundred micrograms of total protein from each cell line was separated on a 4–20% acrylamide gradient gel (BioRad) and transferred through a ten-layered array as described above (see Example 11).

Membranes were stained with the ubiquitous dye Sypro Ruby (Molecular Probes) and images captured and stored on Image Station 440CF (Kodak). Following visualization of the total protein, membranes were blocked in 1× casein solution (Vector) for 15 minutes at room temperature, then incubated with antibodies diluted in TBST as indicated in TABLE 2 for 12 hours at 4° C. The control membrane layer was incubated in no primary antibody.

TABLE 2

| Protein | Manufacturer | Part Number | Ab Dilution | Detected |
|---|---|---|---|---|
| Phospho-Raf | Biosource | 44-504 | 1:1,500 | Yes |
| Phosho-Akt | Cell Signaling | 9276S | 1:1,000 | Yes |
| Phosho-Erk | Cell Signaling | 9106S | 1:1,000 | Yes |
| Phosho-Myc | Cell Signaling | 9401L | 1:1,000 | Yes |
| Phosho-EGFR | Upstate | 05-493 | 1:1,000 | Yes |
| Total EGFR | Neomarkers | MS610 | 1:500 | Yes |
| Phospho-Stat3 | Biosource | 44-384 | 1:1,000 | Yes |
| Phospho-PKC | Cell Signaling | 2261 | 1:1,000 | No |
| Phospho-Src | Biosource | 44-660 | 1:1,000 | Yes |

Following incubation with primary antibodies, membranes were processed as described above (see EXAMPLE 12).

Figure 38:
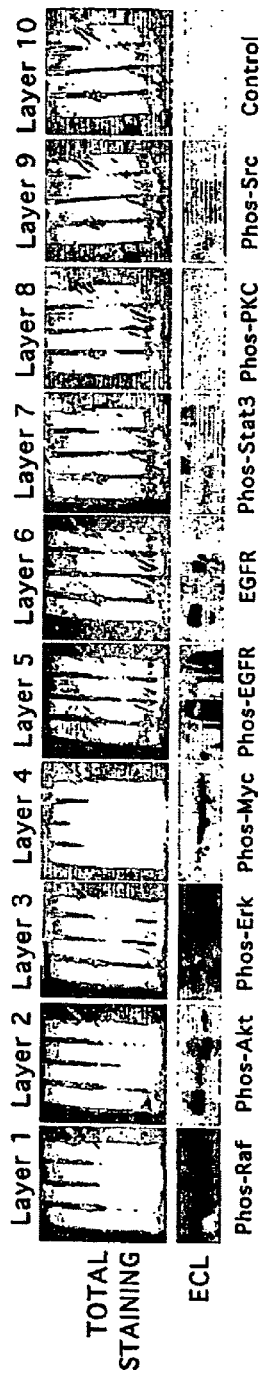
FIG. 38 is a photograph showing differential expression of gel-separated proteins from four cell samples blotted onto a ten-layer stack of membranes. The upper row (marked "Total Staining") shows the membranes stained ubiquitously with a dye. The bottom row (marked "ECL") shows the membranes probed with the indicated antibodies.

FIG. 38 shows that eight of the nine proteins tested could be detected on the stacked membranes using this method. The phosphorylated form of PKC was not detected in these samples. Follow up experiments also failed to detect this form of protein when the same amount of sample was blotted on single nitrocellulose membrane with positive control cellular extract being positive (PDGF treated 3T3 cells, 10 μg/lane, provided by Cell Signaling). This suggests that the failure to detect the phosphorylated form of PKC was not due to a deficiency in the transfer system but to the very small (if any) amount of this protein present in the tested cell lines. The results also clearly illustrate differential expression between different cell lines for all of the proteins tested.

Example 14

Contact Transfer of Proteins From a 1-D Gel

Diffusion based transfer of proteins from an acrylamide gel onto single membrane substrate was previously discussed by Bowen et al (*Nucleic Acid Res.*, 8:1–20, 1980). The apparent advantage of this system is that it does not require special blotting equipment. This Example was carried out in order to determine if it is possible to use contact transfer (without applying an electric current) with the provided membrane arrays.

A 10% gel (BioRad) with 25 and 50 micrograms of total protein was sandwiched between two five-membrane membrane stacks as shown in FIG. 6, with five membranes on each side of the gel. Three layers of Whatman® filter paper soaked in 1× transfer buffer from 20/20 Gene Systems, Inc. were added on each side of the sandwich and the whole, assembled stack was sealed in a plastic bag. Three parallel sample stacks were assembled and placed in a gel drier (BioRad) with the lid closed at 80° C. Individual sample stacks were removed after 30, 60 or 120 minutes of transfer. After transfer, the membranes were washed in TBST and stained with FastBlue Stain (Calbiochem) as recommended by the manufacturer. Stained membranes were scanned using an Astra 2200 scanner (Umax) to detect total transferred protein, and the images were manipulated in ADOBE Photoshop 5.0.

Figure 39:
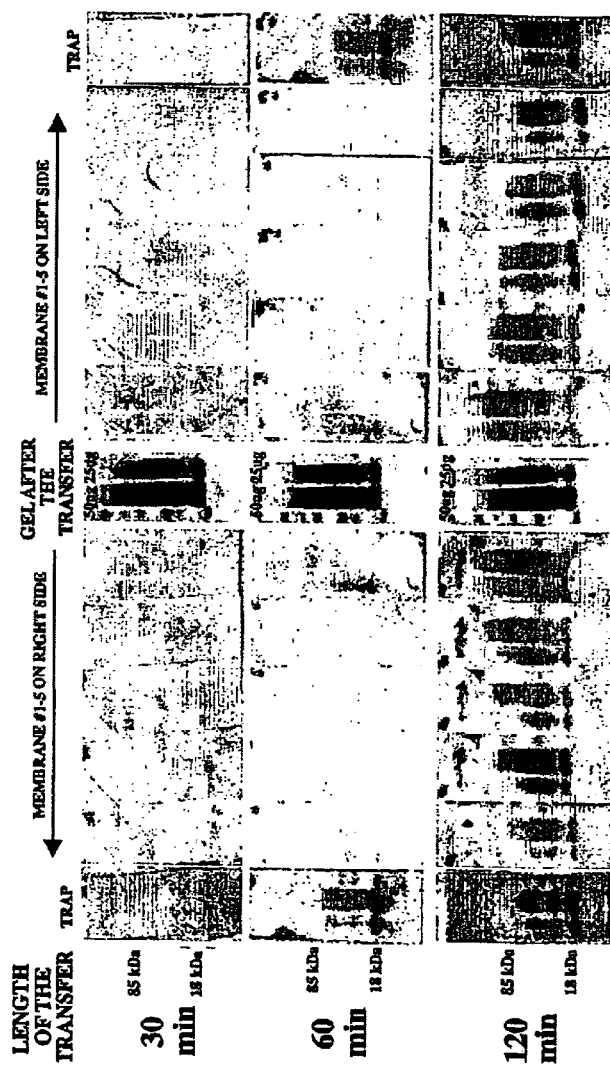
FIG. 39 is a photograph showing distribution of total protein transferred by a method provided herein.

The results of this procedure are shown in FIG. 39. Proteins were effectively transferred from the gel into the membranes on both sides of the gel (bi-directional transfer). The amount of the protein transferred was dependent on the length of the transfer (more protein was transferred after two hours compared to half an hour) and the size of the protein (transfer of the large proteins was less efficient). Thus, contact transfer is an effective alternative to electrotransfer of proteins and other biomolecules onto/into membrane stacks.

Although certain embodiments have been described herein, it will be apparent to those skilled in the art to which the invention pertains that variations and modifications of the described embodiments may be made without departing from the spirit and scope of the disclosure. Accordingly, it is intended that the invention be limited only to the extent required by the appended claims and the applicable rules of law. The references cited above are incorporated herein in their entirety.

What is claimed is:

1. A method of analyzing biomolecules from a tissue sample, comprising:
    providing a plurality of separable, porous membranes in a stack for capturing biomolecules from the tissue sample;
    positioning one face of the stack of membranes in contact with the tissue sample;
    applying heat and/or pressure to the tissue sample, whereupon biomolecules are transferred from the tissue sample onto at least one membrane of the stack;
    separating individual membranes from the stack after transfer of biomolecules to the membranes takes place; and
    analyzing one or more of the biomolecules transferred to one or more of the membranes.

2. The method of claim 1, wherein the tissue sample is an archival tissue sample, a cryo-preserved tissues ample, a fresh tissue sample, an LCM-harvested tissue sample, or a tissue microarray.

3. The method of claim 1, wherein at least one membrane in the stack is a porous membrane of no more than 30 microns thickness, comprising a core substrate and a coating.

4. The method of claim 1, wherein the core substrate comprises polycarbonate.

5. The method of claim 3, wherein the coating comprises nitrocellulose.

6. The method of claim 3 wherein the core substrate comprises a material selected from the group consisting of polycarbonate, cellulose acetate, and mixtures thereof.

7. The method of claim 3, wherein the material comprising the core substrates is selected independently for at least two membranes of the stack.

8. The method of claim 3, wherein the material comprising the core substrates of each membrane of the stack is the same.

9. The method according to claim 3 wherein the coating comprises a material for increasing the affinity of the membranes to the biomolecules.

10. The method of claim 3, wherein the coating is selected from the group consisting of nitrocellulose, poly-L-lysine, and mixtures thereof.

11. The method of claim 3, wherein the coating on the membranes is selected independently for at least two membranes of the stack.

12. The method of claim 3, wherein each of the membranes of the stack is coated with the same material.

13. The method of claim 3, wherein the coating comprises a biomolecule-specific ligand.

14. The method of claim 3, wherein the core substrate comprises a polycarbonate substrate and the coating comprises nitrocellulose.

15. The method of claim 1, wherein analyzing one or more of the biomolecules comprises detecting the biomolecules on one or more of the separated membranes.

16. Th method of claim 1, wherein the stack comprises 5 or more membranes.

17. The method of claim 1, wherein the stack comprises 50 or more membranes.

18. The method of claim 1, wherein the tissue sample is a tissue microray.

19. The method 18, further comprising the step of providing a tissue microarray.

20. The method of claim 1, wherein the tissue sample is embedded on an LCM transfer film.

21. The method of claim 20, wherein positioning one face of the stack of membranes in contact with the tissue sample comprises positioning the stack adjacent to the LCM transfer film.

22. The method of claim 1, wherein the biomolecules comprise a nucleic acid, a protein, a lipid, a carbohydrate, or a combination or mixture thereof.

23. The method of claim 22, wherein the substantially two dimensional sample is selected from the group consisting of a tissue section, a tissue microarray, a LCM harvested sample, a one-dimensional electrophoretic gel, a two-dimensional electrophoretic gel, a structurally transformed sample, or a combination of two or more thereof.

24. The method of claim 1, further comprising correlating the biomolecules detected on at least one membrane of the stack with a biological characteristic of the sample.

25. The method of claim 1, wherein the sample is a substantially two-dimensional sample.

26. The method of claim 1, wherein the membranes have a thickness of less than 30 microns.

* * * * *

SEQUENCE LISTING

```
<160> NUMBER OF SEQ ID NOS: 1

<210> SEQ ID NO 1
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 1
tcgacctctt ctgatgactc tttggaattt ctttaaaccc cca                    43
```